United States Patent [19]

Wittrup et al.

[11] Patent Number: 5,773,245
[45] Date of Patent: Jun. 30, 1998

[54] METHODS FOR INCREASING SECRETION OF OVEREXPRESSED PROTEINS

[75] Inventors: Karl Dane Wittrup, Urbana; Anne Skaja Robinson, Champaign, both of Ill.

[73] Assignee: Research Corporation Technologies, Inc., Tucson, Ariz.

[21] Appl. No.: 441,139

[22] Filed: May 15, 1995

Related U.S. Application Data

[63] Continuation of Ser. No. 89,997, Jul. 6, 1993, abandoned, which is a continuation of Ser. No. 956,699, Oct. 2, 1992, abandoned.

[51] Int. Cl.$^6$ .............................. C12P 21/02; C12N 15/67
[52] U.S. Cl. ....................... 435/69.1; 435/69.2; 435/69.3; 435/69.51; 435/69.52; 435/69.6; 435/69.7; 935/37
[58] Field of Search .................................. 435/69.1, 69.2, 435/69.3, 69.4, 69.5, 69.51, 69.52, 69.6; 935/37

[56] References Cited

U.S. PATENT DOCUMENTS 5,578,466  11/1996  Hayano et al. ......................... 435/69.1

OTHER PUBLICATIONS

Buchner et al. (1992) "Renaturation of a Single–Chain Immunotoxin Facilitated by Chaperons and Protein Disulfide Isomerase", *Bio/Technology* 10, 682–685.
Deshaies et al. (1988) "A Subfamily of Stress Proteins Facilitates Translocation of Secretory and Mitochondrial Precursor Polypeptides", *Nature* 332, 800–805.
Dorner et al. (1988) "Reduction of Endogenous GRP78 Levels Improves Secretion of a Heterologous Protein in CHO Cells", *Molecular and Cellular Biology* 8, 4063–4070.
Dorner et al. (1989) "Increased Synthesis of Secreted Proteins Induces Expression of Glucose–Regulated Proteins in Butyrate–Treated Chinese Hamster Ovary Cells", *Journal of Biological Chemistry* 264, 20602–20607.
Dorner et al. (1992) "Overexpression of GRP78 Mitigates Stress Induction of Glucose Regulated Proteins and Blocks Secretion of Selective Proteins in Chinese Hamster Ovary Cells", *The EMBO Journal* 11, ,1563–1571.
Edman et al. (1985) "Sequence of Protein Disulfide Isomerase and Implications of its Relationship to Thioredoxin", *Nature* 317, 267–270.
Ellis (1991) "Molecular Chaperones", *Annu. Rev. Biochem.* 60, 321–346.
Freedman (1989) "Protein Disulfide Isomerase: Multiple Roles in the Modification of Nascent Secretory Proteins", *Cell* 57, 1069–1072.
Gatenby et al. (1990) "Chaperonin Assisted Polypeptide Folding and Assembly: Implications for the Production of Functional Proteins in Bacteria", *Trends in Biotechnology* 8, 354–358.

Gething et al. (1992) "Protein Folding in the Cell", *Nature* 355, 33–45.
Horwich et al. (1990) "Protein–Catalysed Protein Folding", *TIBTECH* 8, 126–131.
Kim et al. (1992) "Transient Aggregation of Nascent Thyroglobulin in the Endoplasmic Reticulum: Relationship to the Molecular Chaperone, BiP", *Journal of Cell Biology* 118, 541–549.
Knittler et al. (1992) "Interaction of BiP with Newly Synthesized Immunoglobulin Light Chain Molecules: Cycles of Sequential Binding and Release", *The EMBO Journal 11*, 1573–1581.
LaMantia et al. (1991) "Glycosylation Site Binding Protein and Protein Disulfide Isomerase are Identical and Essential for Cell Viability in Yeast", *Proc. Natl. Acad. Sci. USA* 88, 4453–4457.
Landry et al. (1991) "Recognition of Nascent Polypeptides for Targeting and Folding", *TIBS* 16, 159–163.
Lee et al. (1992) "Effect of Overproduction of Heat Shock Chaperones GroESL and Dnak on Human Procollagenase Production in *Escherichia Coli,*" *J. Biol. Chem.* 267, 2849–2852.
Mazzarella et al. (1990) "ERp72, An Abundant Luminal Endoplasmic Reticulum Protein, Contains Three Copies of the Active Site Sequences of Protein Disulfide Isomerase", *The Journal of Biological Chemistry* 265, 1094–1101.
Mizunaga et al. (1990) "Purification and Characterization of Yeast Protein Disulfide Isomerase", *J. Biochem.* 108, 846–851.
Ng et al. (1992) "Analysis In Vivo of GRP78–BiP/Substrate Interactions and Their Role in Induction of the GRP78–BiP Gene", *Molecular Biology of the Cell* 3, 143–155.
Normington et al. (1989) "*S. Cerevisiae* Encodes an Essential Protein Homologous in Sequence and Function to Mammalian BiP", *Cell* 57, 1223–1236.
Pelham (1988) "Coming in from the Cold", *Nature* 332, 776–777.
Pelham (1989) "Control of Protein Exit from the Endoplasmic Reticulum", *Annu. Rev. Cell. Biol.* 5, 1–23.
Phillips et al. (1990) "Heat–Shock Proteins Dnak and GroEL Facilitate Export of LacZ Hybrid Proteins in *E. Coli,*" *Nature* 344, 882–884.
Pihlajaniemi et al. (1987) "Molecular Cloning of the β–Subunit of Human Prolyl 4–Hydroxylase. This Subunit and Protein Disulfide Isomerase are Products of the Same Gene", *The EMBO Journal* 6, 643–649.
Robinson et al. (1992) "Interaction of KAR2/BiP with Foreign Proteins Secreted in Yeast", *Abstr. Pap. Am. Chem. Soc. 203:* Abs. No. 45.

(List continued on next page.)

*Primary Examiner*—Robert A. Wax
*Assistant Examiner*—Gabriele E. Bugaisky
*Attorney, Agent, or Firm*—Scully, Scott, Murphy & Presser

[57] ABSTRACT

The present invention is directed to methods for increasing secretion of an overexpressed gene product present in a host cell, by inducing expression of chaperone proteins within the host cell.

13 Claims, 4 Drawing Sheets

OTHER PUBLICATIONS

Rose et al. (1989) "KAR2, A Karyogamy Gene, Is the Yeast Homolog of the Mammalian BiP/GRP78 Gene", *Cell 57*, 1211–1221.

Rothman (1989) "Polypeptide Chain Binding Proteins: Catalysts of Protein Folding and Related Processes in Cells", *Cell 59*, 591–601.

Schonberger et al. (1991) "Targeting and Asembly of an Oligomeric Bacterial Enterotoxoid in the Endoplasmic Reticulum of *Saccharomyces Cerevisiae*", *Molecular Microbiology 5*, 2663–2671.

Suzuki et al. (1991) Regulating the Retention of T–Cell Receptor α–Chain Variants within the Endoplasmic Reticulum: $Ca^{2+}$–Dependent Association with BiP, *The Journal of Cell Biology 114*, 189–205.

Voet et al. (1990) *Biochemistry*, J. Wiley and Sons, Inc., pp. 45–50, 419.

Yamauchi et al. (1987) "Sequence of Membrane–Associated Thyroid Hormone Binding Protein from Bovine Liver: Its Identity with Protein Disulfide Isomerase", *Biochemical and Biophysical Research Communications 146*, 1485–1492.

METHODS FOR INCREASING SECRETION OF OVEREXPRESSED PROTEINS

This is a continuation of application Ser. No. 08/089,997, filed on Jul. 6, 1993 now abandoned is a continuation of Ser. No. 07/956,699 filed on Oct. 2, 1992 now abandoned.

This invention was made with United States government support under grant number BSC-9057677 awarded by the National Science Foundation. The United States government has certain rights in the invention.

FIELD OF THE INVENTION

The present invention relates to methods for increasing protein secretion of overexpressed gene products by enhancing chaperone protein expression within a host cell. Chaperone proteins which can increase protein secretion include protein folding chaperone proteins which bind to and assist in the folding of unfolded polypeptides. Such protein folding chaperone proteins include heat shock protein 70 (hsp70) class of proteins such as mammalian or yeast HSP68, HSP70, HSP72, HSP73, clathrin uncoating ATPase, IgG heavy chain binding protein (BiP), glucose-regulated proteins 75, 78 and 80 (GRP75, GRP78 and GRP80), HSC70, and yeast KAR2, BiP, SSA1-4, SSB1, SSD1 and the like. Chaperone proteins which can increase protein secretion also include enzymes which catalyze covalent modification of proteins, such as mammalian or yeast protein disulfide isomerase (PDI), prolyl-4-hydroxylase β-subunit, ERp59, glycosylation site binding protein (GSBP) and thyroid hormone binding protein (T3BP).

BACKGROUND OF THE INVENTION

Many proteins can be reversibly unfolded and refolded in vitro at dilute concentrations since all of the information required to specify a compact folded protein structure is present in the amino acid sequence of a protein. However, protein folding in vivo occurs in a concentrated milieu of numerous proteins in which intermolecular aggregation reactions compete with the intramolecular folding process.

Moreover, gene products which are highly overexpressed are often poorly secreted even though secretion signals are present on such overexpressed gene products (Biemans et al. 1991 *DNA Cell Biol.* 10: 191–200; Elliot et al. 1989 *Gene* 79: 167–180; and Moir et al. 1987 *Gene* 56: 209–217). The prior art has not provided a clear reason for, or a simple and efficient means to overcome, such poor secretion of overexpressed gene products.

Recently, a class of proteins have been identified which are associated with the intracellular folding of nascently formed polypeptides. Such proteins have been named 'chaperone' proteins (e.g. see reviews by Ellis et al. 1991 *Annu. Rev. Biochem.* 60: 321–347; Gething et al. (1992) Nature 355: 33–45; Rothman 1989 *Cell* 59: 591–601; Horwich et al. 1990 *TIBTECH* 8: 126–131; and Morimoto et al. (Eds.) 1990 *Stress Proteins in Biology and Medicine,* Cold Spring Harbor Press: Cold Spring Harbor, N.Y., pp. 1–450).

At least two classes of chaperone proteins are involved in polypeptide folding in cells. Enzymes such as protein disulfide isomerase (PDI) and peptidyl prolyl isomerase (PPI) can covalently modify proteins by catalyzing specific isomerization steps that may limit the folding rate of some proteins. (Freedman, R. B. 1989 *Cell* 57: 1067–1072). Another type of chaperone binds to folding intermediates but not to folded proteins and apparently causes no covalent modification of such intermediates. This latter type is referred to herein as a protein folding chaperone.

Chaperone proteins that can covalently modify proteins include PDI and PPI. PDI catalyzes thiol/disulfide interchange reactions and promotes disulfide formation, isomerization or reduction, thereby facilitating the formation of the correct disulfide pairings, and may have a more general role in the prevention of premature misfolding of newly translocated chains.

PDI interacts directly with newly synthesized secretory proteins and is required for the folding of nascent polypeptides in the endoplasmic reticulum (ER) of eukaryotic cells. Enzymes found in the ER with PDI activity include mammalian PDI (Edman et al., 1985, *Nature* 317:267), yeast PDI (Mizunaga et al. 1990, *J. Biochem.* 108:848), mammalian ERp59 (Mazzarella et al., 1990, *J. Biochem.* 265:1094), mammalian prolyl-4-hydroxylase (Pihlajaniemi et al., 1987, *EMBO J.* 6: 643) yeast GSBP (Lamantia et al., 1991, *Proc. Natl. Acad. Sci. USA,* 88:4453) and mammalian T3BP (Yamauchi et al., 1987, *Biochem. Biophys. Res. Commun.* 146:1485), and yeast EUG1 (Tachibana et al., 1992, *Mol. Cell Biol.* 12, 4601).

Two major families of protein folding chaperones have been identified, a heat shock protein 60 (hsp60) class and a heat shock protein 70 (hsp70) class. Chaperones of the hsp60 class are structurally distinct from chaperones of the hsp70 class. In particular, hsp60 chaperones appear to form a stable scaffold of two heptamer rings stacked one atop another which interacts with partially folded elements of secondary structure (Ellis et al. 1991; and Landry et al. 1992 *Nature* 355: 455–457). On the other hand, hsp70 chaperones are monomers or dimers and appear to interact with short extended regions of a polypeptide (Freiden et al. 1992 *EMBO J.* 11: 63–70; and Landry et al. 1992). Hsp70 and hsp60 chaperones may also have sequential and complementary protein folding roles wherein hsp70 proteins bind to extended polypeptide chains to prevent aggregation and hsp60 oligomers complete the folding of the extended polypeptide chain (Langer et al. 1992 *Nature* 354: 683–689).

While hsp60 homologs appear to exist mainly within mitochondria and chloroplasts of eukaryotic cells, most compartments of eukaryotic cells contain members of the hsp70 class of chaperones. A eukaryotic hsp70 homolog originally identified as the IgG heavy chain binding protein (BiP) is now known to have a more general role in associating with misfolded, unassembled or aberrantly glycosylated proteins. BiP is located in all eukaryotic cells within the lumen of the endoplasmic reticulum (ER). BiP is a soluble protein which is retained in the ER by a receptor-mediated recycling pathway and perhaps by calcium crosslinking (Pelham 1989 *Annu. Rev. Cell. Biol.* 5: 1–23; Sambrook 1990 *Cell* 61: 197–199).

Hsp70 chaperones are well conserved in sequence and function (Morimoto et al. 1990). For example, the DnaK hsp70 protein chaperone in *Escherichia coli,* shares about 50% sequence homology with an hsp70 KAR2 chaperone in yeast (Rose et al. 1989 *Cell* 57:1211–1221). Moreover, the presence of mouse BiP in yeast can functionally replace a lost yeast KAR2 gene (Normington et al. 19: 1223–1236). Such a high structural and functional conservation for BiP has led to a generic usage for the term BiP as meaning any protein folding chaperone which resides in the endoplasmic reticulum of eukaryotes ranging from yeast to humans.

The first step in the eukaryotic secretory pathway is translocation of the nascent polypeptide across the ER membrane in extended form. Correct folding and assembly of a polypeptide occurs in the ER and is a prerequisite for transport from the ER through the secretory pathway (Pelham 1989 *Annu. Rev. Cell. Biol.* 5: 1–23; Gething et al. 1990 *Curr. Op. Cell Biol.* 1: 65–72). For example, translocation intermediates which are artificially lodged in microsomal membranes in vitro can be chemically crosslinked with BiP (Sanders et al. 1992 *Cell* 69: 354–365). Therefore, misfolded proteins are retained in the ER, often in association with BiP (Suzuki et al. 1991 *J. Cell Biol.* 114: 189–205).

The association of chaperone proteins with misfolded proteins has led some workers to conclude that hsp70 chaperone proteins like BiP act as proofreading proteins, whose chief role is to bind to and prevent secretion of misfolded proteins (Dorner et al. 1988 *J. Mol. & Cell. Biol.* 8:4063–4070; Dorner et al. 1992 *EMBO J.* 11: 1563–1571). Dorner et al. (1992) have also suggested that overexpression of the BiP hsp70 chaperone protein can actually block secretion of selected proteins in Chinese hamster ovary cells. Therefore, according to the prior art, the role of BiP is to inhibit protein secretion.

In contrast, the present invention provides methods for increasing protein secretion, unexpectedly, by increasing expression of an hsp70 chaperone protein or a PDI chaperone protein. Moreover, according to the present invention, it has been discovered that soluble forms of PDI and hsp70 chaperone protein are diminished in cells which have been caused to overexpress a gene product. Therefore, the present methods can be used for increasing protein secretion by circumventing this diminution of PDI and/or hsp70 chaperone protein expression.

SUMMARY OF THE INVENTION

The present invention provides a method for increasing secretion of overexpressed gene products from a host cell, which comprises expressing at least one chaperone protein in the host cell. In the present context, an overexpressed gene product is one which is expressed at levels greater than normal endogenous expression for that gene product. Overexpression can be effected, for example, by introduction of a recombinant construction that directs expression of a gene product in a host cell, or by altering basal levels of expression of an endogenous gene product, for example, by inducing its transcription.

In one embodiment, the method of the invention comprises effecting the expression of at least one chaperone protein and an overexpressed gene product in a host cell, and cultivating said host cell under conditions suitable for secretion of the overexpressed gene product. The expression of the chaperone protein and the overexpressed gene product can be effected by inducing expression of a nucleic acid encoding the chaperone protein and a nucleic acid encoding the overexpressed gene product wherein said nucleic acids are present in a host cell. In another embodiment, the expression of the chaperone protein and the overexpressed gene product are effected by introducing a first nucleic acid encoding a chaperone protein and a second nucleic acid encoding a gene product to be overexpressed into a host cell under conditions suitable for expression of the first and second nucleic acids. In a preferred embodiment, one or both of said first and second nucleic acids are present in expression vectors.

In another embodiment, expression of said chaperone protein is effected by inducing expression of a nucleic acid encoding said chaperone protein wherein said nucleic acid is present in a host cell or by introducing a nucleic acid encoding said chaperone protein into a host cell. Expression of said second protein is effected by inducing expression of a nucleic acid encoding said gene product to be overexpressed wherein said nucleic acid is present in a host cell or by introducing a nucleic acid encoding said second gene product into the host cell.

In a preferred embodiment, the host cell is a yeast cell or a mammalian cell.

In another preferred embodiment, the chaperone protein is an hsp70 chaperone protein or a protein disulfide isomerase. The hsp70 chaperone protein is preferably yeast KAR2 or mammalian BiP. The protein disulfide isomerase is preferably yeast PDI or mammalian PDI.

The present invention further provides a method for increasing secretion of an overexpressed gene product in a yeast host cell by using a yeast KAR2 chaperone protein, or yeast PDI, or yeast KAR2 in combination with yeast PDI, in the present methods.

The present invention also provides a method for increasing secretion of an overexpressed gene product in a mammalian host cell by using a mammalian BiP chaperone protein, or mammalian PDI, or mammalian BiP in combination with mammalian PDI, in the present methods.

BRIEF DESCRIPTIONS OF THE DRAWINGS

FIG. 1 depicts the amounts of soluble KAR2 protein present in cell extracts of wild type yeast and yeast strains overexpressing human erythropoietin (EPO), human platelet derived growth factor B chain (PDGF), human granulocyte colony stimulating factor (GCSF), *Schizosaccharomyces pombe* acid phosphatase (PHO) and a fusion between GCSF and PHO (GCSF-PHO) in a constitutive manner.

FIG. 2 depicts a pMR1341 expression vector which contains the yeast KAR2 gene. As depicted, this vector encodes ampicillin resistance ($Amp^R$), a pSC101 origin of replication (ori pSC101), a CEN4 centromeric sequence, an ARS1 autonomous replication sequence, a URA3 selectable marker and the PGAL1 promoter is used to effect expression of the KAR2 chaperone protein. In other experiments the URA3 selectable marker was deleted and replaced with HIS and LEU selectable markers.

FIG. 3 depicts the KAR2 expression observed in cell extracts collected from wild type cells (■), cells transformed with the EPO-encoding plasmid only (●, GalEpo) and cells transformed with both the EPO-encoding plasmid and the KAR2-encoding plasmid (▲, GalEpo+GalKar2) at 24, 48 and 72 hours after induction of KAR2 and EPO expression.

FIG. 4 depicts the growth of wild type cells (□), cells transformed with the EPO-encoding plasmid only (○, GalEpo) and cells transformed with both the EPO-encoding plasmid and the KAR2-encoding plasmid (Δ, GalEpo+ GalKar2). The inset provided in FIG. 4 depicts the amount of EPO secreted into the medium of cells having the EPO-encoding plasmid only (GalEpo) compared with the amount of secreted EPO for cells having both the EPO-encoding plasmid and the KAR2-encoding plasmid (GalEpo+GalKar2) during exponential growth of these yeast strains at the indicated time point (arrow).

DETAILED DESCRIPTION OF THE INVENTION

Figure 1:
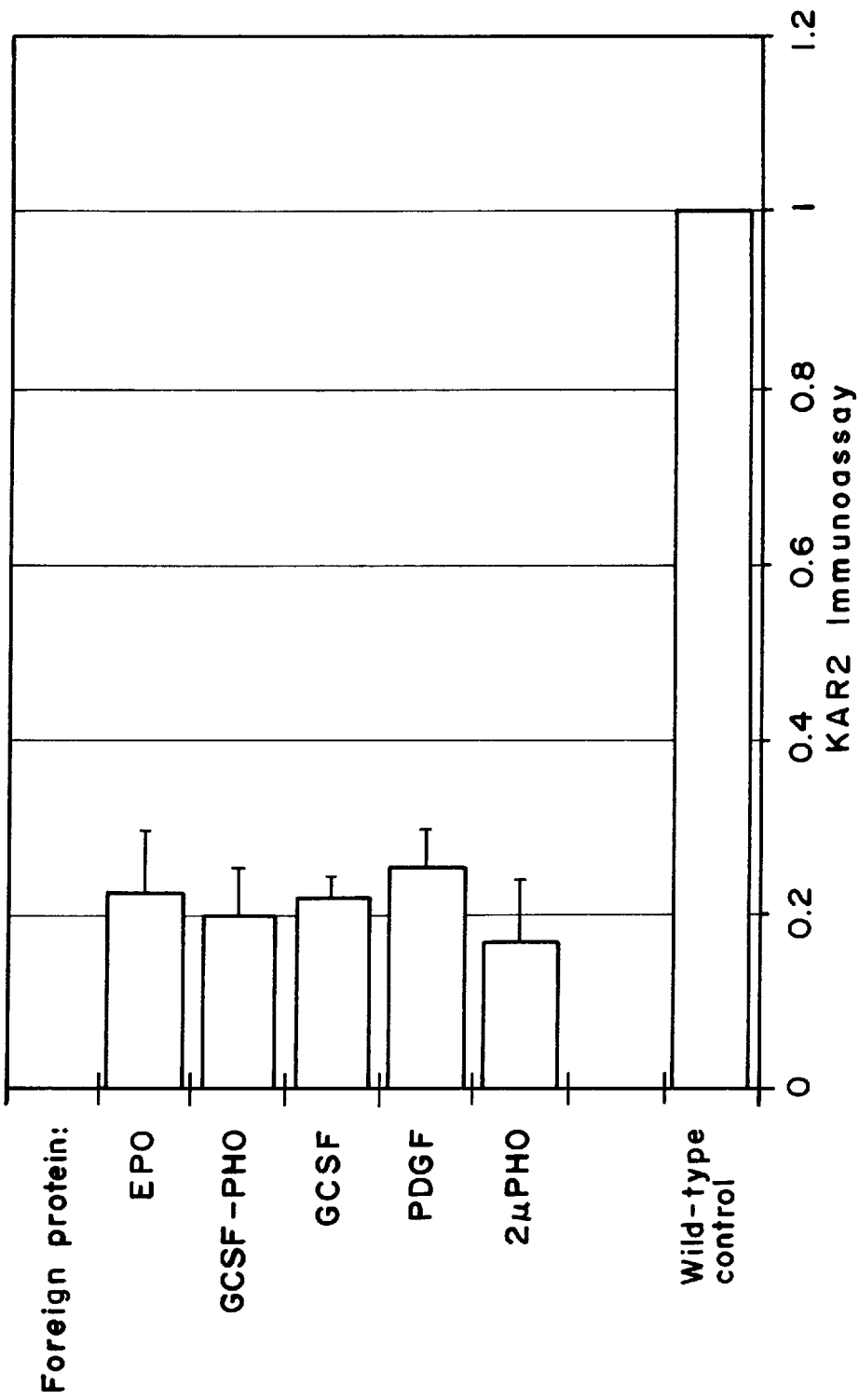

According to the present invention, it has been discovered that the amount of chaperone proteins can be diminished in cells during overexpression of a gene product and this diminution in chaperone protein levels can lead to depressed protein secretion. Moreover, in accordance with the present invention it has been found that an increase in chaperone protein expression can increase secretion of an overexpressed gene product.

Therefore, the present invention relates to a method for increasing secretion of an overexpressed gene product present in a host cell, which includes expressing a chaperone protein in the host cell and thereby increasing secretion of the overexpressed gene product.

The present invention also contemplates a method of increasing secretion of an overexpressed gene product from a host cell by expressing a chaperone protein encoded by an expression vector present in or provided to the host cell, thereby increasing the secretion of the overexpressed gene product.

The present invention provides a method for increasing secretion of overexpressed gene products from a host cell, which comprises expressing at least one chaperone protein in the host cell. In the present context, an overexpressed gene product is one which is expressed at levels greater than normal endogenous expression for that gene product. Overexpression can be effected, for example, by introduction of a recombinant construction that directs expression of a gene product in a host cell, or by altering basal levels of expression of an endogenous gene product, for example, by inducing its transcription.

In one embodiment, the method of the invention comprises effecting the expression of at least one chaperone protein and an overexpressed gene product in a host cell, and cultivating said host cell under conditions suitable for secretion of the overexpressed gene product. The expression of the chaperone protein and the overexpressed gene product can be effected by inducing expression of a nucleic acid encoding the chaperone protein and a nucleic acid encoding the overexpressed gene product wherein said nucleic acids are present in a host cell.

In another embodiment, the expression of the chaperone protein and the overexpressed gene product are effected by introducing a first nucleic acid encoding a chaperone protein and a second nucleic acid encoding a gene product to be overexpressed into a host cell under conditions suitable for expression of the first and second nucleic acids. In a preferred embodiment, one or both of said first and second nucleic acids are present in expression vectors.

In another embodiment, expression of said chaperone protein is effected by inducing expression of a nucleic acid encoding said chaperone protein wherein said nucleic acid is present in a host cell or by introducing a nucleic acid encoding said chaperone protein into a host cell. Expression of said second protein is effected by inducing expression of a nucleic acid encoding said gene product to be overexpressed wherein said nucleic acid is present in a host cell or by introducing a nucleic acid encoding said second gene product into the host cell.

In a preferred embodiment, the host cell is a yeast cell or a mammalian cell.

In another preferred embodiment, the chaperone protein is an hsp70 chaperone protein or a protein disulfide isomerase. The hsp70 chaperone protein is preferably yeast KAR2 or mammalian BiP. The protein disulfide isomerase is preferably yeast PDI or mammalian PDI.

The present invention further provides a method for increasing secretion of an overexpressed gene product in a yeast host cell by using a yeast KAR2 chaperone protein, or yeast PDI, or yeast KAR2 in combination with yeast PDI, in the present methods.

The present invention also provides a method for increasing secretion of an overexpressed gene product in a mammalian host cell by using a mammalian BiP chaperone protein, or mammalian PDI, or mammalian BiP in combination with mammalian PDI, in the present methods.

Chaperone proteins of the present invention include any chaperone protein which can facilitate or increase the secretion of proteins. In particular, members of the protein disulfide isomerase and heat shock 70 (hsp70) families of proteins are contemplated. An uncapitalized "hsp70" is used herein to designate the heat shock protein 70 family of proteins which share structural and functional similarity and whose expression are generally induced by stress. To distinguish the hsp70 family of proteins from the single heat shock protein of a species which has a molecular weight of about 70,000, and which has an art-recognized name of heat shock protein-70, a capitalized HSP70 is used herein. Accordingly, each member of the hsp70 family of proteins from a given species has structural similarity to the HSP70 protein from that species.

The present invention is directed to any chaperone protein having the capability to stimulate secretion of an overexpressed gene product. The members of the hsp70 family of proteins are known to be structurally homologous. Moreover, according to the present invention any hsp70 chaperone protein having sufficient homology to the KAR2 polypeptide sequence can be used in the present methods to stimulate secretion of an overexpressed gene product. Members of the PDI family are also structurally homologous, and any PDI which can be used according to the present method is contemplated herein. In particular, mammalian and yeast PDI, prolyl-4-hydroxylase β-subunit, ERp59, GSBP and T3BP and yeast EUG1 are contemplated.

As used herein, homology between polypeptide sequences is the degree of colinear similarity or identity between amino acids in one polypeptide sequence with that in another polypeptide sequence. Hence, homology can sometimes be conveniently described by the percentage, i.e. proportion, of identical amino acids in the sequences of the two polypeptides. For the present invention sufficient homology means that a sufficient percentage of sequence identity exists between an hsp70 chaperone polypeptide sequence and the KAR2 polypeptide sequence of SEQ ID NO:2, or between a PDI protein and the yeast PDI polypeptide sequence of SEQ ID NO:18 or the mammalian PDI sequence of SEQ ID NO:20 to retain the requisite function of the chaperone protein, i.e. stimulation of secretion.

Therefore a sufficient number, but not necessarily all, of the amino acids in the present hsp70 chaperone polypeptide sequences are identical to the KAR2 polypeptide sequence of SEQ ID NO:2, or the yeast PDI polypeptide sequence of SEQ ID NO:18 or the mammalian PDI polypeptide of SEQ ID NO:20. In particular, the degree of homology between an hsp70 chaperone protein of the present invention and the polypeptide sequence of SEQ ID NO:2 need not be 100% so long as the chaperone protein can stimulate a detectable amount of gene product secretion. However, it is preferred that the present hsp70 chaperone proteins have at least about 50% homology with the polypeptide sequence of SEQ ID NO:2. In an especially preferred embodiment sufficient homology is greater than 60% homology with the KAR2 polypeptide sequence of SEQ ID NO:2. Similarly, the degree of homology between a PDI chaperone protein and the polypeptide sequence or SEQ ID NO:18 or 20 need not be 100% so long as the chaperone protein can stimulate a detectable amount of a gene product secretion. At least about 50% homology is preferred.

The number of positions which are necessary to provide sufficient homology to KAR2 or PDI to retain the ability to stimulate secretion can be assessed by standard procedures for testing whether a chaperone protein of a given sequence can stimulate secretion.

Procedures for observing whether an overexpressed gene product is secreted are readily available to the skilled artisan. For example, Goeddel, D. V. (Ed.) 1990, Gene Expression Technology, *Methods in Enzymology,* Vol 185, Academic Press, and Sambrook et al. 1989, *Molecular Cloning: A Laboratory Manual,* Vols. 1–3, Cold Spring Harbor Press, N.Y., provide procedures for detecting secreted gene products.

To secrete an overexpressed gene product the host cell is cultivated under conditions sufficient for secretion of the overexpressed gene product. Such conditions include temperature, nutrient and cell density conditions that permit secretion by the cell. Moreover, such conditions are conditions under which the cell can perform basic cellular functions of transcription, translation and passage of proteins from one cellular compartment to another and are known to the skilled artisan.

Moreover, as is known to the skilled artisan a secreted gene product can be detected in the culture medium used to maintain or grow the present host cells. The culture medium can be separated from the host cells by known procedures, e.g. centrifugation or filtration. The overexpressed gene product can then be detected in the cell-free culture medium by taking advantage of known properties characteristic of the overexpressed gene product. Such properties can include the distinct immunological, enzymatic or physical properties of the overexpressed gene product.

For example, if an overexpressed gene product has a unique enzyme activity an assay for that activity can be performed on the culture medium used by the host cells. Moreover, when antibodies reactive against a given overexpressed gene product are available, such antibodies can be used to detect the gene product in any known immunological assay (e.g. as in Harlowe, et al., 1988, *Antibodies: A Laboratory Manual,* Cold Spring Harbor Laboratory Press).

The secreted gene product can also be detected using tests that distinguish proteins on the basis of characteristic physical properties such as molecular weight. To detect the physical properties of the gene product all proteins newly synthesized by the host cell can be labeled, e.g. with a radioisotope. Common radioisotopes which are used to label proteins synthesized within a host cell include tritium ($^3$H), carbon-14 ($^{14}$C), sulfur-35 ($^{35}$S) and the like. For example, the host cell can be grown in $^{35}$S-methionine or $^{35}$S-cysteine medium, and a significant amount of the $^{35}$S label will be preferentially incorporated into any newly synthesized protein, including the overexpressed protein. The $^{35}$S containing culture medium is then removed and the cells are washed and placed in fresh non-radioactive culture medium. After the cells are maintained in the fresh medium for a time and under conditions sufficient to allow secretion of the $^{35}$S radiolabelled overexpressed protein, the culture medium is collected and separated from the host cells. The molecular weight of the secreted labeled protein in the culture medium can then be determined by known procedures, e.g. polyacrylamide gel electrophoresis. Such procedures are described in more detail within Sambrook et al. (1989, *Molecular Cloning: A Laboratory Manual,* Vols. 1–3, Cold Spring Harbor Press, N.Y.).

Thus for the present invention, one of ordinary skill in the art can readily ascertain which chaperone proteins have sufficient homology to KAR2 or PDI to stimulate secretion of an overexpressed gene product.

According to the present invention, hsp70 chaperone proteins include yeast KAR2, HSP70, BiP, SSA1-4, SSB1, SSC1 and SSD1 gene products and eukaryotic hsp70 proteins such as HSP68, HSP72, HSP73, HSC70, clathrin uncoating ATPase, IgG heavy chain binding protein (BiP), glucose-regulated proteins 75, 78 and 80 (GRP75, GRP78 and GRP80) and the like.

Preferred PDI chaperone proteins include yeast and mammalian PDI, mammalian ERp59, mammalian prolyl-4-hydroxylase B-subunit, yeast GSBP, yeast EUG1 and mammalian T3BP.

Preferred chaperone proteins of the present invention normally reside within the endoplasmic reticulum of the host cell. For example, chaperone proteins which are localized with the endoplasmic reticulum include KAR2, GRP78, BiP, PDI and similar proteins.

Moreover, the polypeptide sequence for the present hsp70 chaperones preferably has at least 50% sequence homology with a yeast KAR2 polypeptide sequence having SEQ ID NO:2. The hsp70 chaperone polypeptide sequences which have at least 50% sequence homology with SEQ ID NO:2 include, for example, any yeast HSP70, BiP, SSD1 and any mammalian or avian GRP78, HSP70 or HSC70.

Preferred hsp70 chaperone polypeptide sequences include, for example:

*Saccharomyces cerevisiae* KAR2 having a nucleotide sequence corresponding to SEQ ID NO:1 and a polypeptide sequence corresponding to SEQ ID NO:2 (Rose et al. 1989 *Cell* 57: 1211–1221; Normington et al. 1989 *Cell* 57: 1223–1236);

*Schizosaccharomyces pombe* HSP70 having a nucleotide sequence corresponding to SEQ ID NO:3 and a polypeptide sequence corresponding to SEQ ID NO:4 (Powell et al. 1990 *Gene* 95:105–110);

*Kluyveromyces lactis* BiP having a polypeptide sequence corresponding to SEQ ID NO:5 (Lewis et al. 1990 *Nucleic Acids Res.* 18: 6438);

*Schizosaccharomyces pombe* BiP having a nucleotide sequence corresponding to SEQ ID NO:6 and a polypeptide sequence corresponding to SEQ ID NO:7 (Pidoux et al. 1992 *EMBO J.* 11: 1583–1591);

*Saccharomyces cerevisiae* SSD1 having a nucleotide sequence corresponding to SEQ ID NO:8 and a polypeptide sequence corresponding to SEQ ID NO:9 (Sutton et al. 1991 *Mol. Cell. Biol.* 11: 2133–2148);

Mouse GRP78 having a polypeptide sequence corresponding to SEQ ID NO:10;

Hamster GRP78 having a polypeptide sequence corresponding to SEQ ID NO:11;

Human GRP78 having a nucleotide sequence corresponding to SEQ ID NO:12 (Ting et al. 1988 *DNA* 7: 275–286);

Mouse HSC70 having a nucleotide sequence corresponding to SEQ ID NO:13 and a polypeptide sequence corresponding to SEQ ID NO:14 (Giebel et al. 1988 *Dev. Biol.* 125: 200–207);

Human HSC70 having a nucleotide sequence corresponding to SEQ ID NO:15 (Dworniczak et al. 1987 *Nucleic Acids Res.* 15: 5181–5197);

Chicken GRP78 having a polypeptide sequence corresponding to SEQ ID NO:16;

Rat GRP78 as in Chang et al. (1987 *Proc. Natl. Acad. Sci. USA* 84: 680–684);

*Saccharomyces cerevisiae* SCC-1 as in Craig et al. (1987 *Proc. Natl. Acad. Sci. USA* 84: 680–684);

Preferred hsp70 proteins of the present invention are normally present in the endoplasmic reticulum of the cell. Preferred hsp70 proteins also include yeast KAR2, BiP, and HSP70 proteins, avian BiP or GRP78 proteins and mammalian BiP or GRP78 proteins.

The polypeptide sequence for the present PDI chaperones preferably has at least 50% homology with the yeast PDI of SEQ ID NO:18 or the rat PDI of SEQ ID NO:20. Preferred PDI chaperone polypeptides include, for example,

*Saccharomyces cerevisiae* PDI having a nucleotide sequence corresponding to SEQ ID NO:17 and a polypeptide sequence corresponding to SEQ ID NO:18 (La Mantia et al., 1991, *Proc. Natl. Acad. Sci. USA* 88: 4453–4457).

Rat PDI having a nucleotide sequence corresponding to SEQ ID NO:19 and a polypeptide sequence corresponding to SEQ ID NO:20 (Edman et al., 1985 *Nature*, 317:267).

Human prolyl 4-hydroxylase β-subunit having a nucleotide and amino acid sequence as disclosed by Pihlajaniemi et al., 1987, *EMBO, J.* 6: 643–649.

Bovine T3BP having a nucleotide and amino acid sequence as disclosed by Yamauchi et al, 1987, *Biochem. Biophys. Res. Commun.*, 146:1485–1492.

Murine ERp59 having a nucleotide and amino acid sequence as disclosed by Mazzarella et al., 1990, *J. Biol. Chem.* 265: 1094–1101.

As is known to the skilled artisan, a given amino acid is encoded by different three-nucleotide codons. Such degeneracy in the genetic code therefore means that the same polypeptide sequence can be encoded by numerous nucleotide sequences. The present invention is directed to methods utilizing any nucleotide sequence which can encode the present hsp70 chaperone polypeptides. Therefore, for example, while the KAR2 polypeptide sequence of SEQ ID NO:2 can be encoded by a nucleic acid comprising SEQ ID NO:1 there are alternative nucleic acid sequences which can encode the same KAR2 SEQ ID NO:2 polypeptide sequence. The present invention is also directed to use of such alternative nucleic acid sequences in the present methods.

Moreover when the host cell is a yeast host cell the chaperone protein is preferably a yeast KAR2 or BiP protein or PDI protein, e.g. SEQ ID NO:2, SEQ ID NO:5, SEQ ID NO:7, SEQ ID NO:18 and homologues thereof. Accordingly the present invention also provides a method for increasing secretion of an overexpressed gene product present in or provided to a yeast host cell, which includes expressing at least one KAR2 or BiP or PDI chaperone protein in the host cell and thereby increasing secretion of the gene product. In one embodiment such a method can also include expressing at least one of a KAR2 or BiP or PDI chaperone protein encoded by at least one expression vector present in or provided to the host cell, and thereby increasing secretion of the overexpressed recombinant gene product. Such an expression vector can include a nucleic acid encoding a polypeptide sequence for a yeast KAR2 or BiP or PDI chaperone protein operably linked to a nucleic acid which effects expression of the yeast KAR2 or BiP or PDI chaperone protein.

Yeast as used herein includes such species as *Saccharomyces cerevisiae, Hansenula polymorpha, Kluyveromyces lactis, Pichia pastoris, Schizosaccharomyces pombe, Yarrowia lipolytica* and the like.

Furthermore, when an avian or mammalian host is used a BiP or GRP78 or mammalian PDI chaperone protein is preferably employed, e.g. any one of SEQ ID NO: 10–12, 16 or 20 and homologues thereof. Therefore, the present invention also provides a method for increasing secretion of an overexpressed gene product in a mammalian host cell, which includes expressing at least one of a BiP or GRP78 or mammalian PDI chaperone protein in the host cell and thereby increasing secretion of the gene product. Such a method can also include expressing a BiP or GRP78 or mammalian PDI chaperone protein encoded by an expression vector present in or provided to the host cell and thereby increasing the secretion of the overexpressed gene product. Such an expression vector can include a nucleic acid encoding a polypeptide sequence for the BiP or the GRP78 or the mammalian PDI chaperone protein operably linked to a sequence which effects expression of such a chaperone protein.

In a preferred embodiment the chaperone protein is a mammalian or avian GRP78 protein, or a mammalian PDI.

Mammals as used herein includes mouse, hamster, rat, monkey, human and the like.

The present invention provides methods for increasing secretion of any overexpressed gene product which naturally has a secretion signal or has been genetically engineered to have a secretion signal.

Secretion signals are discrete amino acid sequences which cause the host cell to direct a gene product through internal and external cellular membranes and into the extracellular environment.

Secretion signals are present at the N-terminus of a nascent polypeptide gene product targeted for secretion. Additional eukaryotic secretion signals can also be present along the polypeptide chain of the gene product in the form of carbohydrates attached to specific amino acids, i.e. glycosylation secretion signals.

N-terminal signal sequences include a hydrophobic domain of about 10 to about 30 amino acids which can be preceded by a short charged domain of about 2 to about 10 amino acids. Moreover, the signal sequence is present at the N-terminus of gene products destined for secretion. In general, the particular sequence of a signal sequence is not critical but signal sequences are rich in hydrophobic amino acids such as alanine (Ala), valine (Val), leucine (Leu), isoleucine (Ile), proline (Pro), phenylalanine (Phe), tryptophan (Trp), methionine (Met) and the like.

Many signal sequences are known (Michaelis et al. 1982 *Ann. Rev. Microbiol.* 36: 425). For example, the yeast acid phosphatase, yeast invertase and the yeast α-factor signal sequences have been attached to heterologous polypeptide coding regions and used successfully for secretion of the heterologous polypeptide (Sato et al. 1989 *Gene* 83: 355–365; Chang et al. 1986 *Mol. Cell. Biol.* 6: 1812–1819; and Brake et al. 1984 *Proc. Natl. Acad. Sci. USA* 81: 4642–4646). Therefore, the skilled artisan can readily design or obtain a nucleic acid which encodes a coding region for an overexpressed gene product which also has a signal sequence at the 5'-end.

Eukaryotic glycosylation signals include specific types of carbohydrates which are attached to specific types of amino acids present in a gene product. Carbohydrates which are attached to such amino acids include straight or branched chains containing glucose, fucose, mannose, galactose, N-acetylglucosamine, N-acetylgalactosamine, N-acetylneuraminic acid and the like. Amino acids which are frequently glycosylated include asparagine (Asn), serine (Ser), threonine (Thr), hydroxylysine and the like.

Examples of overexpressed gene products which are preferably secreted by the present methods include mammalian gene products such as enzymes, cytokines, growth factors, hormones, vaccines, antibodies and the like. More particularly, preferred overexpressed gene products of the present invention include gene products such as erythropoietin, insulin, somatotropin, growth hormone releasing factor, platelet derived growth factor, epidermal growth factor, transforming growth factor α, transforming growth factor β, epidermal growth factor, fibroblast growth factor, nerve growth factor, insulin-like growth factor I, insulin-like growth factor II, clotting Factor VIII, superoxide dismutase, α-interferon, γ-interferon, interleukin-1, interleukin-2, interleukin-3, interleukin-4, interleukin-5, interleukin-6, granulocyte colony stimulating factor, multi-lineage colony stimulating activity, granulocyte-macrophage stimulating factor, macrophage colony stimulating factor, T cell growth factor, lymphotoxin and the like. Preferred overexpressed gene products are human gene products.

Moreover, the present methods can readily be adapted to enhance secretion of any overexpressed gene product which can be used as a vaccine. Overexpressed gene products which can be used as vaccines include any structural, membrane-associated, membrane-bound or secreted gene product of a mammalian pathogen. Mammalian pathogens include viruses, bacteria, single-celled or multi-celled parasites which can infect or attack a mammal. For example, viral vaccines can include vaccines against viruses such as human immunodeficiency virus (HIV), *R. rickettsii,* vaccinia, Shigella, poliovirus, adenovirus, influenza, hepatitis A, hepatitis B, dengue virus, Japanese B encephalitis, *Varicella zoster,* cytomegalovirus, hepatitis A, rotavirus, as well as vaccines against viral diseases like Lyme disease, measles, yellow fever, mumps, rabies, herpes, influenza, parainfluenza and the like. Bacterial vaccines can include vaccines against bacteria such as *Vibrio cholerae, Salmonella typhi, Bordetella pertussis, Streptococcus pneumoniae, Hemophilus influenza, Clostridium tetani, Corynebacterium diphtheriae, Mycobacterium leprae, Neisseria gonorrhoeae, Neisseria meningitidis, Coccidioides immitis* and the like.

Moreover, an overexpressed gene product of the present invention can be overexpressed from its own natural promoter, from a mutated form of such a natural promoter or from a heterologous promoter which has been operably linked to a nucleic acid encoding the gene product. Accordingly, overexpressed gene products contemplated by the present invention include recombinant and non-recombinant gene products. As used herein a recombinant gene product is a gene product expressed from a nucleic acid which has been isolated from the natural source of such a gene product or nucleic acid. In contrast, non-recombinant, or native, gene products are expressed from nucleic acids naturally present in the host cell.

Therefore, the present overexpressed gene products can be native products of the host cell which are naturally produced at high levels, e.g. antibodies, enzymes, cytokines, hormones and the like. Moreover, if the factors controlling expression of a native gene product are understood, such factors can also be manipulated to achieve overexpression of the gene product, e.g. by induction of transcription from the natural promoter using known inducer molecules, by mutation of the nucleic acids controlling or repressing expression of the gene product to produce a mutant strain that constitutively overexpresses the gene product, by second site mutations which depress the synthesis or function of factors which normally repress the transcription of the gene product, and the like.

Similarly, the present chaperone proteins can be expressed non-recombinantly, i.e. from the host cell's native gene for that chaperone protein, by manipulating the factors controlling expression of the native chaperone protein to permit increased expression of the chaperone protein. For example, the native hsp70 chaperone gene or the transcriptional or translational control elements for the hsp70 chaperone can be mutated so that the hsp70 chaperone protein is constitutively expressed. Alternatively, nucleic acids encoding factors which control the transcription or translation of the chaperone protein can be mutated to achieve increased expression of the chaperone protein. Such mutations can thereby overcome the decrease in native chaperone protein expression which occurs upon overexpression of a gene product.

The overexpressed gene products and the chaperone proteins of the present invention can also be expressed recombinantly, i.e. by placing a nucleic acid encoding a gene product or a chaperone protein into an expression vector. Such an expression vector minimally contains a sequence which effects expression of the gene product or the chaperone protein when the sequence is operably linked to a nucleic acid encoding the gene product or the chaperone protein. Such an expression vector can also contain additional elements like origins of replication, selectable markers, transcription or termination signals, centromeres, autonomous replication sequences, and the like.

According to the present invention, first and second nucleic acids encoding an overexpressed gene product and a chaperone protein, respectively, can be placed within expression vectors to permit regulated expression of the overexpressed gene product and/or the chaperone protein. While the chaperone protein and the overexpressed gene product can be encoded in the same expression vector, the chaperone protein is preferably encoded in an expression vector which is separate from the vector encoding the overexpressed gene product. Placement of nucleic acids encoding the chaperone protein and the overexpressed gene product in separate expression vectors can increase the amount of secreted overexpressed gene product.

As used herein, an expression vector can be a replicable or a non-replicable expression vector. A replicable expression vector can replicate either independently of host cell chromosomal DNA or because such a vector has integrated into host cell chromosomal DNA. Upon integration into host cell chromosomal DNA such an expression vector can lose some structural elements but retains the nucleic acid encoding the gene product or the hsp70 chaperone protein and a segment which can effect expression of the gene product or the chaperone protein. Therefore, the expression vectors of the present invention can be chromosomally integrating or chromosomally nonintegrating expression vectors.

In a preferred embodiment of the present invention, one or more chaperone proteins are overexpressed in a host cell by introduction of integrating or nonintegrating expression vectors into the host cell. Following introduction of at least one expression vector encoding at least one chaperone protein, the gene product is then overexpressed by inducing expression of an endogenous gene encoding the gene product, or by introducing into the host cell an expression vector encoding the gene product. In another preferred embodiment, cell lines are established which constitutively or inducibly express at least one chaperone protein. An expression vector encoding the gene product to be overexpressed is introduced into such cell lines to achieve increased secretion of the overexpressed gene product.

The present expression vectors can be replicable in one host cell type, e.g., *Escherichia coli,* and undergo little or no replication in another host cell type, e.g., a eukaryotic host cell, so long as an expression vector permits expression of the present chaperone proteins or overexpressed gene products and thereby facilitates secretion of such gene products in a selected host cell type.

Expression vectors as described herein include DNA or RNA molecules engineered for controlled expression of a desired gene, i.e. a gene encoding the present chaperone proteins or a overexpressed gene product. Such vectors also encode nucleic acid segments which are operably linked to nucleic acids encoding the present chaperone polypeptides or the present overexpressed gene products. Operably linked in this context means that such segments can effect expression of nucleic acids encoding chaperone protein or over-expressed gene products. These nucleic acid sequences include promoters, enhancers, upstream control elements, transcription factors or repressor binding sites, termination signals and other elements which can control gene expression in the contemplated host cell. Preferably the vectors are plasmids, bacteriophages, cosmids or viruses.

Sambrook et al. 1989; Goeddel, 1990; Perbal, B. 1988, *A Practical Guide to Molecular Cloning,* John Wiley & Sons, Inc.; and Romanos et al. 1992, *Yeast* 8: 423–488, provide detailed reviews of vectors into which a nucleic acid encoding the present chaperone polypeptide sequences or the contemplated overexpressed gene products can be inserted and expressed.

Expression vectors of the present invention function in yeast or mammalian cells. Yeast vectors can include the yeast $2\mu$ circle and derivatives thereof, yeast plasmids encoding yeast autonomous replication sequences, yeast minichromosomes, any yeast integrating vector and the like. A comprehensive listing of many types of yeast vectors is provided in Parent et al. (1985 Yeast 1: 83–138). Mammalian vectors can include SV40 based vectors, polyoma based vectors, retrovirus based vectors, Epstein-Barr virus based vectors, papovavirus based vectors, bovine papilloma virus (BPV) vectors, vaccinia virus vectors, baculovirus vectors and the like. Muzyczka (ed. 1992 *Curr. Top. Microbiol. Immunol.* 158:97–129) provides a comprehensive review of eukaryotic expression vectors.

Elements or nucleic acid sequences capable of effecting expression of a gene product include promoters, enhancer elements, upstream activating sequences, transcription termination signals and polyadenylation sites. All such promoter and transcriptional regulatory elements, singly or in combination, are contemplated for use in the present expression vectors. Moreover, genetically-engineered and mutated regulatory sequences are also contemplated herein.

Promoters are DNA sequence elements for controlling gene expression. In particular, promoters specify transcription initiation sites and can include a TATA box and upstream promoter elements.

Yeast promoters are used in the present expression vectors when a yeast host cell is used. Such yeast promoters include the GAL1, PGK, GAP, TPI, CYC1, ADH2, PHO5, CUP1, MFα1, MFα1 and related promoters. Romanos et al. (1992 Yeast 8: 423–488) provide a review of yeast promoters and expression vectors.

Higher eukaryotic promoters which are useful in the present expression vectors include promoters of viral origin, such as the baculovirus polyhedrin promoter, the vaccinia virus hemagglutinin (HA) promoter, SV40 early and late promoter, the herpes simplex thymidine kinase promoter, the Rous sarcoma virus LTR, the Moloney Leukemia Virus LTR, and the Murine Sarcoma Virus (MSV) LTR. Sambrook et al. (1989) and Goeddel (1990) review higher eukaryote promoters.

Preferred promoters of the present invention include inducible promoters, i.e. promoters which direct transcription at an increased or decreased rate upon binding of a transcription factor. Transcription factors as used herein include any factor that can bind to a regulatory or control region of a promoter an thereby affect transcription. The synthesis or the promoter binding ability of a transcription factor within the host cell can be controlled by exposing the host to an inducer or removing an inducer from the host cell medium. Accordingly to regulate expression of an inducible promoter, an inducer is added or removed from the growth medium of the host cell. Such inducers can include sugars, phosphate, alcohol, metal ions, hormones, heat, cold and the like. For example, commonly used inducers in yeast are glucose, galactose, and the like.

The expression vectors of the present invention can also encode selectable markers. Selectable markers are genetic functions that confer an identifiable trait upon a host cell so that cells transformed with a vector carrying the selectable marker can be distinguished from non-transformed cells. Inclusion of a selectable marker into a vector can also be used to ensure that genetic functions linked to the marker are retained in the host cell population. Such selectable markers can confer any easily identified dominant trait, e.g. drug resistance, the ability to synthesize or metabolize cellular nutrients and the like.

Yeast selectable markers include drug resistance markers and genetic functions which allow the yeast host cell to synthesize essential cellular nutrients, e.g. amino acids. Drug resistance markers which are commonly used in yeast include chloramphenicol ($Cm^r$), kanamycin ($kan^r$), methotrexate ($mtx^r$ or $DHFR^+$) G418 (geneticin) and the like. Genetic functions which allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1), uracil (URA3), histidine (HIS3), lysine (LYS2) and the like.

Higher eukaryotic selectable markers can include genetic functions encoding an enzyme required for synthesis of a required nutrient, e.g. the thymidine kinase (tk), dihydrofolate reductase (DHFR), uridine (CAD), adenosine deaminase (ADA), asparagine synthetase (AS) and the like. The presence of some of these enzymatic functions can also be identified by exposing the host cell to a toxin which can be inactivated by the enzyme encoded by the selectable marker. Moreover drug resistance markers are available for higher eukaryotic host cells, e.g. aminoglycoside phosphotransferase (APH) markers are frequently used to confer resistance to kanamycin, neomycin and geneticin, and hygromycin B phosphotransferase (hyg) confers resistance to hygromycin in higher eukaryotes. Some of the foregoing selectable markers can also be used to amplify linked genetic functions by slowly adding the appropriate substrate for the enzyme encoded by markers such as DHFR, CAD, ADA, AS and others.

Therefore the present expression vectors can encode selectable markers which are useful for identifying and maintaining vector-containing host cells within a cell population present in culture. In some circumstances selectable markers can also be used to amplify the copy number of the expression vector.

After inducing transcription from the present expression vectors to produce an RNA encoding an overexpressed gene product or a chaperone protein, the RNA is translated by cellular factors to produce the gene product or the chaperone protein.

In yeast and other eukaryotes, translation of a messenger RNA (mRNA) is initiated by ribosomal binding to the 5' cap of the mRNA and migration of the ribosome along the mRNA to the first AUG start codon where polypeptide synthesis can begin. Expression in yeast and mammalian cells generally does not require specific number of nucleotides between a ribosomal-binding site and an initiation codon, as is sometimes required in prokaryotic expression systems. However, for expression in a yeast or a mammalian host cell, the first AUG codon in an mRNA is preferably the desired translational start codon.

Moreover, when expression is performed in a yeast host cell the presence of long untranslated leader sequences, e.g. longer than 50–100 nucleotides, can diminish translation of an mRNA. Yeast mRNA leader sequences have an average length of about 50 nucleotides, are rich in adenine, have little secondary structure and almost always use the first AUG for initiation (Romanos et al. 1992; and Cigan et al. 1987 Gene 59: 1–18). Since leader sequences which do not have these characteristics can decrease the efficiency of protein translation, yeast leader sequences are preferably used for expression of an overexpressed gene product or a chaperone protein in a yeast host cell. The sequences of many yeast leader sequences are known and are available to the skilled artisan, e.g. by reference to Cigan et al. (1987 Gene 59: 1–18).

In mammalian cells, nucleic acids encoding chaperone proteins or overexpressed gene products generally include the natural ribosomal-binding site and initiation codon because, while the number of nucleotides between transcription and translational start sites can vary, such variability does not greatly affect the expression of the polypeptide in a mammalian host. However, when expression is performed in a mammalian host cell, the first AUG codon in an mRNA is preferably the desired translational start codon.

In addition to the promoter, the ribosomal-binding site and the position of the start codon, factors which can effect the level of expression obtained include the copy number of a replicable expression vector. The copy number of a vector is generally determined by the vector's origin of replication and any cis-acting control elements associated therewith. For example, an increase in copy number of a yeast episomal vector encoding a regulated centromere can be achieved by inducing transcription from a promoter which is closely juxtaposed to the centromere (Chlebowicz-Sledziewska et al. 1985 Gene 39: 25–31). Moreover, encoding the yeast FLP function in a yeast vector can also increase the copy number of the vector (Romanos et al.).

The skilled artisan has available many choices of expression vectors. For example, commonly available yeast expression vectors include pWYG-4, pWYG7L and the like. Goeddel (1990) provides a comprehensive listing of yeast expression vectors and sources for such vectors. Commercially available higher eukaryotic expression vectors include pSVL, PMSG, pKSV-10, pSVN9 and the like.

One skilled in the art can also readily design and make expression vectors which include the above-described sequences by combining DNA fragments from available vectors, by synthesizing nucleic acids encoding such regulatory elements or by cloning and placing new regulatory elements into the present vectors. Methods for making expression vectors are well-known. Overexpressed DNA methods are found in any of the myriad of standard laboratory manuals on genetic engineering (Sambrook et al., 1989; Goeddel, 1990 and Romanos et al. 1992).

For example, a centromere-containing YCp50 vector (Goeddel, 1990) which encodes a URA3 selectable marker can be modified to encode an associated inverted sequence which permits high copy number replication in yeast. A galactose inducible promoter, e.g. PGAL1, can be placed within such a vector and a chaperone polypeptide sequence, e.g., SEQ ID NO:2 can be inserted immediately downstream. A pSC101 origin of replication can also be used in such a vector to permit replication at low copy numbers in *Escherichia coli*. One such replicable expression vector which has such structural elements is a pMR1341 vector (Vogel et al. 1990 J. Cell. Biol. 110: 1885).

The expression vectors of the present invention can be made by ligating the present chaperone protein coding regions in the proper orientation to the promoter and other sequence elements being used to control gene expression. This juxtapositioning of promoter and other sequence elements with the present hsp70 chaperone polypeptide coding regions allows synthesis of large amounts of the chaperone polypeptide which can then increase secretion of a co-synthesized overexpressed protein.

After construction of the present expression vectors, such vectors are transformed into host cells where the overexpressed gene product and the chaperone protein can be expressed. Methods for transforming yeast and higher eukaryotic cells with expression vectors are well known and readily available to the skilled artisan.

For example, expression vectors can be transformed into yeast cells by any of several procedures including lithium acetate, spheroplast, electroporation and similar procedures. Such procedures can be found in numerous references including Ito et al. (1983, *J. Bacteriol.* 153: 163), Hinnen et al. (1978 *Proc. Natl. Acad. Sci. U.S.A.* 75: 1929) and Guthrie et al. (1991 Guide to Yeast Genetics and Molecular Biology, in *Methods In Enzymology*, vol. 194, Academic Press, New York).

Mammalian host cells can also be transformed with the present expression vectors by a variety of techniques including transfection, infection and other transformation procedures. For example, transformation procedures include calcium phosphate-mediated, DEAE-dextran-mediated or polybrene-mediated transformation, protoplast or liposomal fusion, electroporation, direct microinjection into nuclei and the like. Such procedures are provided in Sambrook et al. and the references cited therein.

Yeast host cells which can be used with yeast replicable expression vectors include any wild type or mutant strain of yeast which is capable of secretion. Such strains can be derived from *Saccharomyces cerevisiae, Hansenula polymorpha, Kluyveromyces lactis, Pichia pastoris, Schizosaccharomyces pombe, Yarrowia lipolytica* and related species of yeast. In general, preferred mutant strains of yeast are strains which have a genetic deficiency that can be used in combination with a yeast vector encoding a selectable marker. Many types of yeast strains are available from the Yeast Genetics Stock Center (Donner Laboratory, University of California, Berkeley, Calif. 94720), the American Type Culture Collection (12301 Parklawn Drive, Rockville, Md. 20852, hereinafter ATCC), the National Collection of Yeast Cultures (Food Research Institute, Colney Lane, Norwich NR4 7UA, UK) and the Centraalbureau voor Schimmelcultures (Yeast Division, Julianalaan 67a, 2628 BC Delft, Netherlands).

Tissue culture cells that are used with eukaryotic expression vectors can include VERO cells, NRC-5 cells, SCV-1 cells, COS-1 cells, CV-1 cells, LCC-MK$_2$ cells, NIH3T3 cells, CHO-K1 cells, mouse L cells, HeLa cells, *Antheraea eucalypti* moth ovarian cells, *Aedes aegypti* mosquito cells, S. frugiperda cells and other cultured cell lines known to one skilled in the art. Such host cells can be obtained from the ATCC. For example, Table 1 provides examples of higher eukaryotic host cells which are illustrative of the many types of host cells which can be used with the present methods. The subject matter of Table 1 is not intended to limit the invention is any respect.

The following Examples further illustrate the invention.

TABLE 1

| HOST CELL | ORIGIN | SOURCE |
| --- | --- | --- |
| Aedes aegypti | Mosquito Larvae | *ATCC #CCL 125 |
| LtK- | Mouse | Exp. Cell. Res 31:297–312 |
| CV-1 | African Green Monkey Kidney | ATCC #CCL 70 |
| LCC-MK$_2$ original | Rhesus Monkey Kidney | ATCC #CCL 7 |
| LCC-MK$_2$ derivative | Rhesus Monkey Kidney | ATCC #CCL 7.1 |
| 3T3 | Mouse Embryo Fibroblasts | ATCC #CCL 92 |
| CHO-K1 | Chinese Hamster Ovary | ATCC #CCL 61 |
| 293 | Human Embryonic Kidney | ATCC #CRL 1573 |
| Antheraea eucalypti | Moth Ovarian Tissue | ATCC #CCL 80 |
| HeLa | Human Cervix Epitheloid | ATCC #CCL 2 |
| C1271 | Mouse Fibroblast | ATCC #CRL 1616 |
| HS-Sultan | Human Plasma Cell Plasmacytoma | ATCC #CRL 1484 |
| Saccharomyces cerevisiae DBY746 | | ATCC #44773 |

*American Type Culture Collection, 1201 Parklawn Drive, Rockville, Maryland

EXAMPLE 1

Effect of Overexpression of Proteins on Native Yeast Chaperone Protein Synthesis The expression of native yeast chaperone KAR2 protein was observed in yeast cells constitutively overexpressing human gene products erythropoietin, granulocyte colony stimulating factor, platelet derived growth factor or Schizosaccharomyces pombe acid phosphatase. These non-yeast products have a variety of distinct structural features including different sizes, differences in glycosylation, and different numbers of subunits (Table 2).

Materials and Methods:

TABLE 2

STRUCTURAL FEATURES OF OVEREXPRESSED GENE PRODUCTS

| Protein[a] | Multiple Subunits? | Glycosylated? | Size (kd) |
| --- | --- | --- | --- |
| EPO | | + | 193 |
| PDGF | + | | 241 |
| GCSF | | | 207 |
| PHO | + | + | 435 |
| GCSF-PHO | + | + | 548 |

[a]EPO = human erythropoietin, PDGF = human platelet derived growth factor B chain, GCSF = human granulocyte colony stimulating factor, PHO = Schizosaccharomyces pombe acid phosphatase, and GCSF-PHO = fusion between GCSF and PHO.

Yeast YPH500 (α ura3-52 lys2-801a ade2-101 trp-Δ63 his3-Δ200 leu2-Δ1) cells were transformed with multicopy plasmids encoding one of the overexpressed gene products described in Table 2, using methods provided in Guthrie et al. and then cultured in protein-free Synthetic Complete (SC) media. Extracts from 10 ml cultures of mid-exponential growing cells were prepared by glass bead disruption (Guthrie et al). Serial dilutions were made of protein extracts from strains expressing the different gene products. Equal amounts of total protein were loaded onto a BioRad slot blotting were prepared.

The blots were probed with anti-KAR2 antibody followed by goat anti-rabbit secondary antibody conjugated to alkaline phosphatase. Alkaline phosphatase enzymatic activity was detected by use of a Lumi-Phos 530$^R$ substrate (Boehringer Mannheim) to form a chemi-luminescent product. Quantitation of the amount of KAR2 protein expressed in different cell extracts was by densitometric scanning of X-ray films exposed to blots treated with Lumi-Phos 530$^R$.

Results:

FIG. 1 depicts the amounts of KAR2 protein in wild type yeast and yeast strains which had been overexpressing human erythropoietin (EPO), human platelet derived growth factor B chain (PDGF), human granulocyte colony stimulating factor (GCSF), Schizosaccharomyces pombe acid phosphatase (PHO) and a fusion between GCSF and PHO (GCSF-PHO) for 50 or more generations.

Surprisingly, native soluble KAR2 protein levels were at least five-fold lower in cells expressing these foreign genes from multicopy plasmids. Lower levels of expression from a single-copy control plasmid (i.e. single-copy PHO) did not greatly diminish KAR2 protein expression.

Similar results were obtained when using a BJ5464 yeast strain (α ura3-52 trp1 leu2Δ1 his3Δ200 pep4::HIS3 prb1Δ1.6R can1 GAL), which is deficient in vacuolar proteases. Therefore, the differences in KAR2 expression were not due to differences in the levels of vacuolar proteases. Moreover, the addition of other protease inhibitors to the cell extracts did not change the relative amount of KAR2 protein observed. Further, mixing experiments of cellular extracts containing and not containing KAR2, confirmed that proteolysis during sample preparation was negligible. Therefore, strain-dependent differences in proteolysis could not account for the observed dimunition of KAR2 protein expression in yeast strains overexpressing proteins from multicopy plasmids.

Accordingly, the amount of native KAR2 protein in cells expressing high levels of a gene product is diminished at least 5-fold.

EXAMPLE 2

Construction of an Inducible KAR2 Expression Vector

A pMR1341 expression vector was made from a MR568 plasmid which encoded the yeast KAR2 chaperone protein having −55 base pairs (bp) from the ATG start codon (i.e. position 240 of SEQ ID NO: 1) to the terminus of the coding region at bp as provided in SEQ D NO:1. The PGAL1 promoter encoded within a SalI-AatII fragment from pB622 was placed into SalI-AatII sites within pMR568 to provide a galactose inducible promoter for the KAR2 coding region. Moreover, pMR1341 encodes a URA3 selectable marker which permits selection for this vector in ura deficient yeast host cells. In later experiments the URA3 encoding nucleic acid fragment was deleted and replaced with a fragment encoding both HIS and LEU yeast selectable markers.

Figure 2:
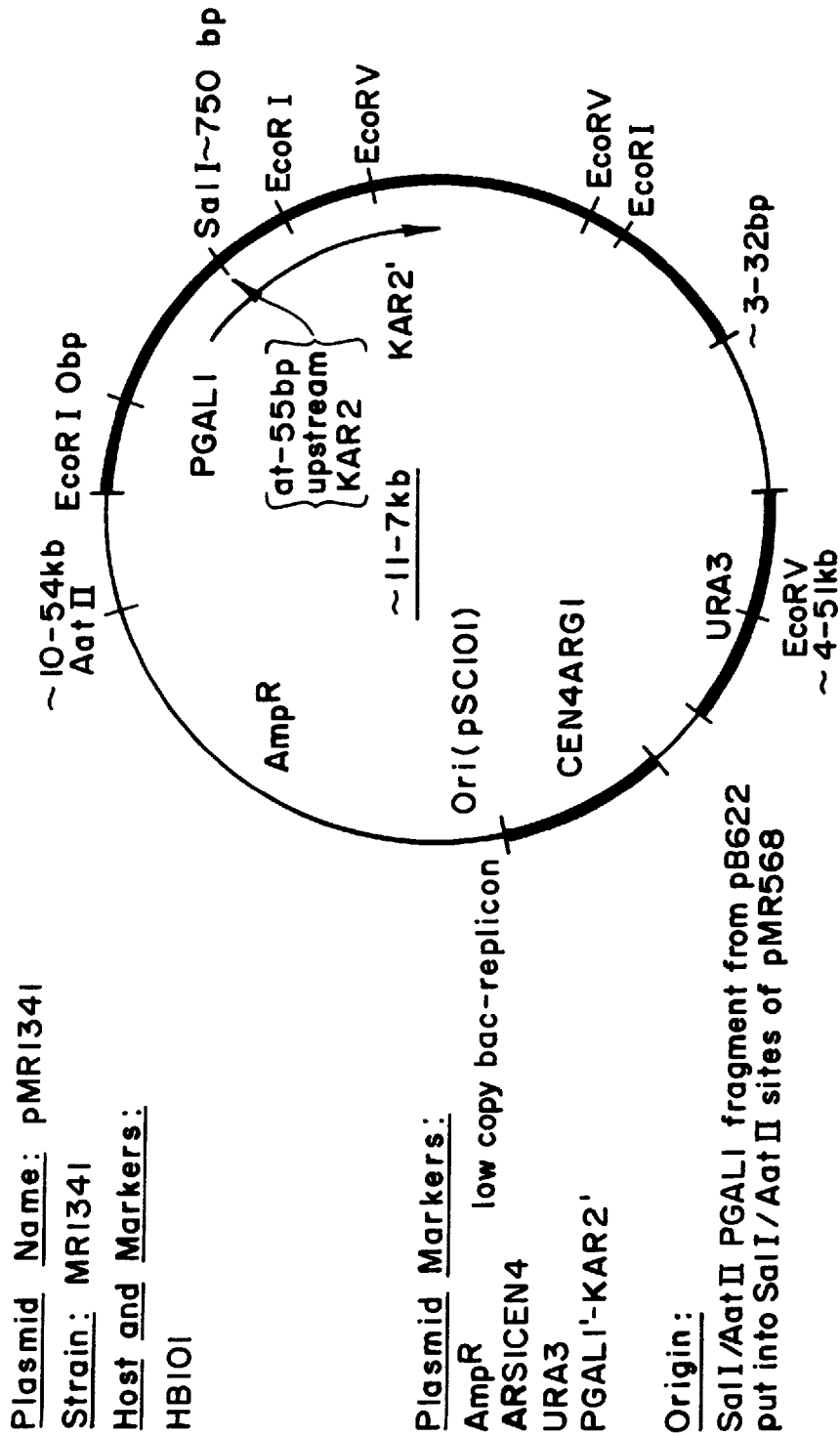

FIG. 2 depicts this pMR1341 expression vector for KAR2. As depicted, this vector encodes a pSC101 2origin of replication (ori pSC101) and an ampicillin resistance (Amp$^R$) which permit replication and selection of pMR1341 in Escherichia coli. pMR1341 further encodes a yeast centromeric (CEN4) sequence and a yeast autonomous replication sequence-1 (ARS1) which permit autonomous replication in yeast host cells. Vogel et al. (1990) describe this vector in greater detail.

EXAMPLE 3

Increased Secretion of Overexpressed Proteins Upon Expression of a Chaperone Protein The KAR2 yeast chaperone coding region was placed under the control of a galactose inducible promoter and the plasmid encoding this chimeric gene was transformed into BJ5464 yeast cells which also carried a plasmid encoding erythropoietin (EPO) under a galactose inducible promoter. These BJ5464 cells were then grown overnight in protein-free glucose medium in the absence of galactose. Expression of KAR2 and EPO proteins was induced by transfer of the BJ5464 cells into a galactose medium (SC GAL).

Cell growth after induction was monitored by observing the optical absorption of the culture at 600 nm. Cell and supernatant samples were taken at 24, 48 and 72 hours after induction. Cell samples were used for determination of KAR2 protein levels using the slot blot procedure described in Example 1. Supernatant samples were tested for the amount of secreted EPO by using the slot blot procedure with a SY14 monoclonal antibody which is specific for EPO.

Figure 3:
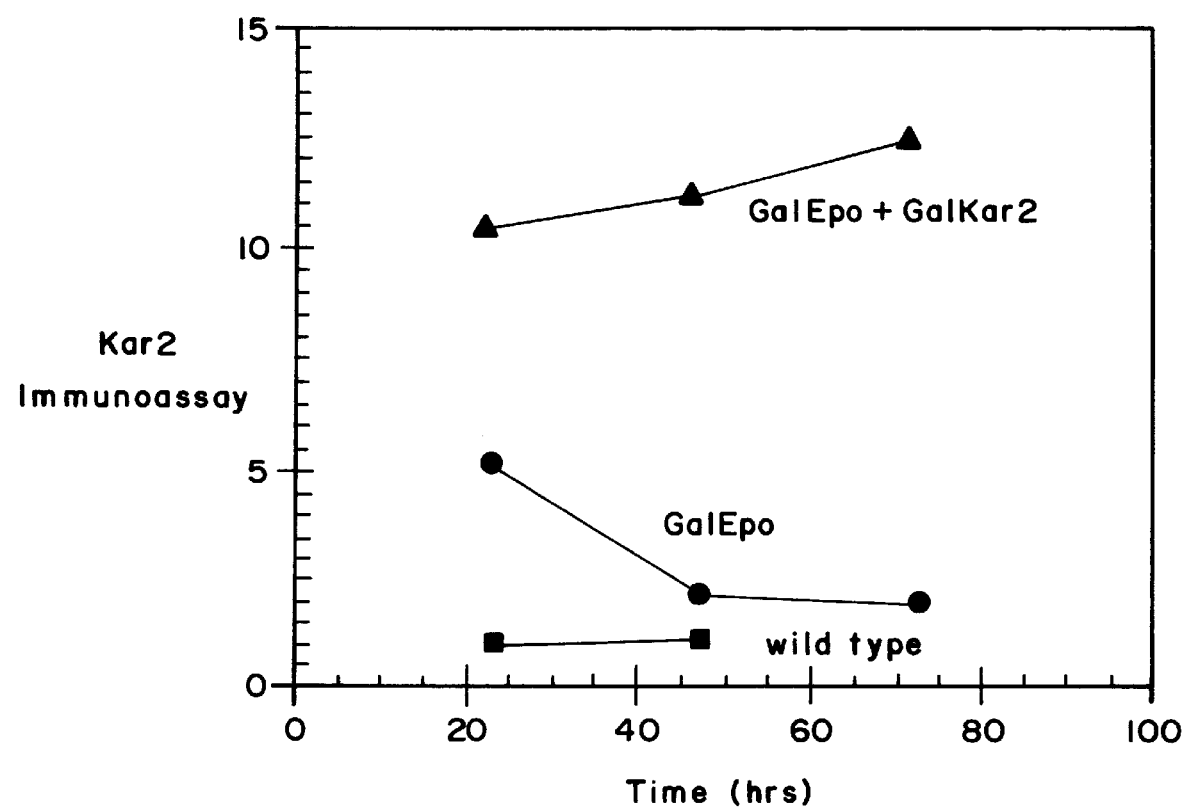

FIG. 3 depicts the KAR2 expression observed in cell extracts collected at 24, 48 and 72 hours after induction. The KAR2 immunoassay values provided in FIG. 3 represent a ratio of the amount of KAR2 detected in a given yeast cell type relative to wild type yeast. KAR2 expression in wild type cells (■), cells transformed with the EPO-encoding plasmid only (●, GalEpo) and cells transformed with both the EPO-encoding plasmid and the KAR2-encoding plasmid (▲, GalEpo+GalKar2), is depicted. After induction, expression of KAR2 is initially higher in cells with the EPO-encoding plasmid than in wild type yeast cells. However, GalEpo cellular expression of KAR2 drops to almost wild type levels by 48 hours after induction. If KAR2 expression were monitored for longer periods of time, the amount of KAR2 in the GalEPO cells would be less than wild type, as shown in FIG. 1. However, KAR2 expression at 24 hr is significantly greater in GalEpo+GalKAR2 cells which have the KAR2-encoding plasmid despite the presence of overexpressed EPO. Moreover, by 48 to 72 hours after induction, KAR2 expression is at least 4- to 5-fold higher in cells expressing additional amounts of KAR2 recombinantly than in cells expressing KAR2 from a native, genomic locus. Therefore, KAR2 expression can be boosted significantly by recombinant expression.

Figure 4:
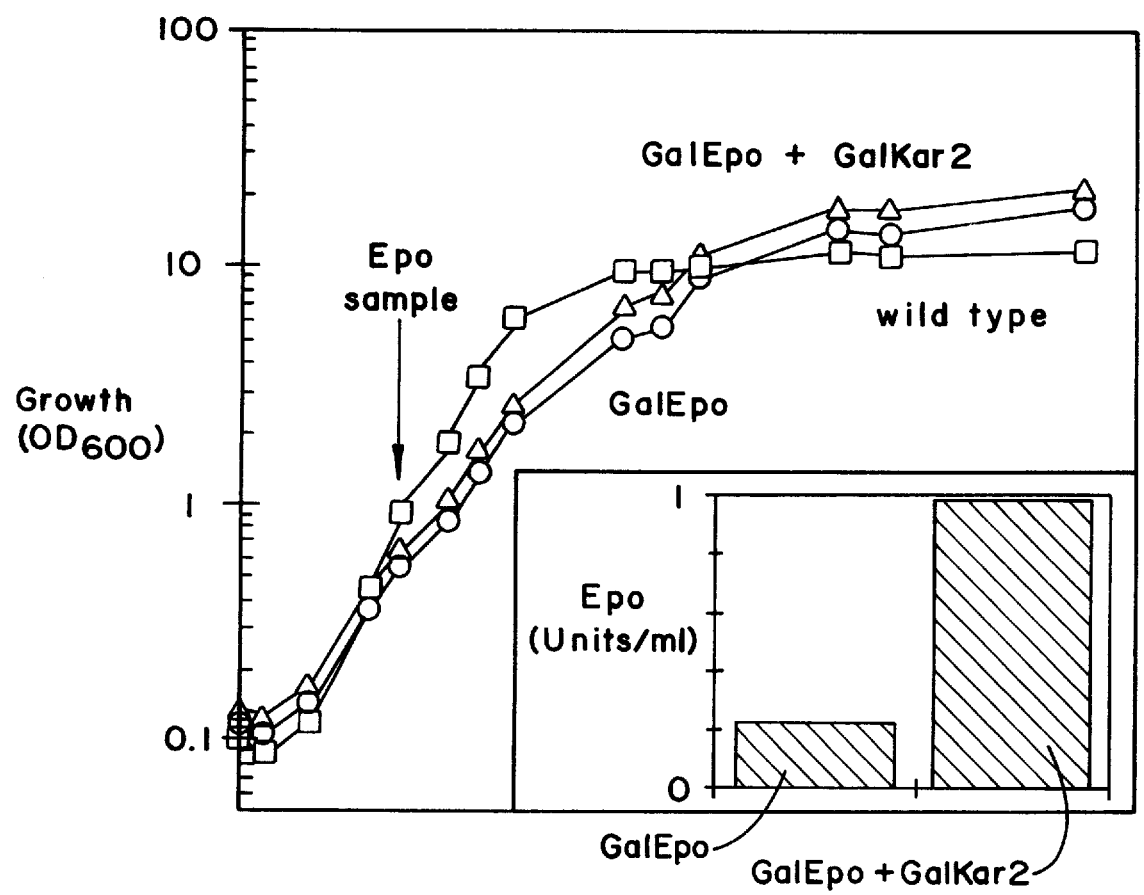

FIG. 4 depicts the growth of wild type cells (□), cells transformed with the EPO-encoding plasmid only (○, GalEpo) and cells transformed with both the EPO-encoding plasmid and the KAR2-encoding plasmid (Δ, GalEpo+GalKar2) after induction of EPO and KAR2 expression.

The inset provided in FIG. 4 depicts the amount of EPO secreted into the medium of cells which have the EPO-encoding plasmid only (GalEpo) compared with the amount of secreted EPO from cells having both the EPO-encoding plasmid and the KAR2-encoding plasmid (GalEpo+GalKar2). The supernatants tested were collected during exponential growth of these yeast strains at the indicated time point (arrow). As shown in the FIG. 4 inset, the amount of EPO secreted upon induction of KAR2 expression is almost five-fold higher than when no additional KAR2 chaperone protein is present.

Therefore, increasing KAR2 expression causes a substantial increase in protein secretion.

EXAMPLE 4

Construction of Strains Overexpressing BiP and PDI

Yeast strains were constructed which overexpress yeast BiP, PDI or both BiP and PDI.

The overexpression system for BiP utilizes the glyceraldehyde-3-phosphate dehydrogenase (GPD) constitutive promoter. A SalI-AatII fragment containing the GPD promoter was ligated into the AatII-SalI site of the pMRI341 expression vector described in Example 2, replacing the galactose (GAL1) promoter used for inducible expression of yeast BiP. A single-copy centromere plasmid containing this construct was named pGPDKAR2. BJ5464 cells were transformed with pGPDKAR2.

To construct a yeast strain that overexpresses yeast PDI, an expression cassette containing the yeast PDI gene downstream of the constitutive ADHII promoter was integrated into the chromosomal copy of PDI using LEU2 as a selective marker. Yeast strain BJ5464 with this integrated PDI expression cassette was renamed YVH10 (PDI::ADHII-PDI-Leu2 ura3–52 trp 1 leu2Δ1 his 3Δ200 pep4::H153 prb 1Δ1.6p can 1 GAL).

YVH10 cells were transformed with pGPDKAR2 to provide cells overexpressing both BiP and PDI.

Cells extracts from mid-exponential phase cultures of BJ5464, BJ5464 transformed with pGPDKAR2, YVH10, and YVH10 transformed with pGPDKAR2 were prepared. Yeast BiP and PDI were detected by chemiluminescence using α-Kar21gG and α-PDI1gG, respectively. Densitometry was performed with an Apple Optical Scanner and analyzed with the program Image (NIH). Quantitation of band intensity was determined from three dilutions of protein and multiple time exposures of the bands within the linear range of the film.

As demonstrated in Table 3, BiP was overexpressed approximately 5–6 fold, and PDI was overexpressed approximately 11–16 fold.

TABLE 3

|  | BJ5464 | BJ5464 + pGFDKAR2 | YVH10 | YVH10 + GPDKAR2 |
| --- | --- | --- | --- | --- |
| BiP overexpressed | − | + | − | + |
| PDI overexpressed | − | − | + | + |
| Densitometry scan, αBiP | 1 | 5.9 | 1.3 | 5.5 |
| Densitometry scan, αPDI | 1.3 | 1 | 16 | 11 |

EXAMPLE 5

Increased Secretion of Overexpressed Proteins Upon Expression of a Chaperone Protein The four yeast strains described in Example 4 (BJ5464, BJ5464+pGPDKAR2, YVH10, and YVH10+pGPDKAR2) are grown for several generations in synthetic complete (S.C.) media to provide strains which overexpress neither BiP nor PDI, BiP alone, PDI alone, or both BiP and PDI, respectively. The strains are each transformed with an expression vector which directs the constitutive expression of a gene product. Supernatant samples are collected during exponential growth of the transformed cells and assayed for the presence of the secreted gene product.

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 2780 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 285..2333

( x i ) SEQUENCE DESCRIPTION: SEQ ID NO:1:

```
CTCGAGCAAA  GTGTAGATCC  CATTAGGACT  CATCATTCAT  CTAATTTTGC  TATGTTAGCT          60

GCAACTTTCT  ATTTTAATAG  AACCTTCTGG  AAATTTCACC  CGGCGCGGCA  CCCGAGGAAC         120

TGGACAGCGT  GTCGAAAAAG  TTGCTTTTTT  ATATAAAGGA  CACGAAAAGG  GTTCTCTGGA         180

AGATATAAAT  ATGGCTATGT  AATTCTAAAG  ATTAACGTGT  TACTGTTTTA  CTTTTTTAAA         240

GTCCCCAAGA  GTAGTCTCAA  GGGAAAAAGC  GTATCAAACA  TACC ATG TTT TTC AAC          296
                                                   Met Phe Phe Asn
                                                     1

AGA CTA AGC GCT GGC AAG CTG CTG GTA CCA CTC TCC GTG GTC CTG TAC              344
Arg Leu Ser Ala Gly Lys Leu Leu Val Pro Leu Ser Val Val Leu Tyr
  5              10                  15                  20

GCC CTT TTC GTG GTA ATA TTA CCT TTA CAG AAT TCT TTC CAC TCC TCC              392
Ala Leu Phe Val Val Ile Leu Pro Leu Gln Asn Ser Phe His Ser Ser
                  25                  30                  35

AAT GTT TTA GTT AGA GGT GCC GAT GAT GTA GAA AAC TAC GGA ACT GTT              440
Asn Val Leu Val Arg Gly Ala Asp Asp Val Glu Asn Tyr Gly Thr Val
              40                  45                  50

ATC GGT ATT GAC TTA GGT ACT ACT TAT TCC TGT GTT GCT GTG ATG AAA              488
Ile Gly Ile Asp Leu Gly Thr Thr Tyr Ser Cys Val Ala Val Met Lys
          55                  60                  65

AAT GGT AAG ACT GAA ATT CTT GCT AAT GAG CAA GGT AAC AGA ATC ACC              536
Asn Gly Lys Thr Glu Ile Leu Ala Asn Glu Gln Gly Asn Arg Ile Thr
      70                  75                  80

CCA TCT TAC GTG GCA TTC ACC GAT GAT GAA AGA TTG ATT GGT GAT GCT              584
Pro Ser Tyr Val Ala Phe Thr Asp Asp Glu Arg Leu Ile Gly Asp Ala
 85                  90                  95                 100

GCA AAG AAC CAA GTT GCT GCC AAT CCT CAA AAC ACC ATC TTC GAC ATT              632
Ala Lys Asn Gln Val Ala Ala Asn Pro Gln Asn Thr Ile Phe Asp Ile
                 105                 110                 115

AAG AGA TTG ATC GGT TTG AAA TAT AAC GAC AGA TCT GTT CAG AAG GAT              680
Lys Arg Leu Ile Gly Leu Lys Tyr Asn Asp Arg Ser Val Gln Lys Asp
             120                 125                 130

ATC AAG CAC TTG CCA TTT AAT GTG GTT AAT AAA GAT GGG AAG CCC GCT              728
Ile Lys His Leu Pro Phe Asn Val Val Asn Lys Asp Gly Lys Pro Ala
         135                 140                 145

GTA GAA GTA AGT GTC AAA GGA GAA AAG AAG GTT TTT ACT CCA GAA GAA              776
Val Glu Val Ser Val Lys Gly Glu Lys Lys Val Phe Thr Pro Glu Glu
     150                 155                 160

ATT TCT GGT ATG ATC TTG GGT AAG ATG AAA CAA ATT GCC GAA GAT TAT              824
Ile Ser Gly Met Ile Leu Gly Lys Met Lys Gln Ile Ala Glu Asp Tyr
165                 170                 175                 180
```

| | | | | | | | | | | | | | | | | |
|---|---|---|---|---|---|---|---|---|---|---|---|---|---|---|---|---|
| TTA | GGC | ACT | AAG | GTT | ACC | CAT | GCT | GTC | GTT | ACT | GTT | CCT | GCT | TAT | TTC | 872 |
| Leu | Gly | Thr | Lys | Val | Thr | His | Ala | Val | Val | Thr | Val | Pro | Ala | Tyr | Phe | |
| | | | | 185 | | | | 190 | | | | | | 195 | | |
| AAT | GAC | GCG | CAA | AGA | CAA | GCC | ACC | AAG | GAT | GCT | GGT | ACC | ATC | GCT | GGT | 920 |
| Asn | Asp | Ala | Gln | Arg | Gln | Ala | Thr | Lys | Asp | Ala | Gly | Thr | Ile | Ala | Gly | |
| | | | 200 | | | | 205 | | | | 210 | | | | | |
| TTG | AAC | GTT | TTG | AGA | ATT | GTT | AAT | GAA | CCA | ACC | GCA | GCC | GCC | ATT | GCC | 968 |
| Leu | Asn | Val | Leu | Arg | Ile | Val | Asn | Glu | Pro | Thr | Ala | Ala | Ala | Ile | Ala | |
| | | 215 | | | | 220 | | | | | 225 | | | | | |
| TAC | GGT | TTG | GAT | AAA | TCT | GAT | AAG | GAA | CAT | CAA | ATT | ATT | GTT | TAT | GAT | 1016 |
| Tyr | Gly | Leu | Asp | Lys | Ser | Asp | Lys | Glu | His | Gln | Ile | Ile | Val | Tyr | Asp | |
| | 230 | | | | 235 | | | | 240 | | | | | | | |
| TTG | GGT | GGT | GGT | ACT | TTC | GAT | GTC | TCT | CTA | TTG | TCT | ATT | GAA | AAC | GGT | 1064 |
| Leu | Gly | Gly | Gly | Thr | Phe | Asp | Val | Ser | Leu | Leu | Ser | Ile | Glu | Asn | Gly | |
| 245 | | | | 250 | | | | | 255 | | | | | | 260 | |
| GTT | TTC | GAA | GTC | CAA | GCC | ACT | TCT | GGT | GAT | ACT | CAT | TTA | GGT | GGT | GAA | 1112 |
| Val | Phe | Glu | Val | Gln | Ala | Thr | Ser | Gly | Asp | Thr | His | Leu | Gly | Gly | Glu | |
| | | | | 265 | | | | | 270 | | | | | | 275 | |
| GAT | TTT | GAC | TAT | AAG | ATC | GTT | CGT | CAA | TTG | ATA | AAA | GCT | TTC | AAG | AAG | 1160 |
| Asp | Phe | Asp | Tyr | Lys | Ile | Val | Arg | Gln | Leu | Ile | Lys | Ala | Phe | Lys | Lys | |
| | | | 280 | | | | | 285 | | | | | 290 | | | |
| AAG | CAT | GGT | ATT | GAT | GTG | TCT | GAC | AAC | AAC | AAG | GCC | CTA | GCT | AAA | TTG | 1208 |
| Lys | His | Gly | Ile | Asp | Val | Ser | Asp | Asn | Asn | Lys | Ala | Leu | Ala | Lys | Leu | |
| | | 295 | | | | | 300 | | | | | 305 | | | | |
| AAG | AGA | GAA | GCT | GAA | AAG | GCT | AAA | CGT | GCC | TTG | TCC | AGC | CAA | ATG | TCC | 1256 |
| Lys | Arg | Glu | Ala | Glu | Lys | Ala | Lys | Arg | Ala | Leu | Ser | Ser | Gln | Met | Ser | |
| | 310 | | | | | 315 | | | | | 320 | | | | | |
| ACC | CGT | ATT | GAA | ATT | GAC | TCC | TTC | GTT | GAT | GGT | ATC | GAC | TTA | AGT | GAA | 1304 |
| Thr | Arg | Ile | Glu | Ile | Asp | Ser | Phe | Val | Asp | Gly | Ile | Asp | Leu | Ser | Glu | |
| 325 | | | | | 330 | | | | | 335 | | | | | 340 | |
| ACC | TTG | ACC | AGA | GCT | AAG | TTT | GAG | GAA | TTA | AAC | CTA | GAT | CTA | TTC | AAG | 1352 |
| Thr | Leu | Thr | Arg | Ala | Lys | Phe | Glu | Glu | Leu | Asn | Leu | Asp | Leu | Phe | Lys | |
| | | | | 345 | | | | | 350 | | | | | 355 | | |
| AAG | ACC | TTG | AAG | CCT | GTC | GAG | AAG | GTT | TTG | CAA | GAT | TCT | GGT | TTG | GAA | 1400 |
| Lys | Thr | Leu | Lys | Pro | Val | Glu | Lys | Val | Leu | Gln | Asp | Ser | Gly | Leu | Glu | |
| | | | 360 | | | | | 365 | | | | | 370 | | | |
| AAG | AAG | GAT | GTT | GAT | GAT | ATC | GTT | TTG | GTT | GGT | GGT | TCT | ACT | AGA | ATT | 1448 |
| Lys | Lys | Asp | Val | Asp | Asp | Ile | Val | Leu | Val | Gly | Gly | Ser | Thr | Arg | Ile | |
| | | 375 | | | | | 380 | | | | | 385 | | | | |
| CCA | AAG | GTC | CAA | CAA | TTG | TTA | GAA | TCA | TAC | TTT | GAT | GGT | AAG | AAG | GCC | 1496 |
| Pro | Lys | Val | Gln | Gln | Leu | Leu | Glu | Ser | Tyr | Phe | Asp | Gly | Lys | Lys | Ala | |
| | 390 | | | | | 395 | | | | | 400 | | | | | |
| TCC | AAG | GGT | ATT | AAC | CCA | GAT | GAA | GCT | GTT | GCA | TAC | GGT | GCA | GCC | GTT | 1544 |
| Ser | Lys | Gly | Ile | Asn | Pro | Asp | Glu | Ala | Val | Ala | Tyr | Gly | Ala | Ala | Val | |
| 405 | | | | | 410 | | | | | 415 | | | | | 420 | |
| CAA | GCT | GGT | GTC | TTA | TCC | GGT | GAA | GAA | GGT | GTC | GAA | GAT | ATT | GTT | TTA | 1592 |
| Gln | Ala | Gly | Val | Leu | Ser | Gly | Glu | Glu | Gly | Val | Glu | Asp | Ile | Val | Leu | |
| | | | | 425 | | | | | 430 | | | | | 435 | | |
| TTG | GAT | GTC | AAC | GCT | TTG | ACT | CTT | GGT | ATT | GAA | ACC | ACT | GGT | GGT | GTC | 1640 |
| Leu | Asp | Val | Asn | Ala | Leu | Thr | Leu | Gly | Ile | Glu | Thr | Thr | Gly | Gly | Val | |
| | | | 440 | | | | | 445 | | | | | 450 | | | |
| ATG | ACT | CCA | TTA | ATT | AAG | AGA | AAT | ACT | GCT | ATT | CCT | ACA | AAG | AAA | TCC | 1688 |
| Met | Thr | Pro | Leu | Ile | Lys | Arg | Asn | Thr | Ala | Ile | Pro | Thr | Lys | Lys | Ser | |
| | | 455 | | | | | 460 | | | | | 465 | | | | |
| CAA | ATT | TTC | TCT | ACT | GCC | GTT | GAC | AAC | CAA | CCA | ACC | GTT | ATG | ATC | AAG | 1736 |
| Gln | Ile | Phe | Ser | Thr | Ala | Val | Asp | Asn | Gln | Pro | Thr | Val | Met | Ile | Lys | |
| | | 470 | | | | | 475 | | | | | 480 | | | | |
| GTA | TAC | GAG | GGT | GAA | AGA | GCC | ATG | TCT | AAG | GAC | AAC | AAT | CTA | TTA | GGT | 1784 |
| Val | Tyr | Glu | Gly | Glu | Arg | Ala | Met | Ser | Lys | Asp | Asn | Asn | Leu | Leu | Gly | |
| 485 | | | | | 490 | | | | | 495 | | | | | 500 | |

| AAG | TTT | GAA | TTA | ACC | GGC | ATT | CCA | CCA | GCA | CCA | AGA | GGT | GTA | CCT | CAA | 1832 |
| Lys | Phe | Glu | Leu | Thr | Gly | Ile | Pro | Pro | Ala | Pro | Arg | Gly | Val | Pro | Gln | |
| | | | | 505 | | | | | 510 | | | | | 515 | | |

| ATT | GAA | GTC | ACA | TTT | GCA | CTT | GAC | GCT | AAT | GGT | ATT | CTG | AAG | GTG | TCT | 1880 |
| Ile | Glu | Val | Thr | Phe | Ala | Leu | Asp | Ala | Asn | Gly | Ile | Leu | Lys | Val | Ser | |
| | | | 520 | | | | | 525 | | | | | 530 | | | |

| GCC | ACA | GAT | AAG | GGA | ACT | GGT | AAA | TCC | GAA | TCT | ATC | ACC | ATC | ACT | AAC | 1928 |
| Ala | Thr | Asp | Lys | Gly | Thr | Gly | Lys | Ser | Glu | Ser | Ile | Thr | Ile | Thr | Asn | |
| | | 535 | | | | | 540 | | | | | 545 | | | | |

| GAT | AAA | GGT | AGA | TTA | ACC | CAA | GAA | GAG | ATT | GAT | AGA | ATG | GTT | GAA | GAG | 1976 |
| Asp | Lys | Gly | Arg | Leu | Thr | Gln | Glu | Glu | Ile | Asp | Arg | Met | Val | Glu | Glu | |
| | 550 | | | | | 555 | | | | | 560 | | | | | |

| GCT | GAA | AAA | TTC | GCT | TCT | GAA | GAC | GCT | TCT | ATC | AAG | GCC | AAG | GTT | GAA | 2024 |
| Ala | Glu | Lys | Phe | Ala | Ser | Glu | Asp | Ala | Ser | Ile | Lys | Ala | Lys | Val | Glu | |
| 565 | | | | | 570 | | | | | 575 | | | | | 580 | |

| TCT | AGA | AAC | AAA | TTA | GAA | AAC | TAC | GCT | CAC | TCT | TTG | AAA | AAC | CAA | GTT | 2072 |
| Ser | Arg | Asn | Lys | Leu | Glu | Asn | Tyr | Ala | His | Ser | Leu | Lys | Asn | Gln | Val | |
| | | | | 585 | | | | | 590 | | | | | 595 | | |

| AAT | GGT | GAC | CTA | GGT | GAA | AAA | TTG | GAA | GAA | GAA | GAC | AAG | GAA | ACC | TTA | 2120 |
| Asn | Gly | Asp | Leu | Gly | Glu | Lys | Leu | Glu | Glu | Glu | Asp | Lys | Glu | Thr | Leu | |
| | | | 600 | | | | | 605 | | | | | 610 | | | |

| TTA | GAT | GCT | GCT | AAC | GAT | GTT | TTA | GAA | TGG | TTA | GAT | GAT | AAC | TTT | GAA | 2168 |
| Leu | Asp | Ala | Ala | Asn | Asp | Val | Leu | Glu | Trp | Leu | Asp | Asp | Asn | Phe | Glu | |
| | | 615 | | | | | 620 | | | | | 625 | | | | |

| ACC | GCC | ATT | GCT | GAA | GAC | TTT | GAT | GAA | AAG | TTC | GAA | TCT | TTG | TCC | AAG | 2216 |
| Thr | Ala | Ile | Ala | Glu | Asp | Phe | Asp | Glu | Lys | Phe | Glu | Ser | Leu | Ser | Lys | |
| | 630 | | | | | 635 | | | | | 640 | | | | | |

| GTC | GCT | TAT | CCA | ATT | ACT | TCT | AAG | TTG | TAC | GGA | GGT | GCT | GAT | GGT | TCT | 2264 |
| Val | Ala | Tyr | Pro | Ile | Thr | Ser | Lys | Leu | Tyr | Gly | Gly | Ala | Asp | Gly | Ser | |
| 645 | | | | | 650 | | | | | 655 | | | | | 660 | |

| GGT | GCC | GCT | GAT | TAT | GAC | GAC | GAA | GAT | GAA | GAT | GAC | GAT | GGT | GAT | TAT | 2312 |
| Gly | Ala | Ala | Asp | Tyr | Asp | Asp | Glu | Asp | Glu | Asp | Asp | Asp | Gly | Asp | Tyr | |
| | | | | 665 | | | | | 670 | | | | | 675 | | |

| TTC | GAA | CAC | GAC | GAA | TTG | TAGATAAAAT | AGTTAAAAAT | TTTTGCTGCT | | | | | | | | 2360 |
| Phe | Glu | His | Asp | Glu | Leu | | | | | | | | | | | |
| | | | 680 | | | | | | | | | | | | | |

| GGAAGCTTCA | AGGTTGTTAA | TTTATTGACT | TGCATAGAAT | ATCTACATTT | CTTCTAAAAA | 2420 |
| TACATGCATA | GCTAATTCAA | ACTTCGAGCT | TCATACAATT | TTCGAGGAGA | TTATACTGAG | 2480 |
| TATATACGTA | AATATATGCA | TTATATGTTA | TAAAATTAGA | AAGATATAGA | AATTTCATTG | 2540 |
| AAGAGTATAG | AGACTGGGGT | TAAGGTACTC | AGTAACAGTG | TCATCAATAT | GCTAATTTTG | 2600 |
| CGTATTACTT | AGCTCTATTG | CGCAAATGCA | ATTTTTCTT | ACCCTGATAA | TGCTTTATTT | 2660 |
| CCCGTTCCGA | AAATTTTTCA | CTGAAAAAAA | AGTGCTTAAG | CTCATCTCAT | CTCATCTCAT | 2720 |
| CCCATCACTA | TTGAAATATT | TTGCTAAAAC | ATTATAACAG | AGAGAGTTGA | AAGGCTCGAG | 2780 |

( 2 ) INFORMATION FOR SEQ ID NO:2:

( i ) SEQUENCE CHARACTERISTICS:
        ( A ) LENGTH: 682 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Phe | Phe | Asn | Arg | Leu | Ser | Ala | Gly | Lys | Leu | Leu | Val | Pro | Leu | Ser |
| 1 | | | | 5 | | | | | 10 | | | | | 15 | |

| Val | Val | Leu | Tyr | Ala | Leu | Phe | Val | Val | Ile | Leu | Pro | Leu | Gln | Asn | Ser |
| | | | 20 | | | | | 25 | | | | | 30 | | |

```
Phe His Ser Ser Asn Val Leu Val Arg Gly Ala Asp Asp Val Glu Asn
        35                  40                  45
Tyr Gly Thr Val Ile Gly Ile Asp Leu Gly Thr Thr Tyr Ser Cys Val
    50                  55                  60
Ala Val Met Lys Asn Gly Lys Thr Glu Ile Leu Ala Asn Glu Gln Gly
65                  70                  75                  80
Asn Arg Ile Thr Pro Ser Tyr Val Ala Phe Thr Asp Asp Glu Arg Leu
                85                  90                  95
Ile Gly Asp Ala Ala Lys Asn Gln Val Ala Ala Asn Pro Gln Asn Thr
                100                 105                 110
Ile Phe Asp Ile Lys Arg Leu Ile Gly Leu Lys Tyr Asn Asp Arg Ser
            115                 120                 125
Val Gln Lys Asp Ile Lys His Leu Pro Phe Asn Val Val Asn Lys Asp
    130                 135                 140
Gly Lys Pro Ala Val Glu Val Ser Val Lys Gly Glu Lys Lys Val Phe
145                 150                 155                 160
Thr Pro Glu Glu Ile Ser Gly Met Ile Leu Gly Lys Met Lys Gln Ile
                165                 170                 175
Ala Glu Asp Tyr Leu Gly Thr Lys Val Thr His Ala Val Val Thr Val
            180                 185                 190
Pro Ala Tyr Phe Asn Asp Ala Gln Arg Gln Ala Thr Lys Asp Ala Gly
        195                 200                 205
Thr Ile Ala Gly Leu Asn Val Leu Arg Ile Val Asn Glu Pro Thr Ala
    210                 215                 220
Ala Ala Ile Ala Tyr Gly Leu Asp Lys Ser Asp Lys Glu His Gln Ile
225                 230                 235                 240
Ile Val Tyr Asp Leu Gly Gly Gly Thr Phe Asp Val Ser Leu Leu Ser
                245                 250                 255
Ile Glu Asn Gly Val Phe Glu Val Gln Ala Thr Ser Gly Asp Thr His
            260                 265                 270
Leu Gly Gly Glu Asp Phe Asp Tyr Lys Ile Val Arg Gln Leu Ile Lys
        275                 280                 285
Ala Phe Lys Lys Lys His Gly Ile Asp Val Ser Asp Asn Asn Lys Ala
    290                 295                 300
Leu Ala Lys Leu Lys Arg Glu Ala Glu Lys Ala Lys Arg Ala Leu Ser
305                 310                 315                 320
Ser Gln Met Ser Thr Arg Ile Glu Ile Asp Ser Phe Val Asp Gly Ile
                325                 330                 335
Asp Leu Ser Glu Thr Leu Thr Arg Ala Lys Phe Glu Glu Leu Asn Leu
            340                 345                 350
Asp Leu Phe Lys Lys Thr Leu Lys Pro Val Glu Lys Val Leu Gln Asp
        355                 360                 365
Ser Gly Leu Glu Lys Lys Asp Val Asp Asp Ile Val Leu Val Gly Gly
    370                 375                 380
Ser Thr Arg Ile Pro Lys Val Gln Gln Leu Leu Glu Ser Tyr Phe Asp
385                 390                 395                 400
Gly Lys Lys Ala Ser Lys Gly Ile Asn Pro Asp Glu Ala Val Ala Tyr
                405                 410                 415
Gly Ala Ala Val Gln Ala Gly Val Leu Ser Gly Glu Glu Gly Val Glu
            420                 425                 430
Asp Ile Val Leu Leu Asp Val Asn Ala Leu Thr Leu Gly Ile Glu Thr
        435                 440                 445
Thr Gly Gly Val Met Thr Pro Leu Ile Lys Arg Asn Thr Ala Ile Pro
    450                 455                 460
```

| | | | | | | | | | | | | | | |
|---|---|---|---|---|---|---|---|---|---|---|---|---|---|---|
| Thr | Lys | Lys | Ser | Gln | Ile | Phe | Ser | Thr | Ala | Val | Asp | Asn | Gln | Pro | Thr |
| 465 | | | | | 470 | | | | 475 | | | | | 480 |
| Val | Met | Ile | Lys | Val | Tyr | Glu | Gly | Glu | Arg | Ala | Met | Ser | Lys | Asp | Asn |
| | | | | 485 | | | | | 490 | | | | | 495 | |
| Asn | Leu | Leu | Gly | Lys | Phe | Glu | Leu | Thr | Gly | Ile | Pro | Pro | Ala | Pro | Arg |
| | | | 500 | | | | | 505 | | | | | 510 | | |
| Gly | Val | Pro | Gln | Ile | Glu | Val | Thr | Phe | Ala | Leu | Asp | Ala | Asn | Gly | Ile |
| | | 515 | | | | | 520 | | | | | 525 | | | |
| Leu | Lys | Val | Ser | Ala | Thr | Asp | Lys | Gly | Thr | Gly | Lys | Ser | Glu | Ser | Ile |
| | 530 | | | | | 535 | | | | 540 | | | | | |
| Thr | Ile | Thr | Asn | Asp | Lys | Gly | Arg | Leu | Thr | Gln | Glu | Glu | Ile | Asp | Arg |
| 545 | | | | | 550 | | | | | 555 | | | | | 560 |
| Met | Val | Glu | Glu | Ala | Glu | Lys | Phe | Ala | Ser | Glu | Asp | Ala | Ser | Ile | Lys |
| | | | | 565 | | | | | 570 | | | | | 575 | |
| Ala | Lys | Val | Glu | Ser | Arg | Asn | Lys | Leu | Glu | Asn | Tyr | Ala | His | Ser | Leu |
| | | | 580 | | | | | 585 | | | | | 590 | | |
| Lys | Asn | Gln | Val | Asn | Gly | Asp | Leu | Gly | Glu | Lys | Leu | Glu | Glu | Glu | Asp |
| | | 595 | | | | | 600 | | | | | 605 | | | |
| Lys | Glu | Thr | Leu | Leu | Asp | Ala | Ala | Asn | Asp | Val | Leu | Glu | Trp | Leu | Asp |
| | 610 | | | | | 615 | | | | | 620 | | | | |
| Asp | Asn | Phe | Glu | Thr | Ala | Ile | Ala | Glu | Asp | Phe | Asp | Glu | Lys | Phe | Glu |
| 625 | | | | | 630 | | | | | 635 | | | | | 640 |
| Ser | Leu | Ser | Lys | Val | Ala | Tyr | Pro | Ile | Thr | Ser | Lys | Leu | Tyr | Gly | Gly |
| | | | | 645 | | | | | 650 | | | | | 655 | |
| Ala | Asp | Gly | Ser | Gly | Ala | Ala | Asp | Tyr | Asp | Asp | Glu | Asp | Glu | Asp | Asp |
| | | | 660 | | | | | 665 | | | | | 670 | | |
| Asp | Gly | Asp | Tyr | Phe | Glu | His | Asp | Glu | Leu | | | | | | |
| | | 675 | | | | | 680 | | | | | | | | |

( 2 ) INFORMATION FOR SEQ ID NO:3:

( i ) SEQUENCE CHARACTERISTICS:
        ( A ) LENGTH: 2367 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 251..2176

( x i ) SEQUENCE DESCRIPTION: SEQ ID NO:3:

```
AAGCTTTTAG GAATTTTGAA TTTTTGATCG AATTTTAGAA AAAACTATTC GCAAGACTAC         60

AATTTTTGAA GGGTGCTATT TGTGAAAAAA TAAAACGTGA AATAAATCGT TTTATAATTT        120

ACGAATTGTC GTTATTCAAA ACTCAAAAAA TATGATCTCG TCGAGATTCA CTAATGTAGT        180

CCGTAGCGGA TTGCGTTTCC AAAGCAAGGG AGCATCGTTC AAGATTGGCG CTTCCTTGCA        240

TGGAAGTCGC ATG ACC GCC CGC TGG AAT TCT AAT GCA AGT GGT AAT GAA          289
            Met Thr Ala Arg Trp Asn Ser Asn Ala Ser Gly Asn Glu
              1               5                  10

AAA GTT AAG GGT CCC GTA ATC GGT ATT GAC TTG GGT ACC ACC ACC TCA          337
Lys Val Lys Gly Pro Val Ile Gly Ile Asp Leu Gly Thr Thr Thr Ser
     15              20                  25

TGT TTA GCA ATC ATG GAG GGT CAA ACC CCT AAG GTT ATT GCA AAT GCC          385
Cys Leu Ala Ile Met Glu Gly Gln Thr Pro Lys Val Ile Ala Asn Ala
 30              35                  40                  45
```

| | | | | | | | | | | | | | | | | |
|---|---|---|---|---|---|---|---|---|---|---|---|---|---|---|---|---|
| GAG | GGT | ACC | CGT | ACC | ACA | CCA | TCT | GTC | GTC | GCA | TTT | ACC | AAA | GAT | GGC | 433 |
| Glu | Gly | Thr | Arg | Thr | Thr | Pro | Ser | Val | Val | Ala | Phe | Thr | Lys | Asp | Gly | |
| | | | 50 | | | | | 55 | | | | | | 60 | | |
| GAG | CGT | TTG | GTG | GGT | GTT | AGC | GCT | AAA | CGC | CAA | GCC | GTC | ATT | AAC | CCG | 481 |
| Glu | Arg | Leu | Val | Gly | Val | Ser | Ala | Lys | Arg | Gln | Ala | Val | Ile | Asn | Pro | |
| | | | 65 | | | | | 70 | | | | | | 75 | | |
| GAA | AAC | ACA | TTT | TTT | GCT | ACT | AAG | CGT | TTA | ATC | GGT | CGT | AGA | TTT | AAA | 529 |
| Glu | Asn | Thr | Phe | Phe | Ala | Thr | Lys | Arg | Leu | Ile | Gly | Arg | Arg | Phe | Lys | |
| | | 80 | | | | | 85 | | | | | 90 | | | | |
| GAG | CCT | GAA | GTC | CAA | CGT | GAT | ATT | AAG | GAA | GTT | CCT | TAC | AAA | ATT | GTC | 577 |
| Glu | Pro | Glu | Val | Gln | Arg | Asp | Ile | Lys | Glu | Val | Pro | Tyr | Lys | Ile | Val | |
| | 95 | | | | | 100 | | | | | 105 | | | | | |
| GAG | CAC | TCA | AAT | GGA | GAT | GCT | TGG | TTG | GAG | GCT | CGT | GGT | AAG | ACC | TAC | 625 |
| Glu | His | Ser | Asn | Gly | Asp | Ala | Trp | Leu | Glu | Ala | Arg | Gly | Lys | Thr | Tyr | |
| 110 | | | | | 115 | | | | | 120 | | | | | 125 | |
| TCT | CCA | TCT | CAA | ATC | GGT | GGT | TTC | ATC | CTT | AGT | AAG | ATG | AGG | GAA | ACT | 673 |
| Ser | Pro | Ser | Gln | Ile | Gly | Gly | Phe | Ile | Leu | Ser | Lys | Met | Arg | Glu | Thr | |
| | | | | 130 | | | | | 135 | | | | | 140 | | |
| GCC | AGC | ACC | TAC | CTT | GGA | AAA | GAT | GTA | AAG | AAT | GCC | GTT | GTT | ACT | GTT | 721 |
| Ala | Ser | Thr | Tyr | Leu | Gly | Lys | Asp | Val | Lys | Asn | Ala | Val | Val | Thr | Val | |
| | | | 145 | | | | | 150 | | | | | 155 | | | |
| CCT | GCT | TAC | TTC | AAT | GAC | TCT | CAG | CGT | CAA | GCT | ACC | AAG | GCT | GCT | GGT | 769 |
| Pro | Ala | Tyr | Phe | Asn | Asp | Ser | Gln | Arg | Gln | Ala | Thr | Lys | Ala | Ala | Gly | |
| | | | 160 | | | | | 165 | | | | | 170 | | | |
| GCC | ATT | GCT | GGT | TTG | AAT | GTT | TTG | CGT | GTC | GTC | AAC | GAG | CCT | ACT | GCC | 817 |
| Ala | Ile | Ala | Gly | Leu | Asn | Val | Leu | Arg | Val | Val | Asn | Glu | Pro | Thr | Ala | |
| | 175 | | | | | 180 | | | | | 185 | | | | | |
| GCC | GCT | TTG | GCT | TAT | GGT | TTG | GAC | AAG | AAG | AAT | GAT | GCC | ATC | GTC | GCA | 865 |
| Ala | Ala | Leu | Ala | Tyr | Gly | Leu | Asp | Lys | Lys | Asn | Asp | Ala | Ile | Val | Ala | |
| 190 | | | | | 195 | | | | | 200 | | | | | 205 | |
| GTT | TTC | GAT | TTG | GGT | GGT | GGT | ACT | TTT | GAT | ATT | TCT | ATT | TTG | GAG | TTA | 913 |
| Val | Phe | Asp | Leu | Gly | Gly | Gly | Thr | Phe | Asp | Ile | Ser | Ile | Leu | Glu | Leu | |
| | | | | 210 | | | | | 215 | | | | | 220 | | |
| AAC | AAT | GGT | GTT | TTT | GAG | GTT | AGA | AGT | ACC | AAC | GGT | GAC | ACT | CAT | TTG | 961 |
| Asn | Asn | Gly | Val | Phe | Glu | Val | Arg | Ser | Thr | Asn | Gly | Asp | Thr | His | Leu | |
| | | | 225 | | | | | 230 | | | | | 235 | | | |
| GGT | GGT | GAG | GAC | TTT | GAT | GTT | GCT | CTT | GTT | CGT | CAC | ATT | GTC | GAG | ACC | 1009 |
| Gly | Gly | Glu | Asp | Phe | Asp | Val | Ala | Leu | Val | Arg | His | Ile | Val | Glu | Thr | |
| | | 240 | | | | | 245 | | | | | 250 | | | | |
| TTT | AAG | AAG | AAT | GAG | GGT | TTG | GAC | TTG | AGC | AAG | GAC | CGT | CTC | GCC | GTT | 1057 |
| Phe | Lys | Lys | Asn | Glu | Gly | Leu | Asp | Leu | Ser | Lys | Asp | Arg | Leu | Ala | Val | |
| | 255 | | | | | 260 | | | | | 265 | | | | | |
| CAA | CGT | ATT | CGT | GAG | GCT | GCT | GAA | AAA | GCT | AAG | TGC | GAA | CTT | TCC | TCT | 1105 |
| Gln | Arg | Ile | Arg | Glu | Ala | Ala | Glu | Lys | Ala | Lys | Cys | Glu | Leu | Ser | Ser | |
| 270 | | | | | 275 | | | | | 280 | | | | | 285 | |
| CTT | TCC | AAG | ACT | GAT | ATC | AGT | CTT | CCT | TTC | ATT | ACT | GCG | GAT | GCT | ACT | 1153 |
| Leu | Ser | Lys | Thr | Asp | Ile | Ser | Leu | Pro | Phe | Ile | Thr | Ala | Asp | Ala | Thr | |
| | | | | 290 | | | | | 295 | | | | | 300 | | |
| GGC | CCT | AAG | CAT | ATT | AAC | ATG | GAA | ATC | TCT | CGT | GCT | CAA | TTT | GAG | AAA | 1201 |
| Gly | Pro | Lys | His | Ile | Asn | Met | Glu | Ile | Ser | Arg | Ala | Gln | Phe | Glu | Lys | |
| | | | 305 | | | | | 310 | | | | | 315 | | | |
| CTT | GTT | GAT | CCT | CTC | GTT | CGT | CGT | ACC | ATC | GAT | CCT | TGC | AAG | CGT | GCC | 1249 |
| Leu | Val | Asp | Pro | Leu | Val | Arg | Arg | Thr | Ile | Asp | Pro | Cys | Lys | Arg | Ala | |
| | | 320 | | | | | 325 | | | | | 330 | | | | |
| CTT | AAG | GAT | GCT | AAC | TTG | CAA | ACC | TCT | GAA | ATC | AAT | GAA | GTT | ATC | CTT | 1297 |
| Leu | Lys | Asp | Ala | Asn | Leu | Gln | Thr | Ser | Glu | Ile | Asn | Glu | Val | Ile | Leu | |
| | | 335 | | | | | 340 | | | | | 345 | | | | |
| GTC | GGT | GGT | ATG | ACT | CGT | ATG | CCT | CGT | GTT | GTC | GAA | ACT | GTC | AAG | AGT | 1345 |
| Val | Gly | Gly | Met | Thr | Arg | Met | Pro | Arg | Val | Val | Glu | Thr | Val | Lys | Ser | |
| 350 | | | | | 355 | | | | | 360 | | | | | 365 | |

| | | | | | | | | | | | | | | | | |
|---|---|---|---|---|---|---|---|---|---|---|---|---|---|---|---|---|
| ATC | TTC | AAG | CGT | GAA | CCC | GCT | AAG | TCC | GTC | AAC | CCT | GAT | GAA | GCT | GTT | 1393 |
| Ile | Phe | Lys | Arg | Glu | Pro | Ala | Lys | Ser | Val | Asn | Pro | Asp | Glu | Ala | Val | |
| | | | | 370 | | | | 375 | | | | | 380 | | | |
| GCC | ATT | GGT | GCT | GCT | ATT | CAA | GGT | GGT | GTC | TTG | TCT | GGC | CAT | GTT | AAG | 1441 |
| Ala | Ile | Gly | Ala | Ala | Ile | Gln | Gly | Gly | Val | Leu | Ser | Gly | His | Val | Lys | |
| | | | 385 | | | | | 390 | | | | | 395 | | | |
| GAC | CTT | GTT | CTT | TTG | GAT | GTC | ACC | CCC | TTG | TCC | CTC | GGT | ATC | GAG | ACT | 1489 |
| Asp | Leu | Val | Leu | Leu | Asp | Val | Thr | Pro | Leu | Ser | Leu | Gly | Ile | Glu | Thr | |
| | | 400 | | | | | 405 | | | | | 410 | | | | |
| TTG | GGC | GGT | GTT | TTC | ACT | CGT | TTG | ATC | AAC | CGT | AAC | ACT | ACC | ATT | CCT | 1537 |
| Leu | Gly | Gly | Val | Phe | Thr | Arg | Leu | Ile | Asn | Arg | Asn | Thr | Thr | Ile | Pro | |
| | | 415 | | | | 420 | | | | | 425 | | | | | |
| ACT | CGC | AAG | TCT | CAA | GTT | TTC | TCC | ACT | GCT | GCT | GAT | GGT | CAA | ACT | GCC | 1585 |
| Thr | Arg | Lys | Ser | Gln | Val | Phe | Ser | Thr | Ala | Ala | Asp | Gly | Gln | Thr | Ala | |
| 430 | | | | | 435 | | | | | 440 | | | | | 445 | |
| GTT | GAA | ATC | CGT | GTC | TTC | CAG | GGT | GAA | CGT | GAG | CTT | GTT | CGT | GAC | AAC | 1633 |
| Val | Glu | Ile | Arg | Val | Phe | Gln | Gly | Glu | Arg | Glu | Leu | Val | Arg | Asp | Asn | |
| | | | | 450 | | | | | 455 | | | | | 460 | | |
| AAA | TTA | ATT | GGC | AAC | TTC | CAA | CTT | ACT | GGC | ATT | GCT | CCT | GCA | CCT | AAG | 1681 |
| Lys | Leu | Ile | Gly | Asn | Phe | Gln | Leu | Thr | Gly | Ile | Ala | Pro | Ala | Pro | Lys | |
| | | | 465 | | | | | 470 | | | | | 475 | | | |
| GGT | CAA | CCT | CAG | ATT | GAG | GTT | TCT | TTT | GAT | GTT | GAT | GCC | GAT | GGC | ATT | 1729 |
| Gly | Gln | Pro | Gln | Ile | Glu | Val | Ser | Phe | Asp | Val | Asp | Ala | Asp | Gly | Ile | |
| | | 480 | | | | | 485 | | | | | 490 | | | | |
| ATC | AAT | GTC | TCT | GCC | CGT | GAC | AAG | GCT | ACC | AAC | AAG | GAT | TCT | TCC | ATC | 1777 |
| Ile | Asn | Val | Ser | Ala | Arg | Asp | Lys | Ala | Thr | Asn | Lys | Asp | Ser | Ser | Ile | |
| | 495 | | | | | 500 | | | | | 505 | | | | | |
| ACT | GTT | GCT | GGA | TCT | TCC | GGT | TTA | ACT | GAT | TCT | GAG | ATT | GAG | GCT | ATG | 1825 |
| Thr | Val | Ala | Gly | Ser | Ser | Gly | Leu | Thr | Asp | Ser | Glu | Ile | Glu | Ala | Met | |
| 510 | | | | | 515 | | | | | 520 | | | | | 525 | |
| GTT | GCC | GAT | GCT | GAG | AAG | TAT | CGT | GCC | AGT | GAC | ATG | GCT | CGC | AAG | GAG | 1873 |
| Val | Ala | Asp | Ala | Glu | Lys | Tyr | Arg | Ala | Ser | Asp | Met | Ala | Arg | Lys | Glu | |
| | | | | 530 | | | | | 535 | | | | | 540 | | |
| GCT | ATT | GAG | AAC | GGA | AAC | AGA | GCT | GAA | AGC | GTC | TGC | ACC | GAT | ATT | GAA | 1921 |
| Ala | Ile | Glu | Asn | Gly | Asn | Arg | Ala | Glu | Ser | Val | Cys | Thr | Asp | Ile | Glu | |
| | | | 545 | | | | | 550 | | | | | 555 | | | |
| AGC | AAC | CTT | GAC | ATT | CAC | AAA | GAC | AAA | TTG | GAC | CAA | CAA | GCT | GTT | GAA | 1969 |
| Ser | Asn | Leu | Asp | Ile | His | Lys | Asp | Lys | Leu | Asp | Gln | Gln | Ala | Val | Glu | |
| | | | 560 | | | | | 565 | | | | | 570 | | | |
| GAC | TTG | CGC | TCC | AAG | ATC | ACC | GAT | CTC | CGT | GAA | ACT | GTT | GCC | AAG | GTC | 2017 |
| Asp | Leu | Arg | Ser | Lys | Ile | Thr | Asp | Leu | Arg | Glu | Thr | Val | Ala | Lys | Val | |
| | 575 | | | | | 580 | | | | | 585 | | | | | |
| AAC | GCT | GGT | GAC | GAA | GGT | ATT | ACT | AGT | GAA | GAT | ATG | AAG | AAG | AAG | ATT | 2065 |
| Asn | Ala | Gly | Asp | Glu | Gly | Ile | Thr | Ser | Glu | Asp | Met | Lys | Lys | Lys | Ile | |
| 590 | | | | | 595 | | | | | 600 | | | | | 605 | |
| GAT | GAA | ATT | CAA | CAA | CTC | TCT | TTG | AAG | GTT | TTC | GAG | TCT | GTC | TAC | AAG | 2113 |
| Asp | Glu | Ile | Gln | Gln | Leu | Ser | Leu | Lys | Val | Phe | Glu | Ser | Val | Tyr | Lys | |
| | | | | 610 | | | | | 615 | | | | | 620 | | |
| AAC | CAA | AAT | CAA | GGT | AAT | GAA | TCT | TCT | GGT | GAT | AAC | TCT | GCT | CCT | GAG | 2161 |
| Asn | Gln | Asn | Gln | Gly | Asn | Glu | Ser | Ser | Gly | Asp | Asn | Ser | Ala | Pro | Glu | |
| | | | 625 | | | | | 630 | | | | | 635 | | | |
| GGT | GAC | AAG | AAG | TAGAGTGCAC | | ACCACAGTAC | | GAAATGACAT | | GTGCAATTTT | | | | | | 2213 |
| Gly | Asp | Lys | Lys | | | | | | | | | | | | | |
| | | | 640 | | | | | | | | | | | | | |

CAATTTTAGC TCTATATGTC AAAAAATTTA TGTGGATAAT TGATTATCCA TTTACATGTT 2273

GAAAGAAAAT GTCTGGATTT TGAAAAGGTA AACTATGATA TTTTTATTAA ATGTTCTAAA 2333

AAAAAAAAAA AAAAAAAAAA AAAAACCGGA ATTC 2367

( 2 ) INFORMATION FOR SEQ ID NO:4:

(i) SEQUENCE CHARACTERISTICS:
    (A) LENGTH: 641 amino acids
    (B) TYPE: amino acid
    (D) TOPOLOGY: linear (ii) MOLECULE TYPE: protein (xi) SEQUENCE DESCRIPTION: SEQ ID NO:4:

```
Met Thr Ala Arg Trp Asn Ser Asn Ala Ser Gly Asn Glu Lys Val Lys
 1               5                  10                  15
Gly Pro Val Ile Gly Ile Asp Leu Gly Thr Thr Thr Ser Cys Leu Ala
             20                  25                  30
Ile Met Glu Gly Gln Thr Pro Lys Val Ile Ala Asn Ala Glu Gly Thr
         35                  40                  45
Arg Thr Thr Pro Ser Val Val Ala Phe Thr Lys Asp Gly Glu Arg Leu
     50                  55                  60
Val Gly Val Ser Ala Lys Arg Gln Ala Val Ile Asn Pro Glu Asn Thr
 65                  70                  75                  80
Phe Phe Ala Thr Lys Arg Leu Ile Gly Arg Arg Phe Lys Glu Pro Glu
                 85                  90                  95
Val Gln Arg Asp Ile Lys Glu Val Pro Tyr Lys Ile Val Glu His Ser
             100                 105                 110
Asn Gly Asp Ala Trp Leu Glu Ala Arg Gly Lys Thr Tyr Ser Pro Ser
         115                 120                 125
Gln Ile Gly Gly Phe Ile Leu Ser Lys Met Arg Glu Thr Ala Ser Thr
     130                 135                 140
Tyr Leu Gly Lys Asp Val Lys Asn Ala Val Val Thr Val Pro Ala Tyr
145                 150                 155                 160
Phe Asn Asp Ser Gln Arg Gln Ala Thr Lys Ala Ala Gly Ala Ile Ala
                165                 170                 175
Gly Leu Asn Val Leu Arg Val Val Asn Glu Pro Thr Ala Ala Ala Leu
            180                 185                 190
Ala Tyr Gly Leu Asp Lys Lys Asn Asp Ala Ile Val Ala Val Phe Asp
        195                 200                 205
Leu Gly Gly Gly Thr Phe Asp Ile Ser Ile Leu Glu Leu Asn Asn Gly
    210                 215                 220
Val Phe Glu Val Arg Ser Thr Asn Gly Asp Thr His Leu Gly Gly Glu
225                 230                 235                 240
Asp Phe Asp Val Ala Leu Val Arg His Ile Val Glu Thr Phe Lys Lys
                245                 250                 255
Asn Glu Gly Leu Asp Leu Ser Lys Asp Arg Leu Ala Val Gln Arg Ile
            260                 265                 270
Arg Glu Ala Ala Glu Lys Ala Lys Cys Glu Leu Ser Ser Leu Ser Lys
        275                 280                 285
Thr Asp Ile Ser Leu Pro Phe Ile Thr Ala Asp Ala Thr Gly Pro Lys
    290                 295                 300
His Ile Asn Met Glu Ile Ser Arg Ala Gln Phe Glu Lys Leu Val Asp
305                 310                 315                 320
Pro Leu Val Arg Arg Thr Ile Asp Pro Cys Lys Arg Ala Leu Lys Asp
                325                 330                 335
Ala Asn Leu Gln Thr Ser Glu Ile Asn Glu Val Ile Leu Val Gly Gly
            340                 345                 350
Met Thr Arg Met Pro Arg Val Val Glu Thr Val Lys Ser Ile Phe Lys
        355                 360                 365
Arg Glu Pro Ala Lys Ser Val Asn Pro Asp Glu Ala Val Ala Ile Gly
```

|     |     |     |     | 370 |     |     |     |     | 375 |     |     |     |     | 380 |     |
|-----|-----|-----|-----|-----|-----|-----|-----|-----|-----|-----|-----|-----|-----|-----|-----|

Ala Ala Ile Gln Gly Gly Val Leu Ser Gly His Val Lys Asp Leu Val
385                 390                 395                 400

Leu Leu Asp Val Thr Pro Leu Ser Leu Gly Ile Glu Thr Leu Gly Gly
                 405                 410                 415

Val Phe Thr Arg Leu Ile Asn Arg Asn Thr Thr Ile Pro Thr Arg Lys
             420                 425                 430

Ser Gln Val Phe Ser Thr Ala Ala Asp Gly Gln Thr Ala Val Glu Ile
             435                 440                 445

Arg Val Phe Gln Gly Glu Arg Glu Leu Val Arg Asp Asn Lys Leu Ile
450                 455                 460

Gly Asn Phe Gln Leu Thr Gly Ile Ala Pro Ala Pro Lys Gly Gln Pro
465                 470                 475                 480

Gln Ile Glu Val Ser Phe Asp Val Asp Ala Asp Gly Ile Ile Asn Val
                 485                 490                 495

Ser Ala Arg Asp Lys Ala Thr Asn Lys Asp Ser Ser Ile Thr Val Ala
             500                 505                 510

Gly Ser Ser Gly Leu Thr Asp Ser Glu Ile Glu Ala Met Val Ala Asp
         515                 520                 525

Ala Glu Lys Tyr Arg Ala Ser Asp Met Ala Arg Lys Glu Ala Ile Glu
530                 535                 540

Asn Gly Asn Arg Ala Glu Ser Val Cys Thr Asp Ile Glu Ser Asn Leu
545                 550                 555                 560

Asp Ile His Lys Asp Lys Leu Asp Gln Gln Ala Val Glu Asp Leu Arg
             565                 570                 575

Ser Lys Ile Thr Asp Leu Arg Glu Thr Val Ala Lys Val Asn Ala Gly
             580                 585                 590

Asp Glu Gly Ile Thr Ser Glu Asp Met Lys Lys Lys Ile Asp Glu Ile
         595                 600                 605

Gln Gln Leu Ser Leu Lys Val Phe Glu Ser Val Tyr Lys Asn Gln Asn
610                 615                 620

Gln Gly Asn Glu Ser Ser Gly Asp Asn Ser Ala Pro Glu Gly Asp Lys
625                 630                 635                 640

Lys (2) INFORMATION FOR SEQ ID NO:5:

(i) SEQUENCE CHARACTERISTICS:
    (A) LENGTH: 679 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:5:

Met Phe Ser Ala Arg Lys Ser Ser Val Gly Trp Leu Val Ser Ser Leu
1               5                   10                  15

Ala Val Phe Tyr Val Leu Leu Ala Val Ile Met Pro Ile Ala Leu Thr
             20                  25                  30

Gly Ser Gln Ser Ser Arg Val Val Ala Arg Ala Ala Glu Asp His Glu
         35                  40                  45

Asp Tyr Gly Thr Val Ile Gly Ile Asp Leu Gly Thr Thr Tyr Ser Cys
         50                  55                  60

Val Ala Val Met Lys Asn Gly Lys Thr Glu Ile Leu Ala Asn Glu Gln
65                  70                  75                  80

```
Gly Asn Arg Ile Thr Pro Ser Tyr Val Ser Phe Thr Asp Asp Glu Arg
             85              90              95
Leu Ile Gly Asp Ala Ala Lys Asn Ala Ala Ser Asn Pro Lys Asn
            100             105             110
Thr Ile Phe Asp Ile Lys Arg Leu Ile Gly Leu Gln Tyr Asn Asp Pro
            115             120             125
Thr Val Gln Arg Asp Ile Lys His Leu Pro Tyr Thr Val Val Asn Lys
        130             135             140
Gly Asn Lys Pro Tyr Val Glu Val Thr Val Lys Gly Glu Lys Lys Glu
145             150             155             160
Phe Thr Pro Glu Glu Val Ser Gly Met Ile Leu Gly Lys Met Lys Gln
                165             170             175
Ile Ala Glu Asp Tyr Leu Gly Lys Lys Val Thr His Ala Val Val Thr
            180             185             190
Val Pro Ala Tyr Phe Asn Asp Ala Gln Arg Gln Ala Thr Lys Asp Ala
        195             200             205
Gly Ala Ile Ala Gly Leu Asn Ile Leu Arg Ile Val Asn Glu Pro Thr
    210             215             220
Ala Ala Ala Ile Ala Tyr Gly Leu Asp Lys Thr Glu Asp Glu His Gln
225             230             235             240
Ile Ile Val Tyr Asp Leu Gly Gly Gly Thr Phe Asp Val Ser Leu Leu
            245             250             255
Ser Ile Glu Asn Gly Val Phe Glu Val Gln Ala Thr Ala Gly Asp Thr
            260             265             270
His Leu Gly Gly Glu Asp Phe Asp Tyr Lys Leu Val Arg His Phe Ala
        275             280             285
Gln Leu Phe Gln Lys Lys His Asp Leu Asp Val Thr Lys Asn Asp Lys
    290             295             300
Ala Met Ala Lys Leu Lys Arg Glu Ala Glu Lys Ala Lys Arg Ser Leu
305             310             315             320
Ser Ser Gln Thr Ser Thr Arg Ile Glu Ile Asp Ser Phe Phe Asn Gly
            325             330             335
Ile Asp Phe Ser Glu Thr Leu Thr Arg Ala Lys Phe Glu Glu Leu Asn
            340             345             350
Leu Ala Leu Phe Lys Lys Thr Leu Lys Pro Val Glu Lys Val Leu Lys
            355             360             365
Asp Ser Gly Leu Gln Lys Glu Asp Ile Asp Ile Val Leu Val Gly
            370             375             380
Gly Ser Thr Arg Ile Pro Lys Val Gln Gln Leu Glu Lys Phe Phe
385             390             395             400
Asn Gly Lys Lys Ala Ser Lys Gly Ile Asn Pro Asp Glu Ala Val Ala
            405             410             415
Tyr Gly Ala Ala Val Gln Ala Gly Val Leu Ser Gly Glu Glu Gly Val
            420             425             430
Glu Asp Ile Val Leu Leu Asp Val Asn Ala Leu Thr Leu Gly Ile Glu
        435             440             445
Thr Thr Gly Gly Val Met Thr Pro Leu Ile Lys Arg Asn Thr Ala Ile
    450             455             460
Pro Thr Lys Lys Ser Gln Ile Phe Ser Thr Ala Val Asp Asn Gln Lys
465             470             475             480
Ala Val Arg Ile Gln Val Tyr Glu Gly Glu Arg Ala Met Val Lys Asp
            485             490             495
Asn Asn Leu Leu Gly Asn Phe Glu Leu Ser Asp Ile Arg Ala Ala Pro
            500             505             510
```

|     |     |     |     |     |     |     |     |     |     |     |     |     |     |     |
| --- | --- | --- | --- | --- | --- | --- | --- | --- | --- | --- | --- | --- | --- | --- |
| Arg | Gly | Val | Pro | Gln | Ile | Glu | Val | Thr | Phe | Ala | Leu | Asp | Ala | Asn | Gly |
|     |     | 515 |     |     |     | 520 |     |     |     |     | 525 |     |     |     |
| Ile | Leu | Thr | Val | Ser | Ala | Thr | Asp | Lys | Asp | Thr | Gly | Lys | Ser | Glu | Ser |
|     | 530 |     |     |     |     | 535 |     |     |     | 540 |     |     |     |     |     |
| Ile | Thr | Ile | Ala | Asn | Asp | Lys | Gly | Arg | Leu | Ser | Gln | Asp | Asp | Ile | Asp |
| 545 |     |     |     |     | 550 |     |     |     |     | 555 |     |     |     |     | 560 |
| Arg | Met | Val | Glu | Glu | Ala | Glu | Lys | Tyr | Ala | Ala | Glu | Asp | Ala | Lys | Phe |
|     |     |     |     | 565 |     |     |     |     | 570 |     |     |     |     | 575 |     |
| Lys | Ala | Lys | Ser | Glu | Ala | Arg | Asn | Thr | Phe | Glu | Asn | Phe | Val | His | Tyr |
|     |     |     | 580 |     |     |     |     | 585 |     |     |     |     | 590 |     |     |
| Val | Lys | Asn | Ser | Val | Asn | Gly | Glu | Leu | Ala | Glu | Ile | Met | Asp | Glu | Asp |
|     |     | 595 |     |     |     |     | 600 |     |     |     |     | 605 |     |     |     |
| Asp | Lys | Glu | Thr | Val | Leu | Asp | Asn | Val | Asn | Glu | Ser | Leu | Glu | Trp | Leu |
|     |     | 610 |     |     |     |     | 615 |     |     |     |     | 620 |     |     |     |
| Glu | Asp | Asn | Ser | Asp | Val | Ala | Glu | Ala | Glu | Asp | Phe | Glu | Glu | Lys | Met |
| 625 |     |     |     |     | 630 |     |     |     |     | 635 |     |     |     |     | 640 |
| Ala | Ser | Phe | Lys | Glu | Ser | Val | Glu | Pro | Ile | Leu | Ala | Lys | Ala | Ser | Ala |
|     |     |     |     | 645 |     |     |     |     | 650 |     |     |     |     | 655 |     |
| Ser | Gln | Gly | Ser | Thr | Ser | Gly | Glu | Gly | Phe | Glu | Asp | Glu | Asp | Asp | Asp |
|     |     |     | 660 |     |     |     |     | 665 |     |     |     |     | 670 |     |     |
| Asp | Tyr | Phe | Asp | Asp | Glu | Leu |     |     |     |     |     |     |     |     |     |
|     |     | 675 |     |     |     |     |     |     |     |     |     |     |     |     |     |

( 2 ) INFORMATION FOR SEQ ID NO:6:

( i ) SEQUENCE CHARACTERISTICS:
        ( A ) LENGTH: 2574 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 441..2429

( x i ) SEQUENCE DESCRIPTION: SEQ ID NO:6:

```
CACAATATCA ATAAGTTCCA CTCACGCTTT GTCTTTCACA ATATCATTTC AGAATTTACC          60

AATTTCGATT TTCATTGTTA CATTCATTGC TATGAAAACG TAAGGTGGTG GCGGCAATAG         120

GACTTATCGA AATGTACAGA ACTCACTATA GAATTGTTGT GTTGATGAGC TTCAACTGCA         180

TTCTTCTGGA AAGTACTAGT ATTAACGACG TGACTGCTCC TCTCGTTACT TAGCTGATTT         240

CTGGTACGCT ATTAAACTCA TCCAAAACCA ACTATTCTAG TTTGGTAAAT CTTAATCAAA         300

AACTATTAAA ACCCGTTTAC TATTTACTTA ACAGGTTGTT TTCAATAATT GGGAATTGCT         360

TGTGCCTACG ATCTCTTGTA ATTGAACTAC ACATATAAGC ATTTATAAGT TGGTAATCTT         420

CAAATTCTTG TTTATTGAAA ATG AAG AAG TTC CAG CTA TTT AGC ATT TTA            470
                      Met Lys Lys Phe Gln Leu Phe Ser Ile Leu
                        1               5                  10

AGC TAC TTT GTA GCT TTA TTC CTC CTA CCT ATG GCT TTT GCT AGT GGT          518
Ser Tyr Phe Val Ala Leu Phe Leu Leu Pro Met Ala Phe Ala Ser Gly
            15                  20                  25

GAT GAT AAC TCT ACA GAA TCA TAT GGA ACA GTT ATT GGT ATT GAT CTT          566
Asp Asp Asn Ser Thr Glu Ser Tyr Gly Thr Val Ile Gly Ile Asp Leu
                30                  35                  40

GGT ACA ACA TAC TCT TGC GTT GCC GTT ATG AAA AAT GGT CGT GTA GAA          614
Gly Thr Thr Tyr Ser Cys Val Ala Val Met Lys Asn Gly Arg Val Glu
            45                  50                  55
```

| | | | | | | | | | | | | | | | | |
|---|---|---|---|---|---|---|---|---|---|---|---|---|---|---|---|---|
| ATT | ATT | GCC | AAC | GAT | CAG | GGT | AAT | CGT | ATT | ACA | CCC | TCA | TAT | GTG | GCC | 662 |
| Ile | Ile | Ala | Asn | Asp | Gln | Gly | Asn | Arg | Ile | Thr | Pro | Ser | Tyr | Val | Ala | |
| | 60 | | | | 65 | | | | | 70 | | | | | | |
| TTT | ACT | GAA | GAC | GAA | CGT | TTG | GTT | GGT | GAG | GCC | GCT | AAG | AAC | CAA | GCT | 710 |
| Phe | Thr | Glu | Asp | Glu | Arg | Leu | Val | Gly | Glu | Ala | Ala | Lys | Asn | Gln | Ala | |
| 75 | | | | | 80 | | | | | 85 | | | | | 90 | |
| CCT | TCC | AAT | CCT | GAA | AAC | ACC | ATT | TTT | GAC | ATC | AAG | CGT | CTT | ATT | GGA | 758 |
| Pro | Ser | Asn | Pro | Glu | Asn | Thr | Ile | Phe | Asp | Ile | Lys | Arg | Leu | Ile | Gly | |
| | | | 95 | | | | | 100 | | | | | 105 | | | |
| CGT | AAG | TTT | GAC | GAA | AAG | ACA | ATG | GCC | AAG | GAT | ATT | AAA | TCT | TTT | CCT | 806 |
| Arg | Lys | Phe | Asp | Glu | Lys | Thr | Met | Ala | Lys | Asp | Ile | Lys | Ser | Phe | Pro | |
| | | | 110 | | | | 115 | | | | | 120 | | | | |
| TTC | CAT | ATT | GTA | AAT | GAC | AAG | AAC | CGT | CCT | TTG | GTT | GAG | GTT | AAT | GTA | 854 |
| Phe | His | Ile | Val | Asn | Asp | Lys | Asn | Arg | Pro | Leu | Val | Glu | Val | Asn | Val | |
| | | 125 | | | | | 130 | | | | | 135 | | | | |
| GGT | GGT | AAG | AAG | AAA | AAG | TTT | ACC | CCT | GAA | GAA | ATT | TCA | GCC | ATG | ATT | 902 |
| Gly | Gly | Lys | Lys | Lys | Lys | Phe | Thr | Pro | Glu | Glu | Ile | Ser | Ala | Met | Ile | |
| | 140 | | | | | 145 | | | | | 150 | | | | | |
| CTT | AGT | AAA | ATG | AAG | CAA | ACT | GCT | GAA | GCT | TAC | CTC | GGA | AAG | CCT | GTC | 950 |
| Leu | Ser | Lys | Met | Lys | Gln | Thr | Ala | Glu | Ala | Tyr | Leu | Gly | Lys | Pro | Val | |
| 155 | | | | | 160 | | | | | 165 | | | | | 170 | |
| ACT | CAC | TCT | GTT | GTT | ACT | GTC | CCC | GCC | TAC | TTC | AAT | GAC | GCT | CAG | CGT | 998 |
| Thr | His | Ser | Val | Val | Thr | Val | Pro | Ala | Tyr | Phe | Asn | Asp | Ala | Gln | Arg | |
| | | | 175 | | | | | 180 | | | | | 185 | | | |
| CAG | GCT | ACC | AAG | GAT | GCT | GGT | ACT | ATT | GCC | GGC | TTG | AAT | GTT | ATT | CGT | 1046 |
| Gln | Ala | Thr | Lys | Asp | Ala | Gly | Thr | Ile | Ala | Gly | Leu | Asn | Val | Ile | Arg | |
| | | | 190 | | | | | 195 | | | | | 200 | | | |
| ATC | GTC | AAT | GAG | CCT | ACT | GCG | GCT | GCT | ATT | GCC | TAC | GGA | TTA | GAC | AAA | 1094 |
| Ile | Val | Asn | Glu | Pro | Thr | Ala | Ala | Ala | Ile | Ala | Tyr | Gly | Leu | Asp | Lys | |
| | | 205 | | | | | 210 | | | | | 215 | | | | |
| ACT | GAT | ACA | GAG | AAG | CAT | ATT | GTT | GTT | TAT | GAT | TTA | GGT | GGT | GGT | ACT | 1142 |
| Thr | Asp | Thr | Glu | Lys | His | Ile | Val | Val | Tyr | Asp | Leu | Gly | Gly | Gly | Thr | |
| | 220 | | | | | 225 | | | | | 230 | | | | | |
| TTT | GAC | GTT | TCT | CTT | TTG | TCT | ATT | GAC | AAT | GGT | GTT | TTC | GAA | GTT | TTG | 1190 |
| Phe | Asp | Val | Ser | Leu | Leu | Ser | Ile | Asp | Asn | Gly | Val | Phe | Glu | Val | Leu | |
| 235 | | | | | 240 | | | | | 245 | | | | | 250 | |
| GCT | ACT | TCA | GGT | GAT | ACC | CAT | CTC | GGT | GGT | GAG | GAC | TTT | GAC | AAC | CGT | 1238 |
| Ala | Thr | Ser | Gly | Asp | Thr | His | Leu | Gly | Gly | Glu | Asp | Phe | Asp | Asn | Arg | |
| | | | 255 | | | | | 260 | | | | | 265 | | | |
| GTT | ATC | AAC | TAC | TTA | GCC | CGT | ACT | TAC | AAC | CGC | AAG | AAC | AAT | GTC | GAT | 1286 |
| Val | Ile | Asn | Tyr | Leu | Ala | Arg | Thr | Tyr | Asn | Arg | Lys | Asn | Asn | Val | Asp | |
| | | | 270 | | | | | 275 | | | | | 280 | | | |
| GTT | ACT | AAG | GAT | CTT | AAG | GCT | ATG | GGA | AAA | CTC | AAG | CGT | GAA | GTT | GAA | 1334 |
| Val | Thr | Lys | Asp | Leu | Lys | Ala | Met | Gly | Lys | Leu | Lys | Arg | Glu | Val | Glu | |
| | | 285 | | | | | 290 | | | | | 295 | | | | |
| AAA | GCC | AAC | GGT | ACT | TTG | TCC | TCC | CAA | AAG | TCT | GTT | CGT | ATC | GAG | ATT | 1382 |
| Lys | Ala | Asn | Gly | Thr | Leu | Ser | Ser | Gln | Lys | Ser | Val | Arg | Ile | Glu | Ile | |
| | 300 | | | | | 305 | | | | | 310 | | | | | |
| GAA | TCT | TTC | TTT | AAC | GGT | CAA | GAC | TTT | TCT | GAA | ACT | TTA | TCC | CGT | GCT | 1430 |
| Glu | Ser | Phe | Phe | Asn | Gly | Gln | Asp | Phe | Ser | Glu | Thr | Leu | Ser | Arg | Ala | |
| 315 | | | | | 320 | | | | | 325 | | | | | 330 | |
| AAG | TTC | GAG | GAG | ATT | AAA | CAT | GGA | TCT | CTT | CAA | GAA | GAC | TTT | GAG | CCT | 1478 |
| Lys | Phe | Glu | Glu | Ile | Lys | His | Gly | Ser | Leu | Gln | Glu | Asp | Phe | Glu | Pro | |
| | | | | 335 | | | | | 340 | | | | | 345 | | |
| GTT | GAG | CAA | GTA | TTA | AAG | GAC | TCC | AAC | CTC | AAG | AAA | TCC | GAG | ATT | GAT | 1526 |
| Val | Glu | Gln | Val | Leu | Lys | Asp | Ser | Asn | Leu | Lys | Lys | Ser | Glu | Ile | Asp | |
| | | | 350 | | | | | 355 | | | | | 360 | | | |
| GAT | ATC | GTT | CTT | GTC | GGT | GGT | TCT | ACT | CGT | ATC | CCT | AAG | GTT | CAA | GAA | 1574 |
| Asp | Ile | Val | Leu | Val | Gly | Gly | Ser | Thr | Arg | Ile | Pro | Lys | Val | Gln | Glu | |
| | | 365 | | | | | 370 | | | | | 375 | | | | |

| | | | | | | | | | | | | | | | | |
|---|---|---|---|---|---|---|---|---|---|---|---|---|---|---|---|---|
| CTT | TTG | GAG | AGC | TTC | TTT | GGT | AAG | AAG | GCT | TCT | AAG | GGT | ATC | AAT | CCC | 1622 |
| Leu | Leu | Glu | Ser | Phe | Phe | Gly | Lys | Lys | Ala | Ser | Lys | Gly | Ile | Asn | Pro | |
| | 380 | | | | 385 | | | | | 390 | | | | | | |
| GAT | GAG | GCT | GTT | GCC | TAT | GGT | GCT | GCT | GTT | CAA | GCC | GGC | GTT | TTA | TCT | 1670 |
| Asp | Glu | Ala | Val | Ala | Tyr | Gly | Ala | Ala | Val | Gln | Ala | Gly | Val | Leu | Ser | |
| 395 | | | | | 400 | | | | | 405 | | | | | 410 | |
| GGC | GAG | GAA | GGA | AGT | GAT | AAC | ATT | GTC | CTC | TTG | GAC | GTT | ATC | CCT | CTT | 1718 |
| Gly | Glu | Glu | Gly | Ser | Asp | Asn | Ile | Val | Leu | Leu | Asp | Val | Ile | Pro | Leu | |
| | | | | 415 | | | | | 420 | | | | | 425 | | |
| ACT | TTA | GGT | ATT | GAG | ACT | ACC | GGT | GGT | GTT | ATG | ACT | AAA | CTT | ATC | GGT | 1766 |
| Thr | Leu | Gly | Ile | Glu | Thr | Thr | Gly | Gly | Val | Met | Thr | Lys | Leu | Ile | Gly | |
| | | | 430 | | | | | 435 | | | | | 440 | | | |
| CGT | AAC | ACT | CCT | ATT | CCT | ACT | CGT | AAG | TCG | CAA | ATT | TTC | TCT | ACT | GCG | 1814 |
| Arg | Asn | Thr | Pro | Ile | Pro | Thr | Arg | Lys | Ser | Gln | Ile | Phe | Ser | Thr | Ala | |
| | | 445 | | | | | 450 | | | | | 455 | | | | |
| GTT | GAC | AAT | CAA | AAT | ACT | GTT | TTA | ATT | CAA | GTC | TAT | GAA | GGT | GAA | CGT | 1862 |
| Val | Asp | Asn | Gln | Asn | Thr | Val | Leu | Ile | Gln | Val | Tyr | Glu | Gly | Glu | Arg | |
| 460 | | | | | 465 | | | | | 470 | | | | | | |
| ACT | CTT | ACT | AAG | GAC | AAC | AAC | CTT | CTT | GGA | AAA | TTT | GAC | CTT | CGT | GGT | 1910 |
| Thr | Leu | Thr | Lys | Asp | Asn | Asn | Leu | Leu | Gly | Lys | Phe | Asp | Leu | Arg | Gly | |
| 475 | | | | 480 | | | | | 485 | | | | | 490 | | |
| ATT | CCT | CCT | GCC | CCT | CGT | GGT | GTT | CCC | CAA | ATT | GAA | GTC | ACG | TTT | GAA | 1958 |
| Ile | Pro | Pro | Ala | Pro | Arg | Gly | Val | Pro | Gln | Ile | Glu | Val | Thr | Phe | Glu | |
| | | | | 495 | | | | | 500 | | | | | 505 | | |
| GTC | GAT | GCC | AAT | GGT | GTT | TTG | ACT | GTT | TCA | GCC | GTC | GAC | AAG | TCT | GGT | 2006 |
| Val | Asp | Ala | Asn | Gly | Val | Leu | Thr | Val | Ser | Ala | Val | Asp | Lys | Ser | Gly | |
| | | | 510 | | | | | 515 | | | | | 520 | | | |
| AAG | GGT | AAG | CCT | GAG | AAG | CTT | GTT | ATC | AAG | AAT | GAC | AAA | GGT | CGT | TTG | 2054 |
| Lys | Gly | Lys | Pro | Glu | Lys | Leu | Val | Ile | Lys | Asn | Asp | Lys | Gly | Arg | Leu | |
| | | 525 | | | | | 530 | | | | | 535 | | | | |
| TCT | GAG | GAA | GAT | ATC | GAG | CGC | ATG | GTT | AAG | GAG | GCC | GAA | GAA | TTC | GCT | 2102 |
| Ser | Glu | Glu | Asp | Ile | Glu | Arg | Met | Val | Lys | Glu | Ala | Glu | Glu | Phe | Ala | |
| | 540 | | | | | 545 | | | | | 550 | | | | | |
| GAA | GAA | GAT | AAG | ATT | TTG | AAG | GAG | CGT | ATT | GAA | GCT | CGT | AAT | ACT | CTT | 2150 |
| Glu | Glu | Asp | Lys | Ile | Leu | Lys | Glu | Arg | Ile | Glu | Ala | Arg | Asn | Thr | Leu | |
| 555 | | | | | 560 | | | | | 565 | | | | | 570 | |
| GAA | AAC | TAC | GCC | TAT | TCT | TTG | AAA | GGT | CAA | TTT | GAC | GAT | GAT | GAG | CAA | 2198 |
| Glu | Asn | Tyr | Ala | Tyr | Ser | Leu | Lys | Gly | Gln | Phe | Asp | Asp | Asp | Glu | Gln | |
| | | | | 575 | | | | | 580 | | | | | 585 | | |
| TTA | GGT | GGT | AAG | GTT | GAT | CCC | GAA | GAT | AAG | CAA | GCT | GTT | TTG | GAC | GCT | 2246 |
| Leu | Gly | Gly | Lys | Val | Asp | Pro | Glu | Asp | Lys | Gln | Ala | Val | Leu | Asp | Ala | |
| | | | 590 | | | | | 595 | | | | | 600 | | | |
| GTC | GAA | GAT | GTT | GCT | GAA | TGG | CTT | GAA | ATC | CAC | GGA | GAA | GAT | GCC | AGC | 2294 |
| Val | Glu | Asp | Val | Ala | Glu | Trp | Leu | Glu | Ile | His | Gly | Glu | Asp | Ala | Ser | |
| | | 605 | | | | | 610 | | | | | 615 | | | | |
| AAG | GAA | GAA | TTT | GAA | GAT | CAG | CGT | CAA | AAA | CTC | GAT | GCC | GTT | GTT | CAT | 2342 |
| Lys | Glu | Glu | Phe | Glu | Asp | Gln | Arg | Gln | Lys | Leu | Asp | Ala | Val | Val | His | |
| | 620 | | | | | 625 | | | | | 630 | | | | | |
| CCT | ATT | ACC | CAA | AAG | TTG | TAT | TCC | GAA | GGA | GCT | GGT | GAT | GCT | GAT | GAA | 2390 |
| Pro | Ile | Thr | Gln | Lys | Leu | Tyr | Ser | Glu | Gly | Ala | Gly | Asp | Ala | Asp | Glu | |
| 635 | | | | | 640 | | | | | 645 | | | | | 650 | |
| GAG | GAT | GAT | GAT | TAC | TTC | GAT | GAT | GAG | GCC | GAT | GAA | CTT | TAAAGTGTTT | | | 2439 |
| Glu | Asp | Asp | Asp | Tyr | Phe | Asp | Asp | Glu | Ala | Asp | Glu | Leu | | | | |
| | | | | 655 | | | | | 660 | | | | | | | |

| | | | | |
|---|---|---|---|---|
| TAAAATTGCC | TGTACTTTCA | TTTTTAAGC | TTTACTTAGT | AATTTTTATT | TAGTTCGAAG | 2499 |
| TATACGCAAG | TCTGACTCGA | ATGCTCTCAT | GGTTTCATGA | CCTTAATCTA | AGGGTATTTG | 2559 |
| GAAACCAAAT | GTTTT | | | | | 2574 |

( 2 ) INFORMATION FOR SEQ ID NO:7:

( i ) SEQUENCE CHARACTERISTICS:
        ( A ) LENGTH: 663 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Lys Lys Phe Gln Leu Phe Ser Ile Leu Ser Tyr Phe Val Ala Leu
 1               5                  10                  15
Phe Leu Leu Pro Met Ala Phe Ala Ser Gly Asp Asp Asn Ser Thr Glu
             20                  25                  30
Ser Tyr Gly Thr Val Ile Gly Ile Asp Leu Gly Thr Thr Tyr Ser Cys
         35                  40                  45
Val Ala Val Met Lys Asn Gly Arg Val Glu Ile Ile Ala Asn Asp Gln
     50                  55                  60
Gly Asn Arg Ile Thr Pro Ser Tyr Val Ala Phe Thr Glu Asp Glu Arg
 65                  70                  75                  80
Leu Val Gly Glu Ala Ala Lys Asn Gln Ala Pro Ser Asn Pro Glu Asn
                 85                  90                  95
Thr Ile Phe Asp Ile Lys Arg Leu Ile Gly Arg Lys Phe Asp Glu Lys
            100                 105                 110
Thr Met Ala Lys Asp Ile Lys Ser Phe Pro Phe His Ile Val Asn Asp
        115                 120                 125
Lys Asn Arg Pro Leu Val Glu Val Asn Val Gly Gly Lys Lys Lys Lys
    130                 135                 140
Phe Thr Pro Glu Glu Ile Ser Ala Met Ile Leu Ser Lys Met Lys Gln
145                 150                 155                 160
Thr Ala Glu Ala Tyr Leu Gly Lys Pro Val Thr His Ser Val Val Thr
                165                 170                 175
Val Pro Ala Tyr Phe Asn Asp Ala Gln Arg Gln Ala Thr Lys Asp Ala
            180                 185                 190
Gly Thr Ile Ala Gly Leu Asn Val Ile Arg Ile Val Asn Glu Pro Thr
        195                 200                 205
Ala Ala Ala Ile Ala Tyr Gly Leu Asp Lys Thr Asp Thr Glu Lys His
    210                 215                 220
Ile Val Val Tyr Asp Leu Gly Gly Gly Thr Phe Asp Val Ser Leu Leu
225                 230                 235                 240
Ser Ile Asp Asn Gly Val Phe Glu Val Leu Ala Thr Ser Gly Asp Thr
                245                 250                 255
His Leu Gly Gly Glu Asp Phe Asp Asn Arg Val Ile Asn Tyr Leu Ala
            260                 265                 270
Arg Thr Tyr Asn Arg Lys Asn Asn Val Asp Val Thr Lys Asp Leu Lys
        275                 280                 285
Ala Met Gly Lys Leu Lys Arg Glu Val Glu Lys Ala Asn Gly Thr Leu
    290                 295                 300
Ser Ser Gln Lys Ser Val Arg Ile Glu Ile Glu Ser Phe Phe Asn Gly
305                 310                 315                 320
Gln Asp Phe Ser Glu Thr Leu Ser Arg Ala Lys Phe Glu Glu Ile Lys
                325                 330                 335
His Gly Ser Leu Gln Glu Asp Phe Glu Pro Val Glu Gln Val Leu Lys
            340                 345                 350
Asp Ser Asn Leu Lys Lys Ser Glu Ile Asp Asp Ile Val Leu Val Gly
        355                 360                 365
```

| Gly | Ser | Thr | Arg | Ile | Pro | Lys | Val | Gln | Glu | Leu | Leu | Glu | Ser | Phe | Phe |
|-----|-----|-----|-----|-----|-----|-----|-----|-----|-----|-----|-----|-----|-----|-----|-----|
| 370 |     |     |     |     |     | 375 |     |     |     | 380 |     |     |     |     |     |
| Gly | Lys | Lys | Ala | Ser | Lys | Gly | Ile | Asn | Pro | Asp | Glu | Ala | Val | Ala | Tyr |
| 385 |     |     |     |     | 390 |     |     |     | 395 |     |     |     |     |     | 400 |
| Gly | Ala | Ala | Val | Gln | Ala | Gly | Val | Leu | Ser | Gly | Glu | Glu | Gly | Ser | Asp |
|     |     |     |     | 405 |     |     |     |     | 410 |     |     |     | 415 |     |     |
| Asn | Ile | Val | Leu | Leu | Asp | Val | Ile | Pro | Leu | Thr | Leu | Gly | Ile | Glu | Thr |
|     |     |     | 420 |     |     |     |     | 425 |     |     |     |     | 430 |     |     |
| Thr | Gly | Gly | Val | Met | Thr | Lys | Leu | Ile | Gly | Arg | Asn | Thr | Pro | Ile | Pro |
|     |     | 435 |     |     |     | 440 |     |     |     |     |     | 445 |     |     |     |
| Thr | Arg | Lys | Ser | Gln | Ile | Phe | Ser | Thr | Ala | Val | Asp | Asn | Gln | Asn | Thr |
|     | 450 |     |     |     |     | 455 |     |     |     |     | 460 |     |     |     |     |
| Val | Leu | Ile | Gln | Val | Tyr | Glu | Gly | Glu | Arg | Thr | Leu | Thr | Lys | Asp | Asn |
| 465 |     |     |     |     | 470 |     |     |     |     | 475 |     |     |     |     | 480 |
| Asn | Leu | Leu | Gly | Lys | Phe | Asp | Leu | Arg | Gly | Ile | Pro | Pro | Ala | Pro | Arg |
|     |     |     |     | 485 |     |     |     |     | 490 |     |     |     | 495 |     |     |
| Gly | Val | Pro | Gln | Ile | Glu | Val | Thr | Phe | Glu | Val | Asp | Ala | Asn | Gly | Val |
|     |     |     | 500 |     |     |     |     | 505 |     |     |     |     | 510 |     |     |
| Leu | Thr | Val | Ser | Ala | Val | Asp | Lys | Ser | Gly | Lys | Gly | Lys | Pro | Glu | Lys |
|     |     | 515 |     |     |     |     | 520 |     |     |     |     | 525 |     |     |     |
| Leu | Val | Ile | Lys | Asn | Asp | Lys | Gly | Arg | Leu | Ser | Glu | Glu | Asp | Ile | Glu |
|     | 530 |     |     |     |     | 535 |     |     |     |     | 540 |     |     |     |     |
| Arg | Met | Val | Lys | Glu | Ala | Glu | Glu | Phe | Ala | Glu | Glu | Asp | Lys | Ile | Leu |
| 545 |     |     |     |     | 550 |     |     |     |     | 555 |     |     |     |     | 560 |
| Lys | Glu | Arg | Ile | Glu | Ala | Arg | Asn | Thr | Leu | Glu | Asn | Tyr | Ala | Tyr | Ser |
|     |     |     |     | 565 |     |     |     |     | 570 |     |     |     |     | 575 |     |
| Leu | Lys | Gly | Gln | Phe | Asp | Asp | Glu | Gln | Leu | Gly | Gly | Lys | Val | Asp |     |
|     |     |     | 580 |     |     |     |     | 585 |     |     |     | 590 |     |     |     |
| Pro | Glu | Asp | Lys | Gln | Ala | Val | Leu | Asp | Ala | Val | Glu | Asp | Val | Ala | Glu |
|     |     | 595 |     |     |     |     | 600 |     |     |     |     | 605 |     |     |     |
| Trp | Leu | Glu | Ile | His | Gly | Glu | Asp | Ala | Ser | Lys | Glu | Glu | Phe | Glu | Asp |
| 610 |     |     |     |     |     | 615 |     |     |     |     | 620 |     |     |     |     |
| Gln | Arg | Gln | Lys | Leu | Asp | Ala | Val | Val | His | Pro | Ile | Thr | Gln | Lys | Leu |
| 625 |     |     |     |     | 630 |     |     |     |     | 635 |     |     |     |     | 640 |
| Tyr | Ser | Glu | Gly | Ala | Gly | Asp | Ala | Asp | Glu | Glu | Asp | Asp | Asp | Tyr | Phe |
|     |     |     |     | 645 |     |     |     |     | 650 |     |     |     |     | 655 |     |
| Asp | Asp | Glu | Ala | Asp | Glu | Leu |     |     |     |     |     |     |     |     |     |
|     |     |     | 660 |     |     |     |     |     |     |     |     |     |     |     |     |

( 2 ) INFORMATION FOR SEQ ID NO:8:

( i ) SEQUENCE CHARACTERISTICS:
        ( A ) LENGTH: 6030 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1004..4753

( x i ) SEQUENCE DESCRIPTION: SEQ ID NO:8:

| TTTTATCCTA | TGTCACGGAC | GACGACTTGT | ATCACCTTGA | ATTTTCTGAC | CAAAGGGGCC | 60 |
| GAGTCGCTTC | ACGAGGGGAT | GAGAAAGGAA | AAGAAGGGAA | AACTAAACTT | ATATAACGCA | 120 |
| GGTGTGTCTT | TCTACCATTG | CCATCAAGTT | ATTAAAGGCC | ACGAACAGGA | ACGCTAGAGA | 180 |

| | | |
|---|---|---|
| CCTGAGTTTG TCATTTGTTT AGTTCAAGGA TTAAATAAAC AATCCTTCTA CAAATAAGTC | 240 |
| CTTTCTTTCA CCATCGTCTT AAGACCACTG CCTCCAACGA AAACTAACCT AAAAGAGTTT | 300 |
| AGATCACGAG TATTTCGCT CTTTCCCTCC TTCCCTGGT TTTTTCTCGT TAGTTCTTTT | 360 |
| CATTTAAAAA CTCTTCTCTT GTCAAGAATT TAAAAGACGA AGAGTCCAAC ACCGACTGAT | 420 |
| TTTCTAACAG CAAAGGAACG AAGTTTTGCC GTGCAAACAA TAATTTCTAA ATTATAATTT | 480 |
| TGAGCCTAGC TGAGAAATAG GAGAGATTAT ATTTTAGAAA GGTAAGAAGT TTTTCTGTCA | 540 |
| TTCCTTTTAG AATATTTGCT ACGTTCTAAC ATTTTTGTT ACTCAAGCGC ATTTTCTGCA | 600 |
| ACTTCCCTTA TAAGCTATTT CCTTTTTTG GGACCGATCC TTTCTTCTGT CTTTGGTAAC | 660 |
| CTAAAAACCG GAATAGTCAA AGTTATCTGC ATAGTCTTCT TGCCAGGCTT ATTTTCGCCA | 720 |
| TACCATTTTT CTGGTACCCT AAACATTTTG GTCTTATTTT AGAACAGCTG GTGCCTCGTT | 780 |
| TTTCCGCATT AGGCGCACTT TTTTCATAGC CACTATTCTA AAAGAAACAA CTTTTTTTCA | 840 |
| AAGGGAAATC TAAGTTGCCT GCACGAAGAA TAAGACAAGG GTTCATAAAC GTATAGTATT | 900 |
| TGCCAAGTTC CATCTTTTTC TTTGTCACTT TAATATCGCA AAACAGAACA CCAAAAACCT | 960 |

TTCAGCGCAA AGATTTGGCC CAATTATTCC ATCTTTATAC ACT ATG TCT AAA AAT   1015
                      Met Ser Lys Asn
                       1

AGC AAC GTT AAC AAC AAT AGA TCC CAA GAG CCA AAT AAC ATG TTT GTG   1063
Ser Asn Val Asn Asn Asn Arg Ser Gln Glu Pro Asn Asn Met Phe Val
 5         10        15         20

CAA ACC ACA GGA GGT GGT AAA AAC GCC CCA AAG CAG ATT CAT GTT GCA   1111
Gln Thr Thr Gly Gly Gly Lys Asn Ala Pro Lys Gln Ile His Val Ala
        25        30         35

CAC AGA CGT TCC CAA AGT GAG TTG ACA AAT TTG ATG ATT GAA CAA TTC   1159
His Arg Arg Ser Gln Ser Glu Leu Thr Asn Leu Met Ile Glu Gln Phe
      40        45         50

ACT TTG CAG AAG CAG TTG GAG CAA GTT CAA GCA CAG CAG CAA CAG TTG   1207
Thr Leu Gln Lys Gln Leu Glu Gln Val Gln Ala Gln Gln Gln Gln Leu
   55        60        65

ATG GCT CAG CAA CAG CAA TTG GCA CAA CAG ACA GGA CAA TAC CTG TCA   1255
Met Ala Gln Gln Gln Gln Leu Ala Gln Gln Thr Gly Gln Tyr Leu Ser
 70         75        80

GGA AAT TCT GGC TCT AAC AAT CAT TTC ACG CCT CAA CCG CCT CAC CCT   1303
Gly Asn Ser Gly Ser Asn Asn His Phe Thr Pro Gln Pro Pro His Pro
 85         90        95       100

CAT TAC AAC TCA AAC GGT AAT TCA CCT GGT ATG AGT GCA GGT GGC AGC   1351
His Tyr Asn Ser Asn Gly Asn Ser Pro Gly Met Ser Ala Gly Gly Ser
        105       110        115

AGA AGT AGA ACT CAC TCC AGG AAC AAC TCC GGA TAT TAT CAT AAT TCA   1399
Arg Ser Arg Thr His Ser Arg Asn Asn Ser Gly Tyr Tyr His Asn Ser
      120        125        130

TAT GAT AAC AAT AAC AAT AGC AAT AAT CCT GGG TCT AAC TCA CAC AGA   1447
Tyr Asp Asn Asn Asn Asn Ser Asn Asn Pro Gly Ser Asn Ser His Arg
     135        140        145

AAG ACG AGT TCA CAA TCC AGC ATA TAT GGC CAT TCC AGA AGA CAT TCT   1495
Lys Thr Ser Ser Gln Ser Ser Ile Tyr Gly His Ser Arg Arg His Ser
  150        155        160

TTA GGT CTA AAT GAA GCG AAA AAG GCT GCT GCG GAA GAA CAA GCT AAA   1543
Leu Gly Leu Asn Glu Ala Lys Lys Ala Ala Ala Glu Glu Gln Ala Lys
165         170        175       180

AGA ATA TCT GGG GGT GAA GCA GGC GTA ACT GTG AAG ATA GAT TCT GTT   1591
Arg Ile Ser Gly Gly Glu Ala Gly Val Thr Val Lys Ile Asp Ser Val
        185       190        195

CAA GCT GAT AGT GGC TCA AAT TCT ACT ACA GAA CAA TCT GAT TTT AAA   1639
Gln Ala Asp Ser Gly Ser Asn Ser Thr Thr Glu Gln Ser Asp Phe Lys

|     |     |     |     |     |     |     |     |     |     |     |     |     |     |     |     |
|---|---|---|---|---|---|---|---|---|---|---|---|---|---|---|---|
|     |     |     |     |     | 200 |     |     |     | 205 |     |     |     | 210 |     |     |
| TTT | CCA | CCA | CCA | CCA | AAT | GCT | CAT | CAG | GGC | CAT | CGT | CGC | GCA | ACT | TCA | 1687 |
| Phe | Pro | Pro 215 | Pro | Pro | Asn | Ala | His | Gln 220 | Gly | His | Arg | Arg 225 | Ala | Thr | Ser |     |
| AAC | CTA | TCA | CCT | CCC | TCT | TTC | AAA | TTT | CCT | CCA | AAC | TCT | CAC | GGG | GAT | 1735 |
| Asn | Leu 230 | Ser | Pro | Pro | Ser | Phe | Lys 235 | Phe | Pro | Pro | Asn | Ser 240 | His | Gly | Asp |     |
| AAT | GAC | GAT | GAA | TTC | ATA | GCA | ACC | TCT | TCA | ACG | CAC | CGC | CGT | TCA | AAG | 1783 |
| Asn | Asp 245 | Asp | Glu | Phe | Ile 250 | Ala | Thr | Ser | Ser | Thr 255 | His | Arg | Arg | Ser | Lys 260 |     |
| ACA | AGA | AAC | AAT | GAA | TAT | TCT | CCA | GGC | ATT | AAT | TCC | AAC | TGG | AGA | AAC | 1831 |
| Thr | Arg | Asn | Asn | Glu 265 | Tyr | Ser | Pro | Gly | Ile 270 | Asn | Ser | Asn | Trp | Arg 275 | Asn |     |
| CAA | TCA | CAG | CAA | CCT | CAA | CAG | CAG | CTT | TCT | CCA | TTC | CGC | CAC | AGA | GGA | 1879 |
| Gln | Ser | Gln 280 | Gln | Pro | Gln | Gln | Gln | Leu 285 | Ser | Pro | Phe | Arg | His 290 | Arg | Gly |     |
| TCT | AAT | TCA | AGG | GAT | TAC | AAT | TCC | TTC | AAT | ACC | TTA | GAA | CCT | CCT | GCG | 1927 |
| Ser | Asn | Ser 295 | Arg | Asp | Tyr | Asn | Ser 300 | Phe | Asn | Thr | Leu | Glu 305 | Pro | Pro | Ala |     |
| ATA | TTT | CAG | CAG | GGA | CAC | AAA | CAT | CGT | GCC | TCT | AAT | TCA | TCA | GTT | CAT | 1975 |
| Ile | Phe 310 | Gln | Gln | Gly | His | Lys 315 | His | Arg | Ala | Ser | Asn 320 | Ser | Ser | Val | His |     |
| AGT | TTC | AGT | TCA | CAA | GGT | AAT | AAT | AAC | GGA | GGT | GGA | CGT | AAG | TCC | CTA | 2023 |
| Ser 325 | Phe | Ser | Ser | Gln | Gly 330 | Asn | Asn | Asn | Gly | Gly 335 | Gly | Arg | Lys | Ser | Leu 340 |     |
| TTT | GCA | CCC | TAC | CTT | CCC | CAA | GCC | AAC | ATT | CCA | GAG | CTA | ATC | CAA | GAA | 2071 |
| Phe | Ala | Pro | Tyr | Leu 345 | Pro | Gln | Ala | Asn | Ile 350 | Pro | Glu | Leu | Ile | Gln 355 | Glu |     |
| GGG | AGA | CTA | GTA | GCT | GGT | ATA | TTA | AGA | GTT | AAT | AAA | AAG | AAT | AGA | TCG | 2119 |
| Gly | Arg | Leu | Val 360 | Ala | Gly | Ile | Leu | Arg 365 | Val | Asn | Lys | Lys | Asn 370 | Arg | Ser |     |
| GAT | GCC | TGG | GTC | TCT | ACA | GAT | GGC | GCT | CTT | GAT | GCG | GAT | ATT | TAC | ATT | 2167 |
| Asp | Ala | Trp 375 | Val | Ser | Thr | Asp | Gly 380 | Ala | Leu | Asp | Ala | Asp 385 | Ile | Tyr | Ile |     |
| TGC | GGC | TCC | AAA | GAT | CGT | AAT | AGA | GCA | CTT | GAA | GGT | GAT | TTA | GTC | GCG | 2215 |
| Cys | Gly 390 | Ser | Lys | Asp | Arg | Asn 395 | Arg | Ala | Leu | Glu | Gly 400 | Asp | Leu | Val | Ala |     |
| GTA | GAA | CTA | TTA | GTT | GTG | GAC | GAT | GTT | TGG | GAG | TCC | AAG | AAA | GAA | AAG | 2263 |
| Val 405 | Glu | Leu | Leu | Val | Val 410 | Asp | Asp | Val | Trp | Glu 415 | Ser | Lys | Lys | Glu | Lys 420 |     |
| GAA | GAA | AAG | AAG | AGG | AGA | AAG | GAT | GCC | TCT | ATG | CAA | CAC | GAT | CTA | ATT | 2311 |
| Glu | Glu | Lys | Lys | Arg 425 | Arg | Lys | Asp | Ala | Ser 430 | Met | Gln | His | Asp | Leu 435 | Ile |     |
| CCT | TTG | AAC | AGT | AGT | GAC | GAT | TAC | CAC | AAC | GAT | GCA | TCT | GTT | ACT | GCT | 2359 |
| Pro | Leu | Asn | Ser 440 | Ser | Asp | Asp | Tyr | His 445 | Asn | Asp | Ala | Ser | Val 450 | Thr | Ala |     |
| GCA | ACA | AGC | AAC | AAT | TTT | CTA | TCT | TCT | CCC | TCC | TCG | TCT | GAT | TCG | CTA | 2407 |
| Ala | Thr | Ser 455 | Asn | Asn | Phe | Leu | Ser 460 | Ser | Pro | Ser | Ser | Ser 465 | Asp | Ser | Leu |     |
| AGC | AAG | GAT | GAT | TTA | TCC | GTC | AGA | AGA | AAG | AGG | TCA | TCT | ACT | ATC | AAT | 2455 |
| Ser | Lys 470 | Asp | Asp | Leu | Ser | Val 475 | Arg | Arg | Lys | Arg | Ser 480 | Ser | Thr | Ile | Asn |     |
| AAT | GAT | AGT | GAT | TCC | TTA | TCA | TCT | CCT | ACC | AAA | TCA | GGA | GTA | AGG | AGA | 2503 |
| Asn | Asp 485 | Ser | Asp | Ser | Leu 490 | Ser | Ser | Pro | Thr | Lys 495 | Ser | Gly | Val | Arg | Arg 500 |     |
| AGA | AGT | TCA | TTG | AAA | CAA | CGT | CCA | ACT | CAA | AAG | AAA | AAT | GAC | GAT | GTT | 2551 |
| Arg | Ser | Ser | Leu | Lys 505 | Gln | Arg | Pro | Thr | Gln 510 | Lys | Lys | Asn | Asp | Asp 515 | Val |     |
| GAA | GTT | GAA | GGT | CAG | TCA | TTG | TTA | TTA | GTT | GAA | GAA | GAA | GAA | ATC | AAC | 2599 |
| Glu | Val | Glu | Gly | Gln | Ser | Leu | Leu | Leu | Val | Glu | Glu | Glu | Glu | Ile | Asn |     |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 520 |     |     |     |     | 525 |     |     |     |     | 530 |     |      |
| GAT | AAA | TAT | AAG | CCA | CTT | TAC | GCA | GGC | CAT | GTC | GTT | GCT | GTT | TTG | GAC | 2647 |
| Asp | Lys | Tyr | Lys | Pro | Leu | Tyr | Ala | Gly | His | Val | Val | Ala | Val | Leu | Asp |      |
|     |     | 535 |     |     |     |     | 540 |     |     |     |     | 545 |     |     |     |      |
| CGT | ATC | CCT | GGT | CAG | TTA | TTT | AGC | GGT | ACA | TTA | GGT | TTG | TTG | AGA | CCA | 2695 |
| Arg | Ile | Pro | Gly | Gln | Leu | Phe | Ser | Gly | Thr | Leu | Gly | Leu | Leu | Arg | Pro |      |
| 550 |     |     |     |     |     | 555 |     |     |     |     |     | 560 |     |     |     |      |
| TCC | CAA | CAA | GCT | AAT | AGC | GAC | AAT | AAC | AAA | CCA | CCA | CAA | AGC | CCA | AAA | 2743 |
| Ser | Gln | Gln | Ala | Asn | Ser | Asp | Asn | Asn | Lys | Pro | Pro | Gln | Ser | Pro | Lys |      |
| 565 |     |     |     |     | 570 |     |     |     |     | 575 |     |     |     |     | 580 |      |
| ATT | GCT | TGG | TTC | AAG | CCT | ACT | GAT | AAG | AAG | GTG | CCA | TTA | ATT | GCA | ATT | 2791 |
| Ile | Ala | Trp | Phe | Lys | Pro | Thr | Asp | Lys | Lys | Val | Pro | Leu | Ile | Ala | Ile |      |
|     |     |     |     | 585 |     |     |     |     | 590 |     |     |     |     | 595 |     |      |
| CCT | ACA | GAA | TTA | GCT | CCA | AAG | GAC | TTT | GTT | GAA | AAC | GCT | GAT | AAA | TAC | 2839 |
| Pro | Thr | Glu | Leu | Ala | Pro | Lys | Asp | Phe | Val | Glu | Asn | Ala | Asp | Lys | Tyr |      |
|     |     |     | 600 |     |     |     |     | 605 |     |     |     |     | 610 |     |     |      |
| TCC | GAA | AAG | TTA | TTC | GTT | GCC | TCT | ATT | AAA | CGT | TGG | CCA | ATC | ACA | TCT | 2887 |
| Ser | Glu | Lys | Leu | Phe | Val | Ala | Ser | Ile | Lys | Arg | Trp | Pro | Ile | Thr | Ser |      |
|     |     | 615 |     |     |     |     | 620 |     |     |     |     | 625 |     |     |     |      |
| TTG | CAT | CCA | TTT | GGT | ATT | TTA | GTT | TCC | GAA | CTT | GGA | GAT | ATT | CAC | GAT | 2935 |
| Leu | His | Pro | Phe | Gly | Ile | Leu | Val | Ser | Glu | Leu | Gly | Asp | Ile | His | Asp |      |
| 630 |     |     |     |     | 635 |     |     |     |     | 640 |     |     |     |     |     |      |
| CCT | GAT | ACT | GAA | ATT | GAT | TCC | ATT | TTA | AGG | GAT | AAC | AAT | TTT | CTT | TCG | 2983 |
| Pro | Asp | Thr | Glu | Ile | Asp | Ser | Ile | Leu | Arg | Asp | Asn | Asn | Phe | Leu | Ser |      |
| 645 |     |     |     |     | 650 |     |     |     |     | 655 |     |     |     |     | 660 |      |
| AAT | GAA | TAT | TTG | GAT | CAA | AAA | AAT | CCG | CAA | AAA | GAA | AAA | CCA | AGT | TTT | 3031 |
| Asn | Glu | Tyr | Leu | Asp | Gln | Lys | Asn | Pro | Gln | Lys | Glu | Lys | Pro | Ser | Phe |      |
|     |     |     |     | 665 |     |     |     |     | 670 |     |     |     |     | 675 |     |      |
| CAG | CCG | CTA | CCA | TTA | ACG | GCT | GAA | AGT | CTA | GAA | TAT | AGG | AGG | AAT | TTT | 3079 |
| Gln | Pro | Leu | Pro | Leu | Thr | Ala | Glu | Ser | Leu | Glu | Tyr | Arg | Arg | Asn | Phe |      |
|     |     |     | 680 |     |     |     |     | 685 |     |     |     |     | 690 |     |     |      |
| ACG | GAC | ACT | AAT | GAG | TAC | AAT | ATC | TTT | GCA | ATT | TCC | GAG | CTT | GGA | TGG | 3127 |
| Thr | Asp | Thr | Asn | Glu | Tyr | Asn | Ile | Phe | Ala | Ile | Ser | Glu | Leu | Gly | Trp |      |
|     |     | 695 |     |     |     |     | 700 |     |     |     |     | 705 |     |     |     |      |
| GTG | TCT | GAA | TTT | GCC | TTA | CAT | GTC | AGG | AAT | AAC | GGA | AAT | GGT | ACC | CTA | 3175 |
| Val | Ser | Glu | Phe | Ala | Leu | His | Val | Arg | Asn | Asn | Gly | Asn | Gly | Thr | Leu |      |
|     | 710 |     |     |     |     | 715 |     |     |     |     | 720 |     |     |     |     |      |
| GAG | CTG | GGT | TGT | CAT | GTT | GTT | GAT | GTG | ACC | AGC | CAT | ATT | GAA | GAA | GGC | 3223 |
| Glu | Leu | Gly | Cys | His | Val | Val | Asp | Val | Thr | Ser | His | Ile | Glu | Glu | Gly |      |
| 725 |     |     |     |     | 730 |     |     |     |     | 735 |     |     |     |     | 740 |      |
| TCC | TCT | GTT | GAT | AGG | CGT | GCG | AGA | AAG | AGG | TCC | TCT | GCG | GTG | TTC | ATG | 3271 |
| Ser | Ser | Val | Asp | Arg | Arg | Ala | Arg | Lys | Arg | Ser | Ser | Ala | Val | Phe | Met |      |
|     |     |     |     | 745 |     |     |     |     | 750 |     |     |     |     | 755 |     |      |
| CCA | CAA | AAA | CTT | GTC | AAT | TTA | TTA | CCA | CAA | TCG | TTC | AAC | GAC | GAA | CTG | 3319 |
| Pro | Gln | Lys | Leu | Val | Asn | Leu | Leu | Pro | Gln | Ser | Phe | Asn | Asp | Glu | Leu |      |
|     |     |     | 760 |     |     |     |     | 765 |     |     |     |     | 770 |     |     |      |
| TCG | TTG | GCC | CCT | GGC | AAG | GAA | TCA | GCC | ACG | CTG | TCG | GTT | GTT | TAC | ACT | 3367 |
| Ser | Leu | Ala | Pro | Gly | Lys | Glu | Ser | Ala | Thr | Leu | Ser | Val | Val | Tyr | Thr |      |
|     |     | 775 |     |     |     |     | 780 |     |     |     |     | 785 |     |     |     |      |
| CTA | GAC | TCA | TCT | ACT | TTA | AGG | ATT | AAA | TCT | ACT | TGG | GTA | GGC | GAA | TCT | 3415 |
| Leu | Asp | Ser | Ser | Thr | Leu | Arg | Ile | Lys | Ser | Thr | Trp | Val | Gly | Glu | Ser |      |
| 790 |     |     |     |     | 795 |     |     |     |     | 800 |     |     |     |     |     |      |
| ACA | ATT | TCC | CCC | TCA | AAC | ATC | TTG | TCT | TTA | GAA | CAA | TTA | GAC | GAA | AAA | 3463 |
| Thr | Ile | Ser | Pro | Ser | Asn | Ile | Leu | Ser | Leu | Glu | Gln | Leu | Asp | Glu | Lys |      |
| 805 |     |     |     |     | 810 |     |     |     |     | 815 |     |     |     |     | 820 |      |
| TTA | TCT | ACT | GGA | AGT | CCC | ACT | AGC | TAC | CTC | TCT | ACT | GTA | CAG | GAA | ATT | 3511 |
| Leu | Ser | Thr | Gly | Ser | Pro | Thr | Ser | Tyr | Leu | Ser | Thr | Val | Gln | Glu | Ile |      |
|     |     |     |     | 825 |     |     |     |     | 830 |     |     |     |     | 835 |     |      |
| GCT | AGA | TCA | TTT | TAT | GCT | AGA | AGA | ATA | AAT | GAT | CCA | GAA | GCT | ACA | TTA | 3559 |
| Ala | Arg | Ser | Phe | Tyr | Ala | Arg | Arg | Ile | Asn | Asp | Pro | Glu | Ala | Thr | Leu |      |

|     |     |     |     |     |     |     |     |     |     |     |     |     |     |     |     |      |
|---|---|---|---|---|---|---|---|---|---|---|---|---|---|---|---|---|
|     |     |     |     | 840 |     |     |     |     | 845 |     |     |     |     | 850 |     |      |
| CTT | CCC | ACC | CTG | TCC | TTA | TTG | GAA | AGC | TTG | GAT | GAC | GAA | AAA | GTT | AAG | 3607 |
| Leu | Pro | Thr | Leu | Ser | Leu | Leu | Glu | Ser | Leu | Asp | Asp | Glu | Lys | Val | Lys |      |
|     |     | 855 |     |     |     |     | 860 |     |     |     |     | 865 |     |     |     |      |
| GTT | GAC | TTG | AAC | ATC | CTG | GAT | AGA | ACT | TTA | GGC | TTT | GTT | GTA | ATT | AAT | 3655 |
| Val | Asp | Leu | Asn | Ile | Leu | Asp | Arg | Thr | Leu | Gly | Phe | Val | Val | Ile | Asn |      |
|     | 870 |     |     |     |     | 875 |     |     |     |     | 880 |     |     |     |     |      |
| GAG | ATT | AAA | AGA | AAG | GTC | AAC | TCC | ACT | GTT | GCA | GAG | AAA | ATT | TAC | ACC | 3703 |
| Glu | Ile | Lys | Arg | Lys | Val | Asn | Ser | Thr | Val | Ala | Glu | Lys | Ile | Tyr | Thr |      |
| 885 |     |     |     |     | 890 |     |     |     |     | 895 |     |     |     |     | 900 |      |
| AAA | CTT | GGT | GAT | CTA | GCT | CTT | TTG | AGA | AGG | CAG | ATG | CAA | CCC | ATT | GCA | 3751 |
| Lys | Leu | Gly | Asp | Leu | Ala | Leu | Leu | Arg | Arg | Gln | Met | Gln | Pro | Ile | Ala |      |
|     |     |     |     | 905 |     |     |     |     | 910 |     |     |     |     | 915 |     |      |
| ACC | AAG | ATG | GCG | TCA | TTT | AGA | AAG | AAA | ATT | CAA | AAT | TTT | GGT | TAC | AAT | 3799 |
| Thr | Lys | Met | Ala | Ser | Phe | Arg | Lys | Lys | Ile | Gln | Asn | Phe | Gly | Tyr | Asn |      |
|     |     |     |     | 920 |     |     |     |     | 925 |     |     |     |     | 930 |     |      |
| TTT | GAT | ACC | AAT | ACG | GCG | GAT | GAA | TTA | ATC | AAA | GGG | GTG | CTA | AAA | ATT | 3847 |
| Phe | Asp | Thr | Asn | Thr | Ala | Asp | Glu | Leu | Ile | Lys | Gly | Val | Leu | Lys | Ile |      |
|     |     | 935 |     |     |     |     | 940 |     |     |     |     | 945 |     |     |     |      |
| AAA | GAT | GAC | GAT | GTT | AGA | GTC | GGA | ATT | GAA | ATT | TTA | CTG | TTT | AAA | ACC | 3895 |
| Lys | Asp | Asp | Asp | Val | Arg | Val | Gly | Ile | Glu | Ile | Leu | Leu | Phe | Lys | Thr |      |
| 950 |     |     |     |     | 955 |     |     |     |     | 960 |     |     |     |     |     |      |
| ATG | CCA | AGA | GCT | AGA | TAC | TTT | ATT | GCT | GGC | AAA | GTA | GAC | CCG | GAC | CAA | 3943 |
| Met | Pro | Arg | Ala | Arg | Tyr | Phe | Ile | Ala | Gly | Lys | Val | Asp | Pro | Asp | Gln |      |
| 965 |     |     |     |     | 970 |     |     |     |     | 975 |     |     |     |     | 980 |      |
| TAT | GGG | CAT | TAT | GCC | TTG | AAC | CTA | CCT | ATC | TAC | ACA | CAT | TTC | ACA | GCG | 3991 |
| Tyr | Gly | His | Tyr | Ala | Leu | Asn | Leu | Pro | Ile | Tyr | Thr | His | Phe | Thr | Ala |      |
|     |     |     |     | 985 |     |     |     |     | 990 |     |     |     |     | 995 |     |      |
| CCA | ATG | AGA | AGA | TAC | GCT | GAT | CAT | GTC | GTT | CAT | AGG | CAA | TTA | AAG | GCC | 4039 |
| Pro | Met | Arg | Arg | Tyr | Ala | Asp | His | Val | Val | His | Arg | Gln | Leu | Lys | Ala |      |
|     |     |     |     | 1000|     |     |     |     | 1005|     |     |     |     | 1010|     |      |
| GTT | ATC | CAC | GAT | ACT | CCA | TAC | ACC | GAA | GAT | ATG | GAA | GCT | TTG | AAG | ATT | 4087 |
| Val | Ile | His | Asp | Thr | Pro | Tyr | Thr | Glu | Asp | Met | Glu | Ala | Leu | Lys | Ile |      |
|     |     |     |     | 1015|     |     |     |     | 1020|     |     |     |     | 1025|     |      |
| ACC | TCC | GAA | TAT | TGT | AAT | TTT | AAA | AAG | GAC | TGT | GCT | TAT | CAA | GCA | CAG | 4135 |
| Thr | Ser | Glu | Tyr | Cys | Asn | Phe | Lys | Lys | Asp | Cys | Ala | Tyr | Gln | Ala | Gln |      |
|     |     |     |     | 1030|     |     |     |     | 1035|     |     |     |     | 1040|     |      |
| GAA | CAA | GCA | ATT | CAT | CTA | TTG | TTG | TGT | AAA | ACA | ATC | AAC | GAC | ATG | GGA | 4183 |
| Glu | Gln | Ala | Ile | His | Leu | Leu | Leu | Cys | Lys | Thr | Ile | Asn | Asp | Met | Gly |      |
| 1045|     |     |     |     | 1050|     |     |     |     | 1055|     |     |     |     | 1060|      |
| AAT | ACT | ACA | GGA | CAA | TTA | TTA | ACA | ATG | GCT | ACT | GTC | TTA | CAA | GTT | TAC | 4231 |
| Asn | Thr | Thr | Gly | Gln | Leu | Leu | Thr | Met | Ala | Thr | Val | Leu | Gln | Val | Tyr |      |
|     |     |     |     | 1065|     |     |     |     | 1070|     |     |     |     | 1075|     |      |
| GAG | TCC | TCC | TTT | GAT | GTA | TTT | ATT | CCA | GAA | TTT | GGT | ATT | GAA | AAG | AGA | 4279 |
| Glu | Ser | Ser | Phe | Asp | Val | Phe | Ile | Pro | Glu | Phe | Gly | Ile | Glu | Lys | Arg |      |
|     |     |     |     | 1080|     |     |     |     | 1085|     |     |     |     | 1090|     |      |
| GTT | CAT | GGA | GAT | CAA | CTA | CCT | TTG | ATC | AAA | GCT | GAG | TTT | GAT | GGT | ACC | 4327 |
| Val | His | Gly | Asp | Gln | Leu | Pro | Leu | Ile | Lys | Ala | Glu | Phe | Asp | Gly | Thr |      |
|     |     |     |     | 1095|     |     |     |     | 1100|     |     |     |     | 1105|     |      |
| AAT | CGT | GTC | TTG | GAA | TTG | CAT | TGG | CAG | CCC | GGC | GTA | GAT | AGT | GCA | ACT | 4375 |
| Asn | Arg | Val | Leu | Glu | Leu | His | Trp | Gln | Pro | Gly | Val | Asp | Ser | Ala | Thr |      |
|     |     |     | 1110|     |     |     |     | 1115|     |     |     |     | 1120|     |     |      |
| TTT | ATA | CCA | GCA | GAT | GAA | AAA | AAT | CCA | AAA | TCC | TAT | AGA | AAT | TCC | ATT | 4423 |
| Phe | Ile | Pro | Ala | Asp | Glu | Lys | Asn | Pro | Lys | Ser | Tyr | Arg | Asn | Ser | Ile |      |
| 1125|     |     |     |     | 1130|     |     |     |     | 1135|     |     |     |     | 1140|      |
| AAG | AAC | AAA | TTC | AGA | TCC | ACA | GCC | GCT | GAG | ATT | GCG | AAT | ATT | GAA | CTA | 4471 |
| Lys | Asn | Lys | Phe | Arg | Ser | Thr | Ala | Ala | Glu | Ile | Ala | Asn | Ile | Glu | Leu |      |
|     |     |     |     | 1145|     |     |     |     | 1150|     |     |     |     | 1155|     |      |
| GAT | AAA | GAA | GCG | GAA | TCT | GAA | CCA | TTG | ATC | AGC | GAT | CCA | TTG | AGT | AAG | 4519 |
| Asp | Lys | Glu | Ala | Glu | Ser | Glu | Pro | Leu | Ile | Ser | Asp | Pro | Leu | Ser | Lys |      |

|  |  |  |  |  |  |  |  |  |  |  |  |  |  |  |  |
|--|--|--|--|--|--|--|--|--|--|--|--|--|--|--|--|
| | | | | | | 1160 | | | | | 1165 | | | | 1170 |

| GAA | CTC | AGC | GAT | TTG | CAT | CTA | ACA | GTA | CCA | AAT | TTA | AGG | CTA | CCA | TCT | 4567 |
|-----|-----|-----|-----|-----|-----|-----|-----|-----|-----|-----|-----|-----|-----|-----|-----|------|
| Glu | Leu | Ser | Asp | Leu | His | Leu | Thr | Val | Pro | Asn | Leu | Arg | Leu | Pro | Ser | |
| | | 1175 | | | | | 1180 | | | | | | 1185 | | | |

| GCA | AGC | GAC | AAC | AAG | CAA | AAT | GCT | TTA | GAA | AAA | TTC | ATT | TCT | ACT | ACT | 4615 |
|-----|-----|-----|-----|-----|-----|-----|-----|-----|-----|-----|-----|-----|-----|-----|-----|------|
| Ala | Ser | Asp | Asn | Lys | Gln | Asn | Ala | Leu | Glu | Lys | Phe | Ile | Ser | Thr | Thr | |
| 1190 | | | | | 1195 | | | | | | 1200 | | | | | |

| GAA | ACC | AGA | ATT | GAA | AAT | GAT | AAC | TAT | ATA | CAA | GAA | ATA | CAT | GAA | TTG | 4663 |
|-----|-----|-----|-----|-----|-----|-----|-----|-----|-----|-----|-----|-----|-----|-----|-----|------|
| Glu | Thr | Arg | Ile | Glu | Asn | Asp | Asn | Tyr | Ile | Gln | Glu | Ile | His | Glu | Leu | |
| 1205 | | | | | 1210 | | | | | 1215 | | | | | 1220 | |

| CAA | AAG | ATT | CCT | ATT | CTA | TTG | AGA | GCT | GAG | GTG | GGG | ATG | GCT | TTG | CCA | 4711 |
|-----|-----|-----|-----|-----|-----|-----|-----|-----|-----|-----|-----|-----|-----|-----|-----|------|
| Gln | Lys | Ile | Pro | Ile | Leu | Leu | Arg | Ala | Glu | Val | Gly | Met | Ala | Leu | Pro | |
| | | | | 1225 | | | | | 1230 | | | | | 1235 | | |

| TGT | TTA | ACC | GTC | CGT | GCA | TTA | AAT | CCA | TTC | ATG | AAG | AGG | GTA | | | 4753 |
|-----|-----|-----|-----|-----|-----|-----|-----|-----|-----|-----|-----|-----|-----|--|--|------|
| Cys | Leu | Thr | Val | Arg | Ala | Leu | Asn | Pro | Phe | Met | Lys | Arg | Val | | | |
| | | | 1240 | | | | | 1245 | | | | | 1250 | | | |

| TAATCTCTTC | TACCAATATC | GTCATTGCTG | TTTTTCTTGT | TTTTCACTTT | CGTTCTTTGG | 4813 |
|------------|------------|------------|------------|------------|------------|------|
| ATTGTGCTTC | ACCCCTCAGT | ATCCCTTCCC | TTTGTTTTA | TTTCCTGCGA | ACATTAACAA | 4873 |
| CTGCATGAAT | TTTGTACTTC | TCCTTTTAAT | CCACGTTCCG | GTAAGGCATC | ATCCAAATTT | 4933 |
| TTTTATTCGA | CCTCGTTAAG | TCATATATTT | TTTCCCAAAA | ATACATAAAA | CAATAATGCA | 4993 |
| GCCTTCTTTT | CAATATTTAC | AACTTTTCAA | TTTATATTGT | CTTTTGTTAT | TTATACTCTT | 5053 |
| ATATATTAAA | TTTATTCCGT | TACTAAATAC | CCTTTTGCTG | TACAAATATC | ATCAAAGAGA | 5113 |
| AGTACTGAAA | GCTTACTTTT | TATGCGCTGG | GTAATTTTTC | CGGAAACAAT | AACGAAATCA | 5173 |
| TCGTCGAGCA | ATTTTGCTCG | TACTTCAGAA | ACTACTGCGT | AAACATTTGA | GGTCGTACAA | 5233 |
| TAAGTAGATA | GAAATAAATA | AACCAATTTT | TCGTCAGCGT | TAATCTGTA | GCCAAAGATT | 5293 |
| TGTGGTATTC | TCACAGTTTG | AATAATATTC | AGCTACTTCA | TCAAGTAGTT | TTTTCAATA | 5353 |
| GGAGATTCAC | GGTTCAATAA | GTGCATTGAT | TATGTTCGAC | CAATTAGCAG | TCTTTACCCC | 5413 |
| TCAAGGTCAA | GTACTTTACC | AATATAACTG | TTTAGGAAAA | AAGTTTTCTG | AAATACAAAT | 5473 |
| TAACAGCTTT | ATATCCCAGC | TGATTACTTC | CCCAGTAACT | AGAAAAGAAA | GTGTTGCAAA | 5533 |
| CGCAAATACA | GACGGATTTG | ATTTCAATCT | TTTAACAATC | AACAGCGAAC | ACAAAAATTC | 5593 |
| TCCTTCATTT | AATGCACTAT | TTTATTTGAA | TAAGCAACCA | GAATTGTATT | TCGTAGTGAC | 5653 |
| TTTTGCCGAG | CAGACTTTAG | AGCTTAATCA | AGAAACTCAA | CAAACACTTG | CACTGGTGTT | 5713 |
| AAAACTCTGG | AACTCATTGC | ATTTAAGTGA | ATCCATTCTA | AAAAATCGTC | AGGGCCAAAA | 5773 |
| CGAAAAGAAC | AAGCATAACT | ACGTCGATAT | TCTTCAGGGA | ATTGAAGACG | ACCTGAAGAA | 5833 |
| ATTTGAGCAA | TATTTTAGGA | TAAAATATGA | AGAGTCAATA | AAACAAGACC | ATATCAATCC | 5893 |
| AGATAATTTT | ACCAAAAATG | GATCAGTACC | CCAATCGCAT | AATAAAATA | CCAAGAAAAA | 5953 |
| ATTGAGGGAT | ACAAAAGGTA | AGAAGCAATC | TACAGGAAAT | GTTGGTAGTG | GGTAGTAAAG | 6013 |
| TGGGGCCGTG | ATGGTGG | | | | | 6030 |

( 2 ) INFORMATION FOR SEQ ID NO:9:

( i ) SEQUENCE CHARACTERISTICS:
        ( A ) LENGTH: 1250 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Ser | Lys | Asn | Ser | Asn | Val | Asn | Asn | Asn | Arg | Ser | Gln | Glu | Pro | Asn |
|-----|-----|-----|-----|-----|-----|-----|-----|-----|-----|-----|-----|-----|-----|-----|-----|
| 1 | | | | 5 | | | | | 10 | | | | | 15 | |

| | | | | | | | | | | | | | | |
|---|---|---|---|---|---|---|---|---|---|---|---|---|---|---|
|Asn|Met|Phe|Val|Gln|Thr|Thr|Gly|Gly|Gly|Lys|Asn|Ala|Pro|Lys|Gln|
| | | |20| | | |25| | |  |30| | | |
|Ile|His|Val|Ala|His|Arg|Arg|Ser|Gln|Ser|Glu|Leu|Thr|Asn|Leu|Met|
| | |35| | | |40| | | |45| | | | |
|Ile|Glu|Gln|Phe|Thr|Leu|Gln|Lys|Gln|Leu|Glu|Gln|Val|Gln|Ala|Gln|
| |50| | | |55| | | | |60| | | | |
|Gln|Gln|Gln|Leu|Met|Ala|Gln|Gln|Gln|Leu|Ala|Gln|Gln|Thr|Gly|
|65| | | |70| | | |75| | | | |80|
|Gln|Tyr|Leu|Ser|Gly|Asn|Ser|Gly|Ser|Asn|Asn|His|Phe|Thr|Pro|Gln|
| | | |85| | | |90| | | |95| |
|Pro|Pro|His|Pro|His|Tyr|Asn|Ser|Asn|Gly|Asn|Ser|Pro|Gly|Met|Ser|
| | |100| | | |105| | | |110| |
|Ala|Gly|Gly|Ser|Arg|Ser|Arg|Thr|His|Ser|Arg|Asn|Asn|Ser|Gly|Tyr|
| |115| | | |120| | | |125| |
|Tyr|His|Asn|Ser|Tyr|Asp|Asn|Asn|Asn|Ser|Asn|Asn|Pro|Gly|Ser|
| |130| | | |135| | | |140| |
|Asn|Ser|His|Arg|Lys|Thr|Ser|Ser|Gln|Ser|Ser|Ile|Tyr|Gly|His|Ser|
|145| | | |150| | | |155| | |160|
|Arg|Arg|His|Ser|Leu|Gly|Leu|Asn|Glu|Ala|Lys|Lys|Ala|Ala|Ala|Glu|
| | |165| | | |170| | | |175|
|Glu|Gln|Ala|Lys|Arg|Ile|Ser|Gly|Gly|Glu|Ala|Gly|Val|Thr|Val|Lys|
| | |180| | | |185| | | |190|
|Ile|Asp|Ser|Val|Gln|Ala|Asp|Ser|Gly|Ser|Asn|Ser|Thr|Thr|Glu|Gln|
| |195| | | |200| | | |205|
|Ser|Asp|Phe|Lys|Phe|Pro|Pro|Pro|Asn|Ala|His|Gln|Gly|His|Arg|
| |210| | | |215| | | |220|
|Arg|Ala|Thr|Ser|Asn|Leu|Ser|Pro|Pro|Ser|Phe|Lys|Phe|Pro|Pro|Asn|
|225| | | |230| | | |235| | |240|
|Ser|His|Gly|Asp|Asn|Asp|Asp|Glu|Phe|Ile|Ala|Thr|Ser|Ser|Thr|His|
| | |245| | | |250| | | |255|
|Arg|Arg|Ser|Lys|Thr|Arg|Asn|Asn|Glu|Tyr|Ser|Pro|Gly|Ile|Asn|Ser|
| |260| | | |265| | | |270|
|Asn|Trp|Arg|Asn|Gln|Ser|Gln|Gln|Pro|Gln|Gln|Gln|Leu|Ser|Pro|Phe|
| |275| | | |280| | | |285|
|Arg|His|Arg|Gly|Ser|Asn|Ser|Arg|Asp|Tyr|Asn|Ser|Phe|Asn|Thr|Leu|
| |290| | | |295| | | |300|
|Glu|Pro|Pro|Ala|Ile|Phe|Gln|Gln|Gly|His|Lys|His|Arg|Ala|Ser|Asn|
|305| | | |310| | | |315| | |320|
|Ser|Ser|Val|His|Ser|Phe|Ser|Ser|Gln|Gly|Asn|Asn|Asn|Gly|Gly|Gly|
| | |325| | | |330| | | |335|
|Arg|Lys|Ser|Leu|Phe|Ala|Pro|Tyr|Leu|Pro|Gln|Ala|Asn|Ile|Pro|Glu|
| | |340| | | |345| | | |350|
|Leu|Ile|Gln|Glu|Gly|Arg|Leu|Val|Ala|Gly|Ile|Leu|Arg|Val|Asn|Lys|
| | |355| | | |360| | | |365|
|Lys|Asn|Arg|Ser|Asp|Ala|Trp|Val|Ser|Thr|Asp|Gly|Ala|Leu|Asp|Ala|
| | |370| | | |375| | | |380|
|Asp|Ile|Tyr|Ile|Cys|Gly|Ser|Lys|Asp|Arg|Asn|Arg|Ala|Leu|Glu|Gly|
|385| | | |390| | | |395| | |400|
|Asp|Leu|Val|Ala|Val|Glu|Leu|Leu|Val|Val|Asp|Val|Trp|Glu|Ser|
| | | |405| | | |410| | | |415|
|Lys|Lys|Glu|Lys|Glu|Glu|Lys|Lys|Arg|Arg|Lys|Asp|Ala|Ser|Met|Gln|
| | | |420| | | |425| | | |430|
|His|Asp|Leu|Ile|Pro|Leu|Asn|Ser|Ser|Asp|Asp|Tyr|His|Asn|Asp|Ala|

```
                    435                          440                          445
Ser  Val  Thr  Ala  Ala  Thr  Ser  Asn  Asn  Phe  Leu  Ser  Ser  Pro  Ser  Ser
     450                      455                      460
Ser  Asp  Ser  Leu  Ser  Lys  Asp  Asp  Leu  Ser  Val  Arg  Arg  Lys  Arg  Ser
465                           470                      475                     480
Ser  Thr  Ile  Asn  Asn  Asp  Ser  Asp  Ser  Leu  Ser  Ser  Pro  Thr  Lys  Ser
               485                      490                           495
Gly  Val  Arg  Arg  Arg  Ser  Ser  Leu  Lys  Gln  Arg  Pro  Thr  Gln  Lys  Lys
               500                      505                           510
Asn  Asp  Asp  Val  Glu  Val  Glu  Gly  Gln  Ser  Leu  Leu  Leu  Val  Glu  Glu
          515                      520                      525
Glu  Glu  Ile  Asn  Asp  Lys  Tyr  Lys  Pro  Leu  Tyr  Ala  Gly  His  Val  Val
          530                      535                      540
Ala  Val  Leu  Asp  Arg  Ile  Pro  Gly  Gln  Leu  Phe  Ser  Gly  Thr  Leu  Gly
545                           550                      555                     560
Leu  Leu  Arg  Pro  Ser  Gln  Gln  Ala  Asn  Ser  Asp  Asn  Asn  Lys  Pro  Pro
                    565                      570                      575
Gln  Ser  Pro  Lys  Ile  Ala  Trp  Phe  Lys  Pro  Thr  Asp  Lys  Lys  Val  Pro
               580                      585                      590
Leu  Ile  Ala  Ile  Pro  Thr  Glu  Leu  Ala  Pro  Lys  Asp  Phe  Val  Glu  Asn
          595                      600                      605
Ala  Asp  Lys  Tyr  Ser  Glu  Lys  Leu  Phe  Val  Ala  Ser  Ile  Lys  Arg  Trp
     610                           615                      620
Pro  Ile  Thr  Ser  Leu  His  Pro  Phe  Gly  Ile  Leu  Val  Ser  Glu  Leu  Gly
625                           630                      635                     640
Asp  Ile  His  Asp  Pro  Asp  Thr  Glu  Ile  Asp  Ser  Ile  Leu  Arg  Asp  Asn
                    645                      650                      655
Asn  Phe  Leu  Ser  Asn  Glu  Tyr  Leu  Asp  Gln  Lys  Asn  Pro  Gln  Lys  Glu
               660                      665                      670
Lys  Pro  Ser  Phe  Gln  Pro  Leu  Pro  Leu  Thr  Ala  Glu  Ser  Leu  Glu  Tyr
          675                      680                      685
Arg  Arg  Asn  Phe  Thr  Asp  Thr  Asn  Glu  Tyr  Asn  Ile  Phe  Ala  Ile  Ser
     690                           695                      700
Glu  Leu  Gly  Trp  Val  Ser  Glu  Phe  Ala  Leu  His  Val  Arg  Asn  Asn  Gly
705                                710                      715                720
Asn  Gly  Thr  Leu  Glu  Leu  Gly  Cys  His  Val  Asp  Val  Thr  Ser  His
                    725                      730                           735
Ile  Glu  Glu  Gly  Ser  Ser  Val  Asp  Arg  Arg  Ala  Arg  Lys  Arg  Ser  Ser
               740                      745                      750
Ala  Val  Phe  Met  Pro  Gln  Lys  Leu  Val  Asn  Leu  Leu  Pro  Gln  Ser  Phe
          755                      760                      765
Asn  Asp  Glu  Leu  Ser  Leu  Ala  Pro  Gly  Lys  Glu  Ser  Ala  Thr  Leu  Ser
     770                      775                      780
Val  Val  Tyr  Thr  Leu  Asp  Ser  Ser  Thr  Leu  Arg  Ile  Lys  Ser  Thr  Trp
785                           790                      795                     800
Val  Gly  Glu  Ser  Thr  Ile  Ser  Pro  Ser  Asn  Ile  Leu  Ser  Leu  Glu  Gln
                    805                      810                      815
Leu  Asp  Glu  Lys  Leu  Ser  Thr  Gly  Ser  Pro  Thr  Ser  Tyr  Leu  Ser  Thr
               820                      825                      830
Val  Gln  Glu  Ile  Ala  Arg  Ser  Phe  Tyr  Ala  Arg  Arg  Ile  Asn  Asp  Pro
          835                      840                      845
Glu  Ala  Thr  Leu  Leu  Pro  Thr  Leu  Ser  Leu  Leu  Glu  Ser  Leu  Asp  Asp
850                           855                      860
```

| | | | | | | | | | | | | | | |
|---|---|---|---|---|---|---|---|---|---|---|---|---|---|---|
| Glu | Lys | Val | Lys | Val | Asp | Leu | Asn | Ile | Leu | Asp | Arg | Thr | Leu | Gly | Phe |
| 865 | | | | 870 | | | | 875 | | | | | | 880 |
| Val | Val | Ile | Asn | Glu | Ile | Lys | Arg | Lys | Val | Asn | Ser | Thr | Val | Ala | Glu |
| | | | | 885 | | | | 890 | | | | | 895 | | |
| Lys | Ile | Tyr | Thr | Lys | Leu | Gly | Asp | Leu | Ala | Leu | Leu | Arg | Arg | Gln | Met |
| | | | 900 | | | | 905 | | | | | 910 | | | |
| Gln | Pro | Ile | Ala | Thr | Lys | Met | Ala | Ser | Phe | Arg | Lys | Lys | Ile | Gln | Asn |
| | | 915 | | | | 920 | | | | | 925 | | | | |
| Phe | Gly | Tyr | Asn | Phe | Asp | Thr | Asn | Thr | Ala | Asp | Glu | Leu | Ile | Lys | Gly |
| 930 | | | | | 935 | | | | | 940 | | | | | |
| Val | Leu | Lys | Ile | Lys | Asp | Asp | Val | Arg | Val | Gly | Ile | Glu | Ile | Leu |
| 945 | | | | | 950 | | | | 955 | | | | | 960 |
| Leu | Phe | Lys | Thr | Met | Pro | Arg | Ala | Arg | Tyr | Phe | Ile | Ala | Gly | Lys | Val |
| | | | | 965 | | | | | 970 | | | | | 975 | |
| Asp | Pro | Asp | Gln | Tyr | Gly | His | Tyr | Ala | Leu | Asn | Leu | Pro | Ile | Tyr | Thr |
| | | | 980 | | | | | 985 | | | | | 990 | | |
| His | Phe | Thr | Ala | Pro | Met | Arg | Arg | Tyr | Ala | Asp | His | Val | Val | His | Arg |
| | | 995 | | | | | 1000 | | | | | 1005 | | | |
| Gln | Leu | Lys | Ala | Val | Ile | His | Asp | Thr | Pro | Tyr | Thr | Glu | Asp | Met | Glu |
| | | 1010 | | | | 1015 | | | | | 1020 | | | | |
| Ala | Leu | Lys | Ile | Thr | Ser | Glu | Tyr | Cys | Asn | Phe | Lys | Lys | Asp | Cys | Ala |
| 1025 | | | | | 1030 | | | | | 1035 | | | | | 1040 |
| Tyr | Gln | Ala | Gln | Glu | Gln | Ala | Ile | His | Leu | Leu | Leu | Cys | Lys | Thr | Ile |
| | | | | 1045 | | | | | 1050 | | | | | 1055 | |
| Asn | Asp | Met | Gly | Asn | Thr | Thr | Gly | Gln | Leu | Leu | Thr | Met | Ala | Thr | Val |
| | | | 1060 | | | | | 1065 | | | | | 1070 | | |
| Leu | Gln | Val | Tyr | Glu | Ser | Ser | Phe | Asp | Val | Phe | Ile | Pro | Glu | Phe | Gly |
| | | | | 1075 | | | | | 1080 | | | | | 1085 | |
| Ile | Glu | Lys | Arg | Val | His | Gly | Asp | Gln | Leu | Pro | Leu | Ile | Lys | Ala | Glu |
| | | | | 1090 | | | | | 1095 | | | | | 1100 | |
| Phe | Asp | Gly | Thr | Asn | Arg | Val | Leu | Glu | Leu | His | Trp | Gln | Pro | Gly | Val |
| 1105 | | | | | 1110 | | | | | 1115 | | | | | 1120 |
| Asp | Ser | Ala | Thr | Phe | Ile | Pro | Ala | Asp | Glu | Lys | Asn | Pro | Lys | Ser | Tyr |
| | | | | 1125 | | | | | 1130 | | | | | 1135 | |
| Arg | Asn | Ser | Ile | Lys | Asn | Lys | Phe | Arg | Ser | Thr | Ala | Ala | Glu | Ile | Ala |
| | | | | 1140 | | | | | 1145 | | | | | 1150 | |
| Asn | Ile | Glu | Leu | Asp | Lys | Glu | Ala | Glu | Ser | Glu | Pro | Leu | Ile | Ser | Asp |
| | | | | 1155 | | | | | 1160 | | | | | 1165 | |
| Pro | Leu | Ser | Lys | Glu | Leu | Ser | Asp | Leu | His | Leu | Thr | Val | Pro | Asn | Leu |
| | | | | 1170 | | | | | 1175 | | | | | 1180 | |
| Arg | Leu | Pro | Ser | Ala | Ser | Asp | Asn | Lys | Gln | Asn | Ala | Leu | Glu | Lys | Phe |
| 1185 | | | | | 1190 | | | | | 1195 | | | | | 1200 |
| Ile | Ser | Thr | Thr | Glu | Thr | Arg | Ile | Glu | Asn | Asp | Asn | Tyr | Ile | Gln | Glu |
| | | | | 1205 | | | | | 1210 | | | | | 1215 | |
| Ile | His | Glu | Leu | Gln | Lys | Ile | Pro | Ile | Leu | Leu | Arg | Ala | Glu | Val | Gly |
| | | | | 1220 | | | | | 1225 | | | | | 1230 | |
| Met | Ala | Leu | Pro | Cys | Leu | Thr | Val | Arg | Ala | Leu | Asn | Pro | Phe | Met | Lys |
| | | | | 1235 | | | | | 1240 | | | | | 1245 | |
| Arg | Val |
| | 1250 |

(2) INFORMATION FOR SEQ ID NO:10:

(i) SEQUENCE CHARACTERISTICS:
        (A) LENGTH: 168 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:10:

```
Ile Pro Pro Ala Pro Arg Gly Val Pro Gln Ile Glu Val Thr Phe Glu
  1               5                  10                  15
Ile Asp Val Asn Gly Ile Leu Arg Val Thr Ala Glu Asp Lys Gly Thr
                 20                  25                  30
Gly Asn Lys Asn Lys Ile Thr Ile Thr Asn Asp Gln Asn Arg Leu Thr
             35                  40                  45
Pro Glu Glu Ile Glu Arg Met Val Asn Asp Ala Glu Lys Phe Ala Glu
         50                  55                  60
Glu Asp Lys Lys Leu Lys Glu Arg Ile Asp Thr Arg Asn Glu Leu Glu
 65                  70                  75                  80
Ser Tyr Ala Tyr Ser Leu Lys Asn Gln Ile Gly Asp Lys Glu Lys Leu
                 85                  90                  95
Gly Gly Lys Leu Ser Ser Glu Gly Lys Glu Thr Met Glu Lys Ala Val
            100                 105                 110
Glu Glu Lys Ile Glu Trp Leu Glu Ser His Gln Asp Ala Asp Ile Glu
            115                 120                 125
Asp Phe Lys Ala Lys Lys Lys Glu Leu Glu Glu Ile Val Gln Pro Ile
        130                 135                 140
Ile Ser Lys Leu Tyr Gly Ser Gly Gly Pro Pro Thr Gly Glu Glu
145                 150                 155                 160
Asp Thr Ser Glu Lys Asp Glu Leu
                165
```

(2) INFORMATION FOR SEQ ID NO:11:

(i) SEQUENCE CHARACTERISTICS:
(A) LENGTH: 654 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:11:

```
Met Lys Phe Pro Met Val Ala Ala Ala Leu Leu Leu Leu Cys Ala Val
  1               5                  10                  15
Arg Ala Glu Glu Glu Asp Lys Lys Glu Asp Val Gly Thr Val Val Gly
                 20                  25                  30
Ile Asp Leu Gly Thr Thr Tyr Ser Cys Val Gly Val Phe Lys Asn Gly
             35                  40                  45
Arg Val Glu Ile Ile Ala Asn Asp Gln Gly Asn Arg Ile Thr Pro Ser
         50                  55                  60
Tyr Val Ala Phe Thr Pro Glu Gly Glu Arg Leu Ile Gly Asp Ala Ala
 65                  70                  75                  80
Lys Asn Gln Leu Thr Ser Asn Pro Glu Asn Thr Val Phe Asp Ala Lys
                 85                  90                  95
Arg Leu Ile Gly Arg Thr Trp Asn Asp Pro Ser Val Gln Gln Asp Ile
            100                 105                 110
Lys Phe Leu Pro Phe Lys Val Val Glu Lys Lys Thr Lys Pro Tyr Ile
        115                 120                 125
Gln Val Asp Ile Gly Gly Gly Gln Thr Lys Thr Phe Ala Pro Glu Glu
        130                 135                 140
```

```
Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165             170             175

Asn Asp Ala Gln Arg Gln Ala Thr Lys Asp Ala Gly Thr Ile Ala Gly
            180             185             190

Leu Asn Val Met Arg Ile Ile Asn Glu Pro Thr Ala Ala Ala Ile Ala
            195             200             205

Tyr Gly Leu Asp Lys Arg Glu Gly Glu Lys Asn Ile Leu Val Phe Asp
    210             215             220

Leu Gly Gly Gly Thr Phe Asp Val Ser Leu Leu Thr Ile Asp Asn Gly
225             230             235             240

Val Phe Glu Val Val Ala Thr Asn Gly Asp Thr His Leu Gly Gly Glu
                245             250             255

Asp Phe Asp Gln Arg Val Met Glu His Phe Ile Lys Leu Tyr Lys Lys
            260             265             270

Lys Thr Gly Lys Asp Val Arg Lys Asp Asn Arg Ala Val Gln Lys Leu
        275             280             285

Arg Arg Glu Val Glu Lys Ala Lys Arg Ala Leu Ser Ser Gln His Gln
    290             295             300

Ala Arg Ile Glu Ile Glu Ser Phe Phe Glu Gly Glu Asp Phe Ser Glu
305             310             315             320

Thr Leu Thr Arg Ala Lys Phe Glu Glu Leu Asn Met Asp Leu Phe Arg
                325             330             335

Ser Thr Met Lys Pro Val Gln Lys Val Leu Glu Asp Ser Asp Leu Lys
            340             345             350

Lys Ser Asp Ile Asp Glu Ile Val Leu Val Gly Gly Ser Thr Arg Ile
        355             360             365

Pro Lys Ile Gln Gln Leu Val Lys Glu Phe Phe Asn Gly Lys Glu Pro
    370             375             380

Ser Arg Gly Ile Asn Pro Asp Glu Ala Val Ala Tyr Gly Ala Ala Val
385             390             395             400

Gln Ala Gly Val Leu Ser Gly Asp Gln Asp Thr Gly Asp Leu Val Leu
                405             410             415

Leu Asp Val Cys Pro Leu Thr Leu Gly Ile Glu Thr Val Gly Gly Val
            420             425             430

Met Thr Lys Leu Ile Pro Arg Asn Thr Val Val Pro Thr Lys Lys Ser
        435             440             445

Gln Ile Phe Ser Thr Ala Ser Asp Asn Gln Pro Thr Val Thr Ile Lys
    450             455             460

Val Tyr Glu Gly Glu Arg Pro Leu Thr Lys Asp Asn His Leu Leu Gly
465             470             475             480

Thr Phe Asp Leu Thr Gly Ile Pro Pro Ala Pro Arg Gly Val Pro Gln
                485             490             495

Ile Glu Val Thr Phe Glu Ile Asp Val Asn Gly Ile Leu Arg Val Thr
            500             505             510

Ala Glu Asp Lys Gly Thr Gly Asn Lys Asn Lys Ile Thr Ile Thr Asn
        515             520             525

Asp Gln Asn Arg Leu Thr Pro Glu Glu Ile Glu Arg Met Val Asn Asp
    530             535             540

Ala Glu Lys Phe Ala Glu Glu Asp Lys Lys Leu Lys Glu Arg Ile Asp
545             550             555             560

Thr Arg Asn Glu Leu Glu Ser Tyr Ala Tyr Ser Leu Lys Asn Gln Ile
```

|  |  |  |  | 565 |  |  |  | 570 |  |  |  | 575 |  |
|---|---|---|---|---|---|---|---|---|---|---|---|---|---|
| Gly | Asp | Lys | Glu | Lys | Leu | Gly | Gly | Lys | Leu | Ser | Ser | Glu | Asp | Lys | Glu |
|  |  |  | 580 |  |  |  |  | 585 |  |  |  |  | 590 |  |  |
| Thr | Met | Glu | Lys | Ala | Val | Glu | Glu | Lys | Ile | Glu | Trp | Leu | Glu | Ser | His |
|  |  | 595 |  |  |  |  | 600 |  |  |  |  | 605 |  |  |  |
| Gln | Asp | Ala | Asp | Ile | Glu | Asp | Phe | Lys | Ala | Lys | Lys | Lys | Glu | Leu | Glu |
|  | 610 |  |  |  |  | 615 |  |  |  |  | 620 |  |  |  |  |
| Glu | Ile | Val | Gln | Pro | Ile | Ile | Ser | Lys | Leu | Tyr | Gly | Ser | Ala | Gly | Pro |
| 625 |  |  |  |  | 630 |  |  |  |  | 635 |  |  |  |  | 640 |
| Pro | Pro | Thr | Gly | Glu | Glu | Asp | Thr | Ser | Glu | Lys | Asp | Glu | Leu |  |  |
|  |  |  |  | 645 |  |  |  |  | 650 |  |  |  |  |  |  |

( 2 ) INFORMATION FOR SEQ ID NO:12:

( i ) SEQUENCE CHARACTERISTICS:
        ( A ) LENGTH: 5470 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: exon
        ( B ) LOCATION: 593..715

( i x ) FEATURE:
        ( A ) NAME/KEY: exon
        ( B ) LOCATION: 806..1036

( i x ) FEATURE:
        ( A ) NAME/KEY: exon
        ( B ) LOCATION: 1402..1539

( i x ) FEATURE:
        ( A ) NAME/KEY: exon
        ( B ) LOCATION: 2175..2289

( i x ) FEATURE:
        ( A ) NAME/KEY: exon
        ( B ) LOCATION: 2378..2764

( i x ) FEATURE:
        ( A ) NAME/KEY: exon
        ( B ) LOCATION: 2878..3115

( i x ) FEATURE:
        ( A ) NAME/KEY: exon
        ( B ) LOCATION: 3400..3568

( i x ) FEATURE:
        ( A ) NAME/KEY: exon
        ( B ) LOCATION: 4535..5095

( x i ) SEQUENCE DESCRIPTION: SEQ ID NO:12:

| CCCGGGGTCA | CTCCTGCTGG | ACCTACTCCG | ACCCCCTAGG | CCGGGAGTGA | AGGCGGGACT | 60 |
|---|---|---|---|---|---|---|
| TGTGCGGTTA | CCAGCGGAAA | TGCCTCGGGG | TCAGAAGTCG | CAGGAGAGAT | AGACAGCTGC | 120 |
| TGAACCAATG | GGACCAGCGG | ATGGGCGGA | TGTTATCTAC | CATTGGTGAA | CGTTAGAAAC | 180 |
| GAATAGCAGC | CAATGAATCA | GCTGGGGGGG | CGGAGCAGTG | ACGTTTATTG | CGGAGGGGC | 240 |
| CGCTTCGAAT | CGGCGGCGGC | CAGCTTGGTG | GCCTGGGCCA | ATGAACGGCC | TCCAACGAGC | 300 |
| AGGGCCTTCA | CCAATCGGCG | GCCTCCACGA | CGGGGCTGGG | GGAGGGTATA | TAAGCCGAGT | 360 |
| AGGCGACGGT | GAGGTCGACG | CCGGCCAAGA | CAGCACAGAC | AGATTGACCT | ATTGGGGTGT | 420 |
| TTCGCGAGTG | TGAGAGGGAA | GCGCCGCGGC | CTGTATTTCT | AGACCTGCCC | TTCGCCTGGT | 480 |
| TCGTGGCGCC | TTGTGACCCC | GGGCCCCTGC | CGCCTGCAAG | TCGAAATTGC | GCTGTGCTCC | 540 |

```
TGTGCTACGG  CCTGTGGCTG  GACTGCCTGC  TGCTGCCCAA  CTGGCTGGCA  AGATGAAGCT   600
CTCCCTGGTG  GCCGCGATGC  TGCTGCTGCT  CAGCGCGGCG  CGGGCCGAGG  AGGAGGACAA   660
GAAGGAGGAC  GTGGGCACGG  TGGTCGGCAT  CGACTTGGGG  ACCACCTACT  CCTGGTAAGT   720
GGGGTTGCGG  ATGAGGGGA   CGGGGCGTGG  CGCTGGCTGG  CGTGAGAAGT  GCGGTGCTGA   780
TGTCCCTCTG  TCGGGTTTTT  GCAGCGTCGG  CGTGTTCAAG  AACGGCCGCG  TGGAGATCAT   840
CGCCAACGAT  CAGGGCAACC  GCATCACGCC  GTCCTATGTC  GCCTTCACTC  CTGAAGGGGA   900
ACGTCTGATT  GGCGATGCCG  CCAAGAACCA  GCTCACCTCC  AACCCCGAGA  ACACGGTCTT   960
TGACGCCAAG  CGGCTCATCG  GCCGCACGTG  GAATGACCCG  TCTGTGCAGC  AGGACATCAA  1020
GTTCTTGCCG  TTCAAGGTTC  GACCGGTTTT  CCTCATCCAG  TTAGAGAACG  GGTGGGTGGT  1080
GGGAGTATTT  AGAGTTATAA  GTCTCTGGAA  AAGTGTTGAG  ACAACAGTTG  AAGGTTATAG  1140
ACATGATGTA  TGTAATAACT  TTAATACTAT  TAGTATGTTA  CAAAACTTAA  GACAGTTGCT  1200
GTCGTACTGT  CTACGATAGT  TTAGGAATAA  AAGACCGATT  AAAACTGAAC  TTTGTAAGAC  1260
ACCTATACTC  CCTGAAGTAT  TTCTAGTCAA  TTTGCAGCCC  CAAGGGACCA  AAATAAACCA  1320
AATTGTGGGG  ATGGTAGTGG  GTCTTTTAAA  CTTTGAGATG  TCATTGTATC  TGTGTCTGAA  1380
AACAATAATT  CTTTAAAATA  GGTGGTTGAA  AAGAAAACTA  AACCATACAT  TCAAGTTGAT  1440
ATTGGAGGTG  GGCAAACAAA  GACATTTGCT  CCTGAAGAAA  TTTCTGCCAT  GGTTCTCACT  1500
AAAATGAAAG  AAACCGCTGA  GGCTTATTTG  GGAAAGAAGG  TAAATATTTC  TAGAACAATG  1560
TTAAGTATTT  TTTGATCATT  AGTATTCTCG  GTTGGCTGTT  ATGTATAGAA  GCCTTCGTGA  1620
AGGGTTTCAA  AAATTTTAAT  CAGAATGGTA  TTCATGCTTG  TCACGGTTTA  ATTATTGAGT  1680
CCCTTTACTA  TAAGCCAAAC  AAAAATAGAC  TTTTCATGTA  TTATTTAATG  CTTACAATTC  1740
CAGGAACAAT  AAAATTTTAT  ATGTTGTATT  CATCAATAAT  TGGCTTAAAA  ACTAAAGTGA  1800
TGGTTTGACT  GTAATTTTTT  TTTTTGAGA   TGGAGTCTTG  CTCTGTTGCC  CAGGCTGGAC  1860
TGCAGTGGCA  CGATCTCAGC  TCACTGCAAC  CTCTGCCTCC  CGGGTTAAGC  AGCTCTCCTG  1920
CCTCAGCCTC  CAAGTAATGG  AACGACAGGC  ACACCACCAC  AGCTGGCTAA  TTTTTTTTTT  1980
TTTTTTTAAT  TTTCAGTAGA  GACAGGGTTT  CTCCACATTG  CCAGGCTGGT  CTTGAAATCC  2040
TGCCCTCAGG  TTGATCCTCC  TGCCTAGCCT  CCCAAAGTGC  TGGATTATAG  GCAGAAGCCA  2100
CCGCCTGGCC  AGACTGTAAT  TTAAATAAGG  GTTAAACTAT  GTGACAATAC  ACTTAATTAT  2160
CTTTATCCTT  TTAGGTTACC  CATGCAGTTG  TTACTGTACC  AGCCTATTTT  AATGATGCCC  2220
AACGCCAAGC  AACCAAAGAC  GCTGGAACTA  TTGCTGGCCT  AAATGTTATG  AGGATCATCA  2280
ACGAGCCGTA  AGTATGAAAT  TCAGGGATAC  GGCATATTTG  CCAAATAGTG  GAAATGTGAA  2340
GTACTGACAA  AACTTTTCCC  TTTTTCAATC  TAATAGTACG  GCAGCTGCTA  TTGCTTATGG  2400
CCTGGATAAG  AGGGAGGGGG  AGAAGAACAT  CCTGGTGTTT  GACCTGGGTG  GCGGAACCTT  2460
CGATGTGTCT  CTTCTCACCA  TTGACAATGG  TGTCTTCGAA  GTTGTGGCCA  CTAATGGAGA  2520
TACTCATCTG  GGTGGAGAAG  ACTTTGACCA  GCGTGTCATG  GAACACTTCA  TCAAACTGTA  2580
CAAAAGAAG   ACGGGCAAAG  ATGTCAGGAA  GGACAATAGA  GCTGTGCAGA  AACTCCGGCG  2640
CGAGGTAGAA  AAGGCCAAGG  CCCTGTCTTC  TCAGCATCAA  GCAAGAATTG  AAATTGAGTC  2700
CTTCTATGAA  GGAGAAGACT  TTTCTGAGAC  CCTGACTCGG  GCCAAATTTG  AAGAGCTCAA  2760
CATGGTATGT  TCCTTGTTTT  CTGCTTTGCT  AATGAGATCT  CCTTAGACTC  TGAATTCAGG  2820
ACATTGCATC  TAGATACTTA  GATAACAGAC  ATCACAGTAA  CCATGTCTTT  TTTCTAGGAT  2880
CTGTTCCGGT  CTACTATGAA  GCCCGTCCAG  AAAGTGTTGG  AAGATTCTGA  TTTGAAGAAG  2940
```

| | | | | | |
|---|---|---|---|---|---|
| TCTGATATTG | ATGAAATTGT | TCTTGTTGGT | GGCTCGACTC | GAATTCCAAA | GATTCAGCAA  3000 |
| CTGGTTAAAG | AGTTCTTCAA | TGGCAAGGAA | CCATCCCGTG | GCATAAACCC | AGATGAAGCT  3060 |
| GTAGCGTATG | GTGCTGCTGT | CCAGGCTGGT | GTGCTCTCTG | GTGATCAAGA | TACAGGTAGG  3120 |
| TCATCATCGC | AGCATCTTTC | TTAGTGATTC | AGTAGCTTGA | TGGAAGAGCT | CGGTACCCCT  3180 |
| ATTGCTTTAG | AAAATACCAG | AATATGAGCA | ACAAGGTCAC | ACAGCTAGTA | AAGGGTATAA  3240 |
| GTGAAGACAA | GACTGGGGTA | GTCTCCAAGA | TCATTAGCAA | CTGTTTAATT | CACTGCCTTT  3300 |
| AAAATGTGTG | TGTTAGAACC | TAACCAAATG | TTAGAGAGAT | AAACTTTACA | TAGCTCATAG  3360 |
| GGAGAACTTG | AATTAAAAGT | TAAATAACTT | ATCCTTACAG | GTGACCTGGT | ACTGCTTCAT  3420 |
| GTATGTCCCC | TTACACTTGG | TATTGAAACT | GTAGGAGGTG | TCATGACCAA | ACTGATTCCA  3480 |
| AGTAATACAG | TGGTGCCTAC | CAAGAACTCT | CAGATCTTTT | CTACAGCTTC | TGATAATCAA  3540 |
| CCAACTGTTA | CAATCAAGGT | CTATGAAGGT | AATTACCTTA | AGTTTGGTTA | ATATCATGGC  3600 |
| TTTTTTTTG | AGATGAAGTC | TTGCTCTGTT | GCCCAGGCTG | GACTGCAGTG | GCACGATCTC  3660 |
| GGCTCACTGC | AAATTCTGTC | TCCCGGGTTC | AAGTGATTCT | CCTGCCTCAG | CCTCCAGAGT  3720 |
| AGCTGGATTA | CAGCCTGACC | ACCACACCTG | GCTAATTTCT | GTATTTTAG | TAGAGGATGG  3780 |
| GCTTTCACCA | TGTTTCCCAG | GCTGGTCTCC | AACTCCTGAC | CTCAGGTCAT | CTGCCTGCCT  3840 |
| CCACCGTCCC | GAAAGTACTG | GGATTATAGC | GTGAGCCACC | ACGCCAGATC | TATCTATCAT  3900 |
| GGCATATTTT | AAAAGAACAT | GACTTAATAT | GTCCTATTGA | AATGGCTAGG | GAACTAAGTA  3960 |
| ACTGCTGTTT | TCAGATGGAG | GTCTTAATTT | GAATAATGTT | GATATTAGAT | ATTTAGCATT  4020 |
| CTTTTTTTTT | TTTTTTAAT | GGAGTCTTGC | TCTGTCGCCT | AGGCTGGGGT | GCAGTGGCAT  4080 |
| GACTTGCAAC | CTCTGCCTCC | CGAATAGCTG | GGATTACAGG | TGCCCACCAT | CACGCCCGGC  4140 |
| TAAGTTTTGT | ATTTTTAGTA | GAGGCGAGTT | TCGCCATGTT | GGCCAGGCTG | GTCTTGAACC  4200 |
| CCTAACCTCA | GTGATCCCAC | GGTCACCGAC | CTGGCCTCCC | AAAAGTACTG | TACCCAGCCA  4260 |
| ATGATTAGCA | TTCTCACTAA | TAATAGCATC | TGAGCTGGCT | CCTAGAGTAC | AAGAAAAAGG  4320 |
| AGTTCACAGT | ACTTTAAAAT | AGATAAAATT | CAGTTGAGTT | AGTAACCTAA | CTCATTGTTA  4380 |
| GTACTAGTTG | CTGCTCCTTG | TAGACCAATA | TGAAATTACT | TTTAGCTCGA | TAAAACCAAA  4440 |
| AGTGTCACTT | TATGCTTCAG | ACTGAAATGC | GGGGATCTAG | ATGTGCTAAT | GCTTGTCAGT  4500 |
| AACAACTAAC | AAGTTTTTCT | GTATGTAACT | TCTAGGTGAA | AGACCCCTGA | CAAAAGACAA  4560 |
| TCATCTTCTG | GGTACATTTG | ATCTGACTGG | AATTCCTCCT | GCTCCTCGTG | GGGTCCCACA  4620 |
| GATTGAAGTC | ACCTTTGAGA | TAGATGTGAA | TGGTATTCTT | CGAGTGACAG | CTGAAGACAA  4680 |
| GGGTACAGGG | AACAAAAATA | AGATCACAAT | CACCAATGAC | CAGAATCGCC | TGACACCTGA  4740 |
| AGAAATCGAA | AGGATGGTTA | ATGATGCTGA | GAAGTTTGCT | GAGGAAGACA | AAAAGCTGAA  4800 |
| GGAGCGCATT | GATACTAGAA | ATGAGTTGGA | AAGCTATGCC | TATTCTCTAA | AGAATCAGAT  4860 |
| TGGAGATAAA | GAAAAGCTGG | GAGGTAAACT | TTCCTCTGAA | GATAAGGAGA | CCATGGAAAA  4920 |
| AGCTGTAGAA | GAAAAGATTG | AATGGCTGGA | AAGCCACCAA | GATGCTGACA | TTGAAGACTT  4980 |
| CAAAGCTAAG | AAGAAGGAAC | TGGAAGAAAT | TGTTCAACCA | ATTATCAGCA | AACTCTATGG  5040 |
| AAGTGCAGGC | CCTCCCCCAA | CTGGTGAAGA | GGATACAGCA | GAAAAAGATG | AGTTGTAGAC  5100 |
| ACTGATCTGC | TAGTGCTGTA | ATATTGTAAA | TACTGGACTC | AGGAACTTTT | GTTAGGAAAA  5160 |
| AATTGAAAGA | ACTTAAGTCT | CGAATGTAAT | TGGAATCTTC | ACCTCAGAGT | GGAGTTGAAA  5220 |
| CTGCTATAGC | CTAAGCGGCT | GTTTACTGCT | TTTCATTAGC | AGTTGCTCAC | ATGTCTTTGG  5280 |
| GTGGGGGGGA | GAAGAAGAAT | TGGCCATCTT | AAAAAGCGGG | TAAAAAACCT | GGGTTAGGGT  5340 |

| | | | | |
|---|---|---|---|---|
| GTGTGTTCAC | CTTCAAAATG | TTCTATTTAA | CAACTGGGTC | ATGTGCATCT | GGTGTAGGAG | 5400 |
| GTTTTTTCTA | CCATAAGTGA | CACCAATAAA | TGTTTGTTAT | TTACACTGGT | CTAATGTTTG | 5460 |
| TGAGAAGCTT | | | | | | 5470 |

(2) INFORMATION FOR SEQ ID NO:13:

(i) SEQUENCE CHARACTERISTICS:
        (A) LENGTH: 2089 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 66..2005

(xi) SEQUENCE DESCRIPTION: SEQ ID NO:13:

```
GAGGCAGCTG CCGGGCATTA GTGTGGTCTC GTCGTCAGCG CAGCTGGGCC TACACACAAG          60

CAACC ATG TCT AAG GGA CCT GCA GTT GGC ATT GAT CTC GGC ACC ACC            107
      Met Ser Lys Gly Pro Ala Val Gly Ile Asp Leu Gly Thr Thr
       1           5                  10

TAC TCC TGT GTG GGT GTC TTC CAG CAT GGA AAG GTG GAA ATT ATT GCC          155
Tyr Ser Cys Val Gly Val Phe Gln His Gly Lys Val Glu Ile Ile Ala
 15              20                  25                  30

AAT GAC CAG GGT AAC CGC ACC ACG CCA AGC TAT GTT GCT TTC ACG GAC          203
Asn Asp Gln Gly Asn Arg Thr Thr Pro Ser Tyr Val Ala Phe Thr Asp
                 35                  40                  45

ACA GAG AGA TTA ATT GGG GAT GCG GCC AAG AAT CAG GTT GCA ATG AAC          251
Thr Glu Arg Leu Ile Gly Asp Ala Ala Lys Asn Gln Val Ala Met Asn
             50                  55                  60

CCC ACC AAC ACA GTT TTT GAT GCC AAA CGT CTG ATC GGG CGT AGG TTT          299
Pro Thr Asn Thr Val Phe Asp Ala Lys Arg Leu Ile Gly Arg Arg Phe
             65                  70                  75

GAT GAT GCT GTT GTT CAG TCT GAT ATG AAG CAC TGG CCC TTC ATG GTG          347
Asp Asp Ala Val Val Gln Ser Asp Met Lys His Trp Pro Phe Met Val
         80                  85                  90

GTG AAT GAT GCA GGC AGG CCC AAG GTC CAA GTC GAA TAC AAA GGG GAG          395
Val Asn Asp Ala Gly Arg Pro Lys Val Gln Val Glu Tyr Lys Gly Glu
 95                 100                 105                 110

ACA AAA AGT TTC TAC CCA GAG GAA GTG TCC TCC ATG GTT CTG ACA AAG          443
Thr Lys Ser Phe Tyr Pro Glu Glu Val Ser Ser Met Val Leu Thr Lys
                115                 120                 125

ATG AAG GAA ATT GCA GAA GCA TAC CTC GGA AAG ACT GTT ACC AAC GCT          491
Met Lys Glu Ile Ala Glu Ala Tyr Leu Gly Lys Thr Val Thr Asn Ala
            130                 135                 140

GTG GTC ACA GTG CCC GCT TAC TTC AAT GAC TCT CAG CGA CAG GCA ACA          539
Val Val Thr Val Pro Ala Tyr Phe Asn Asp Ser Gln Arg Gln Ala Thr
        145                 150                 155

AAA GAT GCT GGA ACT ATT GCT GGC CTC AAT GTA CTT CGA ATC ATC AAT          587
Lys Asp Ala Gly Thr Ile Ala Gly Leu Asn Val Leu Arg Ile Ile Asn
    160                 165                 170

GAA CCA ACT GCT GCT GCT ATT GCT TAT GGC TTA GAT AAG AAG GTC GGA          635
Glu Pro Thr Ala Ala Ala Ile Ala Tyr Gly Leu Asp Lys Lys Val Gly
175                 180                 185                 190

GCT GAA AGG AAT GTG CTC ATT TTT GAC TTG GGA GGT GGC ACT TTT GAT          683
Ala Glu Arg Asn Val Leu Ile Phe Asp Leu Gly Gly Gly Thr Phe Asp
                195                 200                 205

GTG TCA ATC CTC ACT ATT GAG GAT GGA ATT TTT GAG GTC AAA TCA ACA          731
Val Ser Ile Leu Thr Ile Glu Asp Gly Ile Phe Glu Val Lys Ser Thr
                210                 215                 220
```

| | | | | | | | | | | | | | | | | |
|---|---|---|---|---|---|---|---|---|---|---|---|---|---|---|---|---|
| GCT | GGA | GAC | ACC | CAC | TTA | GGC | GGA | GAA | GAC | TTT | GAT | AAC | CGA | ATG | GTC | 779 |
| Ala | Gly | Asp | Thr | His | Leu | Gly | Gly | Glu | Asp | Phe | Asp | Asn | Arg | Met | Val | |
| | | 225 | | | | 230 | | | | | 235 | | | | | |
| AAT | CAT | TTC | ATT | GCT | GAG | TTC | AAG | CGA | AAG | CAC | AAG | AAA | GAC | ATC | AGT | 827 |
| Asn | His | Phe | Ile | Ala | Glu | Phe | Lys | Arg | Lys | His | Lys | Lys | Asp | Ile | Ser | |
| 240 | | | | | 245 | | | | | 250 | | | | | | |
| GAG | AAC | AAG | AGA | GCT | GTC | CGC | CGT | CTC | CGC | ACG | GCC | TGC | GAG | CGG | GCC | 875 |
| Glu | Asn | Lys | Arg | Ala | Val | Arg | Arg | Leu | Arg | Thr | Ala | Cys | Glu | Arg | Ala | |
| 255 | | | | | 260 | | | | | 265 | | | | | 270 | |
| AAG | CGC | ACC | CTC | TCC | TCC | AGC | ACC | CAG | GCC | AGT | ATT | GAG | ATT | GAT | TCT | 923 |
| Lys | Arg | Thr | Leu | Ser | Ser | Ser | Thr | Gln | Ala | Ser | Ile | Glu | Ile | Asp | Ser | |
| | | | | 275 | | | | 280 | | | | | 285 | | | |
| CTC | TAT | GAG | GGA | ATT | GAC | TTC | TAT | ACC | TCC | ATT | ACC | CGT | GCT | CGA | TTT | 971 |
| Leu | Tyr | Glu | Gly | Ile | Asp | Phe | Tyr | Thr | Ser | Ile | Thr | Arg | Ala | Arg | Phe | |
| | | | 290 | | | | | 295 | | | | | 300 | | | |
| GAG | GAG | TTG | AAT | GCT | GAC | CTG | TTC | CGT | GGC | ACA | CTG | GAC | CCT | GTA | GAG | 1019 |
| Glu | Glu | Leu | Asn | Ala | Asp | Leu | Phe | Arg | Gly | Thr | Leu | Asp | Pro | Val | Glu | |
| | | | 305 | | | | 310 | | | | | 315 | | | | |
| AAG | GCC | CTT | CGA | GAT | GCC | AAG | CTG | GAC | AAG | TCA | CAG | ATC | CAT | GAT | ATT | 1067 |
| Lys | Ala | Leu | Arg | Asp | Ala | Lys | Leu | Asp | Lys | Ser | Gln | Ile | His | Asp | Ile | |
| 320 | | | | | 325 | | | | | 330 | | | | | | |
| GTC | TTG | GTG | GGT | GGT | TCT | ACC | AGA | ATC | CCC | AAG | ATC | CAG | AAA | CTT | CTG | 1115 |
| Val | Leu | Val | Gly | Gly | Ser | Thr | Arg | Ile | Pro | Lys | Ile | Gln | Lys | Leu | Leu | |
| 335 | | | | | 340 | | | | | 345 | | | | | 350 | |
| CAA | GAC | TTC | TTC | AAT | GGA | AAA | GAG | CTG | AAC | AAG | AGC | ATT | AAC | CCC | GAT | 1163 |
| Gln | Asp | Phe | Phe | Asn | Gly | Lys | Glu | Leu | Asn | Lys | Ser | Ile | Asn | Pro | Asp | |
| | | | | 355 | | | | 360 | | | | | 365 | | | |
| GAA | GCT | GTT | GCC | TAT | GGT | GCA | GCT | GTC | CAG | GCA | GCC | ATT | CTA | TCT | GGA | 1211 |
| Glu | Ala | Val | Ala | Tyr | Gly | Ala | Ala | Val | Gln | Ala | Ala | Ile | Leu | Ser | Gly | |
| | | | 370 | | | | | 375 | | | | | 380 | | | |
| GAC | AAG | TCT | GAG | AAC | GTT | CAG | GAT | TTG | CTG | CTC | TTG | GAT | GTC | ACT | CCT | 1259 |
| Asp | Lys | Ser | Glu | Asn | Val | Gln | Asp | Leu | Leu | Leu | Leu | Asp | Val | Thr | Pro | |
| | | 385 | | | | 390 | | | | | 395 | | | | | |
| CTT | TCC | CTT | GGT | ATT | GAA | ACT | GCT | GGC | GGA | GTC | ATG | ACT | GTC | CTC | ATC | 1307 |
| Leu | Ser | Leu | Gly | Ile | Glu | Thr | Ala | Gly | Gly | Val | Met | Thr | Val | Leu | Ile | |
| | 400 | | | | | 405 | | | | | 410 | | | | | |
| AAG | CGC | AAT | ACC | ACC | ATC | CCC | ACC | AAG | CAG | ACA | CAG | ACT | CTC | ACC | ACC | 1355 |
| Lys | Arg | Asn | Thr | Thr | Ile | Pro | Thr | Lys | Gln | Thr | Gln | Thr | Leu | Thr | Thr | |
| 415 | | | | | 420 | | | | | 425 | | | | | 430 | |
| TAC | TCT | GAC | AAC | CAG | CCT | GGT | GTA | CTC | ATT | CAG | GTG | TAT | GAA | GGT | GAA | 1403 |
| Tyr | Ser | Asp | Asn | Gln | Pro | Gly | Val | Leu | Ile | Gln | Val | Tyr | Glu | Gly | Glu | |
| | | | | 435 | | | | 440 | | | | | 445 | | | |
| AGG | GCC | ATG | ACC | AAG | GAC | AAC | AAC | CTG | CTT | GGA | AAG | TTC | GAG | CTC | ACA | 1451 |
| Arg | Ala | Met | Thr | Lys | Asp | Asn | Asn | Leu | Leu | Gly | Lys | Phe | Glu | Leu | Thr | |
| | | | 450 | | | | | 455 | | | | | 460 | | | |
| GGC | ATC | CCT | CCA | GCA | CCC | CGT | GGG | GTT | CCT | CAG | ATT | GAG | GTT | ACT | TTT | 1499 |
| Gly | Ile | Pro | Pro | Ala | Pro | Arg | Gly | Val | Pro | Gln | Ile | Glu | Val | Thr | Phe | |
| | | 465 | | | | 470 | | | | | 475 | | | | | |
| GAC | ATC | GAT | GCC | AAT | GGC | ATC | CTC | AAT | GTT | TCT | GCT | GTA | GAT | AAG | AGC | 1547 |
| Asp | Ile | Asp | Ala | Asn | Gly | Ile | Leu | Asn | Val | Ser | Ala | Val | Asp | Lys | Ser | |
| | 480 | | | | | 485 | | | | | 490 | | | | | |
| ACA | GGA | AAG | GAG | AAC | AAG | ATC | ACC | ATC | ACC | AAT | GAC | AAG | GGC | CGC | TTG | 1595 |
| Thr | Gly | Lys | Glu | Asn | Lys | Ile | Thr | Ile | Thr | Asn | Asp | Lys | Gly | Arg | Leu | |
| 495 | | | | | 500 | | | | | 505 | | | | | 510 | |
| AGT | AAG | GAA | GAT | ATT | GAG | CGC | ATG | GTC | CAA | GAA | GCT | GAG | AAG | TAC | AAG | 1643 |
| Ser | Lys | Glu | Asp | Ile | Glu | Arg | Met | Val | Gln | Glu | Ala | Glu | Lys | Tyr | Lys | |
| | | | | 515 | | | | 520 | | | | | 525 | | | |
| GCT | GAG | GAT | GAG | AAG | CAG | AGA | GAT | AAG | GTT | TCC | TCC | AAG | AAC | TCA | CTG | 1691 |
| Ala | Glu | Asp | Glu | Lys | Gln | Arg | Asp | Lys | Val | Ser | Ser | Lys | Asn | Ser | Leu | |
| | | | 530 | | | | | 535 | | | | | 540 | | | |

| GAG | TCC | TAT | GCC | TTC | AAC | ATG | AAA | GCA | ACT | GTG | GAA | GAT | GAG | AAA | CTT | 1739 |
| Glu | Ser | Tyr | Ala | Phe | Asn | Met | Lys | Ala | Thr | Val | Glu | Asp | Glu | Lys | Leu | |
| | | 545 | | | | 550 | | | | | 555 | | | | | |

| CAA | GGC | AAG | ATC | AAT | GAT | GAG | GAC | AAA | CAG | AAG | ATT | CTT | GAC | AAG | TGC | 1787 |
| Gln | Gly | Lys | Ile | Asn | Asp | Glu | Asp | Lys | Gln | Lys | Ile | Leu | Asp | Lys | Cys | |
| 560 | | | | | 565 | | | | | 570 | | | | | | |

| AAT | GAA | ATC | ATC | AGC | TGG | CTG | GAT | AAG | AAC | CAG | ACT | GCA | GAG | AAG | GAA | 1835 |
| Asn | Glu | Ile | Ile | Ser | Trp | Leu | Asp | Lys | Asn | Gln | Thr | Ala | Glu | Lys | Glu | |
| 575 | | | | | 580 | | | | | 585 | | | | | 590 | |

| GAA | TTT | GAG | CAT | CAG | CAG | AAA | GAA | CTG | GAG | AAA | GTC | TGC | AAC | CCT | ATT | 1883 |
| Glu | Phe | Glu | His | Gln | Gln | Lys | Glu | Leu | Glu | Lys | Val | Cys | Asn | Pro | Ile | |
| | | | | 595 | | | | | 600 | | | | | 605 | | |

| ATC | ACC | AAG | CTG | TAC | CAG | AGT | GCA | GGT | GGC | ATG | CCT | GGA | GGG | ATG | CCT | 1931 |
| Ile | Thr | Lys | Leu | Tyr | Gln | Ser | Ala | Gly | Gly | Met | Pro | Gly | Gly | Met | Pro | |
| | | | 610 | | | | | 615 | | | | | 620 | | | |

| GGT | GGC | TTC | CCA | GGT | GGA | GGA | GCT | CCC | CCA | TCT | GGT | GGT | GCT | TCT | TCA | 1979 |
| Gly | Gly | Phe | Pro | Gly | Gly | Gly | Ala | Pro | Pro | Ser | Gly | Gly | Ala | Ser | Ser | |
| | | 625 | | | | | 630 | | | | | 635 | | | | |

| GGC | CCC | ACC | ATT | GAA | GAG | GTG | GAT | TA AGTCAGTCCA AGAAGAAGT | | | | | | | | 2025 |
| Gly | Pro | Thr | Ile | Glu | Glu | Val | Asp | | | | | | | | | |
| | 640 | | | | | 645 | | | | | | | | | | |

GTAGCTTTGT TCCACAGGGA CCCAAAAAGT AACATGGAAT AATAAAACTA TTTAAATTGG    2085

CACC    2089

( 2 ) INFORMATION FOR SEQ ID NO:14:

( i ) SEQUENCE CHARACTERISTICS:
        ( A ) LENGTH: 646 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Met | Ser | Lys | Gly | Pro | Ala | Val | Gly | Ile | Asp | Leu | Gly | Thr | Thr | Tyr | Ser |
| 1 | | | | 5 | | | | | 10 | | | | | 15 | |

| Cys | Val | Gly | Val | Phe | Gln | His | Gly | Lys | Val | Glu | Ile | Ile | Ala | Asn | Asp |
| | | | 20 | | | | | 25 | | | | | 30 | | |

| Gln | Gly | Asn | Arg | Thr | Thr | Pro | Ser | Tyr | Val | Ala | Phe | Thr | Asp | Thr | Glu |
| | | | 35 | | | | | 40 | | | | | 45 | | |

| Arg | Leu | Ile | Gly | Asp | Ala | Ala | Lys | Asn | Gln | Val | Ala | Met | Asn | Pro | Thr |
| | | 50 | | | | | 55 | | | | | 60 | | | |

| Asn | Thr | Val | Phe | Asp | Ala | Lys | Arg | Leu | Ile | Gly | Arg | Arg | Phe | Asp | Asp |
| 65 | | | | | 70 | | | | | 75 | | | | | 80 |

| Ala | Val | Val | Gln | Ser | Asp | Met | Lys | His | Trp | Pro | Phe | Met | Val | Val | Asn |
| | | | | 85 | | | | | 90 | | | | | 95 | |

| Asp | Ala | Gly | Arg | Pro | Lys | Val | Gln | Val | Glu | Tyr | Lys | Gly | Glu | Thr | Lys |
| | | | 100 | | | | | 105 | | | | | 110 | | |

| Ser | Phe | Tyr | Pro | Glu | Glu | Val | Ser | Ser | Met | Val | Leu | Thr | Lys | Met | Lys |
| | | | 115 | | | | | 120 | | | | | 125 | | |

| Glu | Ile | Ala | Glu | Ala | Tyr | Leu | Gly | Lys | Thr | Val | Thr | Asn | Ala | Val | Val |
| | | | 130 | | | | | 135 | | | | | 140 | | |

| Thr | Val | Pro | Ala | Tyr | Phe | Asn | Asp | Ser | Gln | Arg | Gln | Ala | Thr | Lys | Asp |
| 145 | | | | | 150 | | | | | 155 | | | | | 160 |

| Ala | Gly | Thr | Ile | Ala | Gly | Leu | Asn | Val | Leu | Arg | Ile | Ile | Asn | Glu | Pro |
| | | | | 165 | | | | | 170 | | | | | 175 | |

| Thr | Ala | Ala | Ala | Ile | Ala | Tyr | Gly | Leu | Asp | Lys | Lys | Val | Gly | Ala | Glu |
| | | | 180 | | | | | 185 | | | | | 190 | | |

```
Arg  Asn  Val  Leu  Ile  Phe  Asp  Leu  Gly  Gly  Gly  Thr  Phe  Asp  Val  Ser
          195            200                 205
Ile  Leu  Thr  Ile  Glu  Asp  Gly  Ile  Phe  Glu  Val  Lys  Ser  Thr  Ala  Gly
          210            215                 220
Asp  Thr  His  Leu  Gly  Gly  Glu  Asp  Phe  Asp  Asn  Arg  Met  Val  Asn  His
225                      230                 235                           240
Phe  Ile  Ala  Glu  Phe  Lys  Arg  Lys  His  Lys  Asp  Ile  Ser  Glu  Asn
               245                      250                      255
Lys  Arg  Ala  Val  Arg  Arg  Leu  Arg  Thr  Ala  Cys  Glu  Arg  Ala  Lys  Arg
               260                 265                      270
Thr  Leu  Ser  Ser  Ser  Thr  Gln  Ala  Ser  Ile  Glu  Ile  Asp  Ser  Leu  Tyr
          275                 280                 285
Glu  Gly  Ile  Asp  Phe  Tyr  Thr  Ser  Ile  Thr  Arg  Ala  Arg  Phe  Glu  Glu
     290                 295                      300
Leu  Asn  Ala  Asp  Leu  Phe  Arg  Gly  Thr  Leu  Asp  Pro  Val  Glu  Lys  Ala
305                 310                 315                           320
Leu  Arg  Asp  Ala  Lys  Leu  Asp  Lys  Ser  Gln  Ile  His  Asp  Ile  Val  Leu
               325                 330                      335
Val  Gly  Gly  Ser  Thr  Arg  Ile  Pro  Lys  Ile  Gln  Lys  Leu  Leu  Gln  Asp
               340                 345                      350
Phe  Phe  Asn  Gly  Lys  Glu  Leu  Asn  Lys  Ser  Ile  Asn  Pro  Asp  Glu  Ala
          355                 360                 365
Val  Ala  Tyr  Gly  Ala  Ala  Val  Gln  Ala  Ala  Ile  Leu  Ser  Gly  Asp  Lys
     370                 375                 380
Ser  Glu  Asn  Val  Gln  Asp  Leu  Leu  Leu  Leu  Asp  Val  Thr  Pro  Leu  Ser
385                      390                 395                           400
Leu  Gly  Ile  Glu  Thr  Ala  Gly  Gly  Val  Met  Thr  Val  Leu  Ile  Lys  Arg
               405                 410                      415
Asn  Thr  Thr  Ile  Pro  Thr  Lys  Gln  Thr  Gln  Thr  Leu  Thr  Thr  Tyr  Ser
               420                 425                      430
Asp  Asn  Gln  Pro  Gly  Val  Leu  Ile  Gln  Val  Tyr  Glu  Gly  Glu  Arg  Ala
          435                 440                 445
Met  Thr  Lys  Asp  Asn  Asn  Leu  Leu  Gly  Lys  Phe  Glu  Leu  Thr  Gly  Ile
     450                 455                 460
Pro  Pro  Ala  Pro  Arg  Gly  Val  Pro  Gln  Ile  Glu  Val  Thr  Phe  Asp  Ile
465                 470                 475                           480
Asp  Ala  Asn  Gly  Ile  Leu  Asn  Val  Ser  Ala  Val  Asp  Lys  Ser  Thr  Gly
               485                 490                      495
Lys  Glu  Asn  Lys  Ile  Thr  Ile  Thr  Asn  Asp  Lys  Gly  Arg  Leu  Ser  Lys
               500                 505                      510
Glu  Asp  Ile  Glu  Arg  Met  Val  Gln  Glu  Ala  Glu  Lys  Tyr  Lys  Ala  Glu
               515                 520                      525
Asp  Glu  Lys  Gln  Arg  Asp  Lys  Val  Ser  Ser  Lys  Asn  Ser  Leu  Glu  Ser
530                      535                 540
Tyr  Ala  Phe  Asn  Met  Lys  Ala  Thr  Val  Glu  Asp  Glu  Lys  Leu  Gln  Gly
545                 550                 555                           560
Lys  Ile  Asn  Asp  Glu  Asp  Lys  Gln  Lys  Ile  Leu  Asp  Lys  Cys  Asn  Glu
               565                 570                      575
Ile  Ile  Ser  Trp  Leu  Asp  Lys  Asn  Gln  Thr  Ala  Glu  Lys  Glu  Glu  Phe
               580                 585                      590
Glu  His  Gln  Gln  Lys  Glu  Leu  Glu  Lys  Val  Cys  Asn  Pro  Ile  Ile  Thr
          595                 600                 605
Lys  Leu  Tyr  Gln  Ser  Ala  Gly  Gly  Met  Pro  Gly  Gly  Met  Pro  Gly  Gly
```

|     |     |     | 610 |     |     |     | 615 |     |     |     | 620 |     |     |
| --- | --- | --- | --- | --- | --- | --- | --- | --- | --- | --- | --- | --- | --- |
| Phe | Pro | Gly | Gly | Gly | Ala | Pro | Pro | Ser | Gly | Gly | Ala | Ser | Ser | Gly | Pro |
| 625 |     |     |     | 630 |     |     |     | 635 |     |     |     | 640 |

Thr Ile Glu Glu Val Asp
           645

( 2 ) INFORMATION FOR SEQ ID NO:15:

( i ) SEQUENCE CHARACTERISTICS:
        ( A ) LENGTH: 5408 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: exon
        ( B ) LOCATION: 1040..1244

( i x ) FEATURE:
        ( A ) NAME/KEY: exon
        ( B ) LOCATION: 1569..1772

( i x ) FEATURE:
        ( A ) NAME/KEY: exon
        ( B ) LOCATION: 2097..2249

( i x ) FEATURE:
        ( A ) NAME/KEY: exon
        ( B ) LOCATION: 2337..2892

( i x ) FEATURE:
        ( A ) NAME/KEY: exon
        ( B ) LOCATION: 3104..3306

( i x ) FEATURE:
        ( A ) NAME/KEY: exon
        ( B ) LOCATION: 3535..3733

( i x ) FEATURE:
        ( A ) NAME/KEY: exon
        ( B ) LOCATION: 3881..4113

( i x ) FEATURE:
        ( A ) NAME/KEY: exon
        ( B ) LOCATION: 4445..4629

( x i ) SEQUENCE DESCRIPTION: SEQ ID NO:15:

```
GAGCTTGAAA  GTTCCAGAAC  GCTGCGGTGA  GTGCGTTATC  GTGAGGCGGC  GCGGTGGGGT     60
GGGTGCGGAA  GGGGGCGAGG  CGAGGAGTGG  AGCCGCGTTG  TGATTGTGAT  TGGGTCTTGT    120
AAGGGCAGCC  GGACTCTATT  GGCCGGGAAC  CTAATGCAGG  AAGCAGGCGG  ACCCCTTCTG    180
GAAGGTTCTA  AGATAGGGTA  TAAGAGGCAG  GGTGGCGGGC  GGAAACCGGT  GCTCAGTTGA    240
ACTGCGCTGC  AGCTCTTGGT  TTTTTGTGGC  TTCCTTCGTT  ATTGGAGCCA  GGCCTACACC    300
CCAGGTAAAA  CCTCTGCTCA  AGAGTTGGGT  TGTGGGTCTG  GGAGCGTGCA  GCCTCCACAC    360
AGGCCTGTTG  GGCTTGCTGA  GGCTTGGGGG  TTCTGAGAAT  CTCGTCGAGG  CGAGTGTGCG    420
GCTCCTTCTA  CCGGCTTAAA  GGGCCTCAGT  TTTCGGTGGG  ATGGCAGCGG  TATTTGGTTG    480
CAGCCGGCAG  ACGGAAATGT  AGGGAGTGGG  CCGCATGGCC  CCAGGGGAGG  CTGGGAGACG    540
CCCGGCCGCG  TGGCGGGGA   GGGTTGCTGC  ATCGGTTTGC  CTGGCGCGCG  GGAAGTGGA    600
GCCAGCGTTT  TCTTTCACCC  AGTTCCCTGC  TTAGTCCAGT  CCCACCGTGG  TTCTTCAGAG    660
CTGTTCTTGG  CGTGCTTCCA  GTATGGGGGT  ACATTCCGGA  GTAGTTAAAA  GCCCGTTGAC    720
TCCCGGGGGG  CACTGGCACC  TGGCGAGGGA  GGGGAACAGA  CAGTGCTCAG  TTCGGGGTAA    780
GACCACGTGT  TGAGCAACGC  CCCACGCCGT  CTGGGTCGAT  GGGTCCTTCA  TCTAGGGCGT    840
```

```
GCTGTGCTGC  GGTTGGCACG  GCAACCTGGA  CTGCAGCACT  AGTTCTGGAC  CTCGCGCGTG   900
CTTAGACAGG  AGGTGATGGG  CACTATTACC  TCTTGGCAGT  GGCCATACGT  TTTTCCTGGT   960
TAAGTGTTCT  GTTAAGGGAT  GAGGGAAATA  TTTTGATTAA  TTGAATTTTT  AAACCAGATT  1020
TTTCTTTTTT  TCAGCAACCA  TGTCCAAGGG  ACCTGCAGTT  GGTATTGATC  TTGGCACCAC  1080
CTACTCTTGT  GTGGGTGTTT  TCCAGCACGG  AAAAGTCGAG  ATAATTGCCA  ATGATCAGGG  1140
AAACCGAACC  ACTCCAAGCT  ATGTCGCCTT  TACGGACACT  GAACGGTTGA  TCGGTGATGC  1200
CGCAAAGAAT  CAAGTTGCAA  TGAACCCCAC  CAACACAGTT  TTTGGTGAGT  TCCTAATTTT  1260
AAATGACAGA  ACAAATATAA  ACAGGGCTAG  GAAGCACAAA  AGTTTATGAA  ACGTGAGGAG  1320
GGAACTTTTT  GATTTAGAA   AAACTGAGCT  GAGAGACTTG  TTATCAAGTC  TGTTATAAAA  1380
CAGGTTGTAG  AAACCTTTCA  GGCTGAAATC  TGGATAACGT  AGGAGGTTGA  AGTTTGAACC  1440
TTTGCTAGGT  ATATGGTAGT  TGAATTCACC  TACCTATGAA  CTGTTAGGTA  TTTGAGTAAT  1500
CATGGACTTG  AGTTTATCT   GAAGAGCTAT  GAAATTGAAA  GTGTTTTCAT  TTGACACCTT  1560
TTACAGATGC  CAAACGTCTG  ATTGGACGCA  GATTTGATGA  TGCTGTTGTC  CAGTCTGATA  1620
TGAAACATTG  GCCCTTTATG  GTGGTGAATG  ATGCTGGCAG  GCCCAAGGTC  CAAGTAGAAT  1680
ACAAGGGAGA  GACCAAAAGC  TTCTATCCAG  AGGAGGTGTC  TTCTATGGTT  CTGACAAAGA  1740
TGAAGGAAAT  TGCAGAAGCC  TACCTTGGGA  AGGTGAGGTT  GGTTTTCAG   TATGGGGTGC  1800
ATTCCGGAGT  AGTTAAAAGC  CCGATGACTC  CCGGGGGCAC  TGGCACCTGG  CGAGGGAGGG  1860
GAACAGATGG  GGCTCAGCTC  AGGGTTAAGA  CCACGTGCCC  AACAGTGCCC  TAGGCTCTCT  1920
AGGTAGATGG  GTCTGTCAAC  ACCAGAAACC  AGTGAATCTT  GACAATTACA  CAGTAATTTA  1980
CATTTTGGTG  GGGGGGGTGC  TCCAGCTGTT  GTTTCACCAG  CATTAATCCA  TTTGCTGGAG  2040
TTTGCATATA  TGTAAGTATA  ATAGTTACCA  ATCTGTGGTC  TTTTCCTTAT  TCCTAGACTG  2100
TTACCAATGC  TGTGGTCACA  GTGCCAGCTT  ACTTTAATGA  CTCTCAGCGT  CAGGCTACCA  2160
AAGATGCTGG  AACTATTGCT  GGTCTCAATG  TACTTAGAAT  TATTAATGAG  CCAACTGCTG  2220
CTGCTATTGC  TTACGGCTTA  GACAAAAAGG  TATGTACCAT  TTGTGATGCA  AGTTCGGATT  2280
ATTTTAAGAT  TAATTTGATC  CATCGTAAAT  TTAAATGAGA  TTGTTTTTAA  CGGCAGGTTG  2340
GAGCAGAAAG  AAACGTGCTC  ATCTTTGACC  TGGGAGGTGG  CACTTTTGAT  GTGTCAATCC  2400
TCACTATTGA  GGATGGAATC  TTTGAGGTCA  AGTCTACAGC  TGGAGACACC  CACTTGGGTG  2460
GAGAAGATTT  TGACAACCGA  ATGGTCAACC  ATTTTATTGC  TGAGTTTAAG  CGCAAGCATA  2520
AGAAGGACAT  CAGTGAGAAC  AAGAGAGCTG  TAAGACGCCT  CCGTACTGCT  TGTGAACGTG  2580
CTAAGCGTAC  CCTCTCTTCC  AGCACCCAGG  CCAGTATTGA  GATCGATTCT  CTCTATGAAG  2640
GAATCGACTT  CTATACCTCC  ATTACCCGTG  CCCGATTTGA  AGAACTGAAT  GCTGACCTGT  2700
TCCGTGGCAC  CCTGGACCCA  GTAGAGAAAG  CCCTTCGAGA  TGCCAAACTA  GACAAGTCAC  2760
AGATTCATGA  TATTGTCCTG  GTTGGTGGTT  CTACTCGTAT  CCCCAAGATT  CAGAAGCTTC  2820
TCCAAGACTT  CTTCAATGGA  AAAGAACTGA  ATAAGAGCAT  CAACCCTGAT  GAAGCTGTTG  2880
CTTATGGTGC  AGGTAACAAT  GGTATCTCAA  TTAACCCTAA  AGGCAGGCAG  GCCCAAGGTG  2940
ACTCGCTGTG  ATGAGTGATT  GTTAAACATT  CGTAGTTTCC  ACCAAAAGCT  GGCTAATGA   3000
TGGCAACACC  TTCCTTGGAT  GTCTGAGCGA  GTGATAGTTA  AAACAGGAGC  TATGTACTGG  3060
GTTTTCTTTT  AACTTCTTTT  AACGTTAACT  TTTTGTTTGC  TAGCTGTCCA  GGCAGCCATC  3120
TTGTCTGGAG  ACAAGTCTGA  GAATGTTCAA  GATTGCTGC   TCTTGGATGT  CACTCCTCTT  3180
TCCCTTGGTA  TTGAAACTGC  TGGTGGAGTC  ATGACTGTCC  TCATCAAGCG  TAATACCACC  3240
```

```
ATTCCTACCA  AGCAGACACA  GACCTTCACT  ACCTATTCTG  ACAACCAGCC  TGGTGTGCTT   3300

ATTCAGGTAT  GTTTCTGTAC  TTCTCTTGTT  TGGCTTACTG  ATAACAGATA  AAGGGAAGTC   3360

TTGACTGACT  CGCTATGATG  ATGGATTCCA  AAACCATTCG  TAGTTTCCAC  CAGAAAGTCT   3420

TATGTTGGCC  AGTTCCTTCC  TTGGATGTTT  GAGCGACCAT  TCTTCCTTAG  CAGGACCCTA   3480

GCACTGTCAC  AGACCTGGAG  TCCATTGTAG  TAATTTGTTT  TATTTCCTAC  CAAGGTTTAT   3540

GAAGGCGAGC  GTGCCATGAC  AAAGGATAAC  AACCTGCTTG  GCAAGTTTGA  ACTCACAGGC   3600

ATACCTCCTG  CACCCCGAGG  TGTTCCTCAG  ATTGAAGTCA  CTTTTGACAT  TGATGCCAAT   3660

GGTATACTCA  ATGTCTCTGC  TGTGGACAAG  AGTACGGGAA  AAGAGAACAA  GATTACTATC   3720

ACTAATGACA  AGGGTAAGGA  GGCACTGTCA  TCTGGTCTTG  ACAGGGATAA  TGGTATTTCA   3780

ATTGAGTTAC  TGGTGAATAA  GGGCGTCTAG  CTAAGAGAAA  CTAGAGTTAC  ACATACACAG   3840

GTAATTTAAG  GCTTTTACTT  AGAGTTAATT  TCTTTCCTAG  GCCGTTTGAG  CAAGGAAGAC   3900

ATTGAACGTA  TGGTCCAGGA  AGCTGAGAAG  TACAAAGCTG  AAGATGAGAA  GCAGAGGGAC   3960

AAGGTGTCAT  CCAAGAATTC  ACTTGAGTCC  TATGCCTTCA  ACATGAAAGC  AACTGTTGAA   4020

GATGAGAAAC  TTCAAGGCAA  GATTAACGAT  GAGGACAAAC  AGAAGATTCT  GGACAAGTGT   4080

AATGAAATTA  TCAACTGGCT  TGATAAGAAT  CAGGTTTGTG  TTTTTTTTT   TTTTTTCCT    4140

CCCCCACGCA  ATGGAGGGGA  AGGGGATGGT  AAACCAAGCT  TGAGCTGGAT  TTCAGTGTAG   4200

GGTCACAATG  ATGAATGGTC  CAAAACATTC  GCGGTTTCCA  CCAGAATTCA  AGGTGTTGGC   4260

AACTACCTTC  CTTGGATGTC  TGAGTGACCC  AAGATGTTAA  GGAAGAATAA  GGCCCTATTT   4320

TAATGTTGGT  ATGGGCCCTC  TTGTAAGAGT  TTGCTCCAGA  CTTTTAGTAT  CAGATTGCGT   4380

CAGGGAGAAA  GAAGGGTTAT  TAACATTAAA  AGAACTTGCA  GTAATTCCTT  TTTCTCTTCC   4440

TCAGACTGCT  GAGAAGGAAG  AATTTGAACA  TCAACAGAAA  GAGCTGGAGA  AAGTTTGCAA   4500

CCCCATCATC  ACCAAGCTGT  ACCAGAGTGC  AGGAGGCATG  CCAGGAGGAA  TGCCTGGGGG   4560

ATTTCCTGGT  GGTGGAGCTC  CTCCCTCTGG  TGGTGCTTCC  TCAGGGCCCA  CCATTGAAGA   4620

GGTTGATTAA  GCCAACCAAG  TGTAGATGTA  GCATTGTTCC  ACACATTTAA  AACATTTGAA   4680

GGACCTAAAT  TCGTAGCAAA  TTCTGTGGCA  GTTTTAAAAA  GTTAAGCTGC  TATAGTAAGT   4740

TACTGGGCAT  TCTCAATACT  TGAATATGGA  ACATATGCAC  AGGGGAAGGA  AATAACATTG   4800

CACTTTATAC  ACTGTATTGT  AAGTGGAAAA  TGCAATGTCT  TAAATAAAAC  TATTTAAAAT   4860

TGGCACCATA  CAATTGCTTT  GAGTCTTTAA  ATAATCTCCC  AGGCCAGCGG  TGGGAGAAGT   4920

AGGCTTAGGT  GATTATGTGA  CTCTTACTTT  CTCCTTCCTC  TTAAGCTTGA  GTTAACAAGG   4980

GCTGGGTGGC  AAGTTGCCCT  TCAGAGCATG  TGGATGGTAC  ATTTTGGAAT  TCAGAGCTTT   5040

GAGAAGGGGA  GCATAAGAAA  TTGGATCTGG  ATCAAACTAA  CCTTAGTCCT  TAGGCTGGAG   5100

AGGCAGAAGC  TGACTTAATG  GTGTTTTCTA  AACTTATTCT  GTGTGTAAGC  CTGCCTAGGA   5160

GCAGAGGCTT  TCCTGGAGGG  TTGTGCTAGA  TGAGTAAGAA  TTTAGATACA  GAATCAAATA   5220

ATGGGCAGTG  AATATTAAGC  TACATGGCAG  AGGTATCTGA  ATGTCAATCC  CTTATATGAG   5280

CCACTGCCCT  GTGGGCTTCC  ATTTCTTCTG  AGTTAAGATT  ATTCAGAAGG  TCGGGGATTG   5340

GAGCTAAGCT  GCCACCTGGT  TAATTAAGGT  CCCAACAGTG  AGTTGTGATA  GCCTAGGGGA   5400

GCAGGCTG                                                                5408
```

( 2 ) INFORMATION FOR SEQ ID NO:16:

( i ) SEQUENCE CHARACTERISTICS:

( A ) LENGTH: 666 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:16:

```
Glu Thr Arg Arg Phe Val Cys Asp Glu Arg Arg Ala Gly Gly Met Arg
 1               5                  10                  15
His Leu Leu Leu Ala Leu Leu Leu Gly Gly Ala Arg Ala Asp Asp
            20                  25                  30
Glu Glu Lys Lys Glu Asp Val Gly Thr Val Val Gly Ile Asp Leu Gly
            35                  40                  45
Thr Thr Tyr Ser Cys Val Gly Val Phe Lys Asn Gly Arg Val Glu Ile
        50                  55                  60
Ile Ala Asn Asp Gln Gly Asn Arg Ile Thr Pro Ser Tyr Val Ala Phe
65                  70                  75                  80
Thr Pro Glu Gly Glu Arg Leu Ile Gly Asp Ala Ala Lys Asn Gln Leu
                85                  90                  95
Thr Ser Asn Pro Glu Asn Thr Val Phe Asp Ala Lys Arg Leu Ile Gly
            100                 105                 110
Arg Thr Trp Asn Asp Pro Ser Val Gln Gln Asp Ile Lys Tyr Leu Pro
            115                 120                 125
Phe Lys Val Val Glu Lys Lys Ala Lys Pro His Ile Gln Val Asp Val
        130                 135                 140
Gly Gly Gly Gln Thr Lys Thr Phe Ala Pro Glu Glu Ile Ser Ala Met
145                 150                 155                 160
Val Leu Thr Lys Met Lys Glu Thr Ala Glu Ala Tyr Leu Gly Lys Lys
                165                 170                 175
Val Thr His Ala Val Val Thr Val Pro Ala Tyr Phe Asn Asp Ala Gln
            180                 185                 190
Arg Gln Ala Thr Lys Asp Ala Gly Thr Ile Ala Gly Leu Asn Val Met
            195                 200                 205
Arg Ile Ile Asn Glu Pro Thr Ala Ala Ala Ile Ala Tyr Gly Leu Asp
        210                 215                 220
Lys Arg Glu Gly Glu Lys Asn Ile Leu Val Phe Asp Leu Gly Gly Gly
225                 230                 235                 240
Thr Phe Asp Val Ser Leu Leu Thr Ile Asp Asn Gly Val Phe Glu Val
                245                 250                 255
Val Ala Thr Asn Gly Asp Thr His Leu Gly Gly Glu Asp Phe Asp Gln
            260                 265                 270
Arg Val Met Glu His Phe Ile Lys Leu Tyr Lys Lys Lys Thr Gly Lys
            275                 280                 285
Asp Val Arg Lys Asp Asn Arg Ala Val Gln Lys Leu Arg Arg Glu Val
        290                 295                 300
Glu Lys Ala Lys Arg Ala Leu Ser Ser Gln His Gln Ala Arg Ile Glu
305                 310                 315                 320
Ile Glu Ser Phe Phe Glu Gly Glu Asp Phe Ser Glu Thr Leu Thr Arg
                325                 330                 335
Ala Lys Phe Glu Glu Leu Asn Met Asp Leu Phe Arg Ser Thr Met Lys
            340                 345                 350
Pro Val Gln Lys Val Leu Glu Asp Ser Asp Leu Lys Lys Ser Asp Ile
            355                 360                 365
Asp Glu Ile Val Leu Val Gly Gly Ser Thr Arg Ile Pro Lys Ile Gln
370                 375                 380
```

| | | | | | | | | | | | | | | | |
|---|---|---|---|---|---|---|---|---|---|---|---|---|---|---|---|
| Gln | Leu | Val | Lys | Glu | Phe | Phe | Asn | Gly | Lys | Glu | Pro | Ser | Arg | Gly | Ile |
| 385 | | | | 390 | | | | | 395 | | | | | | 400 |
| Asn | Pro | Asp | Glu | Ala | Val | Ala | Tyr | Gly | Ala | Val | Gln | Ala | Gly | Val | |
| | | | | 405 | | | | 410 | | | | | 415 | | |
| Leu | Ser | Gly | Asp | Gln | Asp | Thr | Gly | Asp | Leu | Val | Leu | Leu | Asp | Val | Cys |
| | | | 420 | | | | | 425 | | | | | 430 | | |
| Pro | Leu | Thr | Leu | Gly | Ile | Glu | Thr | Val | Gly | Gly | Val | Met | Thr | Lys | Leu |
| | | 435 | | | | | 440 | | | | | 445 | | | |
| Ile | Pro | Arg | Asn | Thr | Val | Val | Pro | Thr | Lys | Lys | Ser | Gln | Ile | Phe | Ser |
| 450 | | | | | 455 | | | | | 460 | | | | | |
| Thr | Ala | Ser | Asp | Asn | Gln | Pro | Thr | Val | Thr | Ile | Lys | Val | Tyr | Glu | Gly |
| 465 | | | | | 470 | | | | | 475 | | | | | 480 |
| Glu | Arg | Pro | Leu | Thr | Lys | Asp | Asn | His | Leu | Leu | Gly | Thr | Phe | Asp | Leu |
| | | | | 485 | | | | | 490 | | | | | 495 | |
| Thr | Gly | Ile | Pro | Pro | Ala | Pro | Arg | Gly | Val | Pro | Gln | Ile | Glu | Val | Thr |
| | | | 500 | | | | | 505 | | | | | 510 | | |
| Phe | Glu | Ile | Asp | Val | Asn | Gly | Ile | Leu | Arg | Val | Thr | Ala | Glu | Asp | Lys |
| | | | 515 | | | | 520 | | | | | 525 | | | |
| Gly | Thr | Gly | Asn | Lys | Asn | Lys | Ile | Thr | Ile | Thr | Asn | Asp | Gln | Asn | Arg |
| | | 530 | | | | 535 | | | | | 540 | | | | |
| Leu | Thr | Pro | Glu | Glu | Ile | Glu | Arg | Met | Val | Asn | Asp | Ala | Glu | Lys | Phe |
| 545 | | | | | 550 | | | | | 555 | | | | | 560 |
| Ala | Glu | Glu | Asp | Lys | Lys | Leu | Lys | Glu | Arg | Ile | Asp | Ala | Arg | Asn | Glu |
| | | | | 565 | | | | | 570 | | | | | 575 | |
| Leu | Glu | Ser | Tyr | Ala | Tyr | Ser | Leu | Lys | Asn | Gln | Ile | Gly | Asp | Lys | Glu |
| | | | 580 | | | | | 585 | | | | | 590 | | |
| Lys | Leu | Gly | Gly | Lys | Leu | Ser | Ser | Glu | Asp | Lys | Glu | Thr | Ile | Glu | Lys |
| | | 595 | | | | | 600 | | | | | 605 | | | |
| Ala | Val | Glu | Glu | Lys | Ile | Glu | Trp | Leu | Glu | Ser | His | Gln | Asp | Ala | Asp |
| | | 610 | | | | 615 | | | | | 620 | | | | |
| Ile | Glu | Asp | Phe | Lys | Ser | Lys | Lys | Lys | Glu | Leu | Glu | Glu | Val | Val | Gln |
| 625 | | | | | 630 | | | | | 635 | | | | | 640 |
| Pro | Ile | Val | Ser | Lys | Leu | Tyr | Gly | Ser | Ala | Gly | Pro | Pro | Pro | Thr | Gly |
| | | | | 645 | | | | | 650 | | | | | 655 | |
| Glu | Glu | Glu | Ala | Ala | Glu | Lys | Asp | Glu | Leu | | | | | | |
| | | | 660 | | | | | 665 | | | | | | | |

( 2 ) INFORMATION FOR SEQ ID NO:17:

( i ) SEQUENCE CHARACTERISTICS:
        ( A ) LENGTH: 2403 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

```
AAGGGGTTGA  CCGTCCGTCG  GCACACCACT  TATAATGCGG  GGTGCAAGCC  CCCCGTCTAA      60
AATTTTTTTT  TTTTCCATTT  TTGTCGTTAT  TGTTATTTCC  CGTTTTTTGT  TTTTTTTGAT     120
TTTTTCGGAG  CGACAAACCT  TTCGAAACAC  GTGTCCTGAA  AATTATCCTG  GGCTGCACGT     180
GATAATATGT  TACCCTGTCG  GGCGGCGCCT  CTTTTTCCCT  TTTCTCTCAC  TAGTCTCTTT     240
TTCCAATTTG  CCACCGTGTA  GCATTTTGTT  GTGCTGTTAC  AACCACAACA  AAACGAAAAA     300
CCCGTATGGA  CATACATATA  TATATATATA  TATATATATA  TATATTTTGT  TACGCGTGCA     360
TTTTCTTGTT  GCAAGCAGCA  TGTCTAATTG  GTAATTTTAA  AGCTGCCAAG  CTCTACATAA     420
```

| | | | | | | |
|---|---|---|---|---|---|---|
| AGAAAAACAT | ACATCTATCC | CGTTATGAAG | TTTTCTGCTG | GTGCCGTCCT | GTCATGGTCC | 480 |
| TCCCTGCTGC | TCGCCTCCTC | TGTTTTCGCC | CAACAAGAGG | CTGTGGCCCC | TGAAGACTCC | 540 |
| GCTGTCGTTA | AGTTGGCCAC | CGACTCTTTC | AATGAATACA | TTCAGTCGCA | CGACTTGGTG | 600 |
| CTTGCGGAGT | TTTTTGCTCC | ATGGTGTGGC | CACTGTAAGA | ACATGGCTCC | TGAATACGTT | 660 |
| AAAGCCGCCG | AGACTTTAGT | TGAGAAAAAC | ATTACCTTGG | CCCAGATCGA | CTGTACTGAA | 720 |
| AACCAGGATC | TGTGTATGGA | ACACAACATT | CCAGGGTTCC | CAAGCTTGAA | GATTTTCAAA | 780 |
| AACAGCGATG | TTAACAACTC | GATCGATTAC | GAGGGACCTA | GAACTGCCGA | GGCCATTGTC | 840 |
| CAATTCATGA | TCAAGCAAAG | CCAACCGGCT | GTCGCCGTTG | TTGCTGATCT | ACCAGCTTAC | 900 |
| CTTGCTAACG | AGACTTTTGT | CACTCCAGTT | ATCGTCCAAT | CCGGTAAGAT | TGACGCCGAC | 960 |
| TTCAACGCCA | CCTTTTACTC | CATGGCCAAC | AAACACTTCA | ACGACTACGA | CTTTGTCTCC | 1020 |
| GCTGAAAACG | CAGACGATGA | TTTCAAGCTT | TCTATTTACT | TGCCCTCCGC | CATGGACGAG | 1080 |
| CCTGTAGTAT | ACAACGGTAA | GAAAGCCGAT | ATCGCTGACG | CTGATGTTTT | TGAAAAATGG | 1140 |
| TTGCAAGTGG | AAGCCTTGCC | CTACTTTGGT | GAAATCGACG | GTTCCGTTTT | CGCCCAATAC | 1200 |
| GTCGAAAGCG | GTTTGCCTTT | GGGTTACTTG | TTCTACAATG | ACGAGGAAGA | ATTGGAAGAT | 1260 |
| TACAAGCCTC | TCTTTACCGA | GTTGGCCAAA | AAGAACAGAG | GTCTAATGAA | CTTTGTTAGC | 1320 |
| ATCGATGCCA | GAAAATTCGG | CAGACACGCC | GGCAACTTGA | ACATGAAGGA | ACAATTCCCT | 1380 |
| CTATTTGCCA | TCCACGACAT | GACTGAAGAC | TTGAAGTACG | GTTTGCCTCA | ACTCTCTGAA | 1440 |
| GAGGCGTTTG | ACGAATTGAG | CGACAAGATC | GTGTTGGAGT | CCAAGGCTAT | TGAATCTTTG | 1500 |
| GTTAAGGACT | TCTTGAAAGG | TGATGCCTCC | CCAATCGTGA | AGTCCCAAGA | GATCTTCGAG | 1560 |
| AACCAAGATT | CCTCTGTCTT | CCAATTGGTC | GGTAAGAACC | ATGACGAAAT | CGTCAACGAC | 1620 |
| CCAAAGAAGG | ACGTTCTTGT | TTTGTACTAT | GCCCCATGGT | GTGGTCACTG | TAAGAGATTG | 1680 |
| GCCCCAACTT | ACCAAGAACT | AGCTGATACC | TACGCCAACG | CCACAACCGA | CGTTTTGATT | 1740 |
| GCTAAACTAG | ACCACACTGA | AAACGATGTC | AGAGGCGTCG | TAATTGAAGG | TTACCCAACA | 1800 |
| ATCGTCTTAT | ACCCAGGTGG | TAAGAAGTCC | GAATCTGTTG | TGTACCAAGG | TTCAAGATCC | 1860 |
| TTGGACTCTT | TATTCGACTT | CATCAAGGAA | AACGGTCACT | TCGACGTCGA | CGGTAAGGCC | 1920 |
| TTGTACGAAG | AAGCCCAGGA | AAAAGCTGCT | GAGGAAGCCG | ATGCTGACGC | TGAATTGGCT | 1980 |
| GACGAAGAAG | ATGCCATTCA | CGATGAATTG | TAATTCTGAT | CACTTTGGTT | TTTCATTAAA | 2040 |
| TAGAGATATA | TAAGAAATTT | TCTAGGAAGT | TTTTTAAAA | AAAATCATAA | AAAGATAAAC | 2100 |
| GTTAAAATTC | AAACACAATA | GTCGTTCGCT | ATATTCGTCA | CACTGCACGA | ACGCCTTAGG | 2160 |
| GAAAGAGAAA | ATTGACCACG | TAGTAATAAT | AAGTGCATGG | CATCGTCTTT | TACTTAAATG | 2220 |
| TGGACACTTG | CTTTACTGCT | TAGGAAACTA | CTTATCTCAT | CCTCCTCCAT | TCCCTCCCT | 2280 |
| TTTCCAATTA | CCGTAATAAA | AGATGGCTGT | ATTTACTCCT | CCATCAGGTA | ATAGCAATTC | 2340 |
| CGACCATACT | CACACACAAG | ATGACCACGA | CAAAGATGAT | ATGATATCAA | GAAATTCTAT | 2400 |
| ACA | | | | | | 2403 |

( 2 ) INFORMATION FOR SEQ ID NO:18:

( i ) SEQUENCE CHARACTERISTICS:
        ( A ) LENGTH: 504 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Lys  Phe  Ser  Ala  Gly  Ala  Val  Leu  Ser  Trp  Ser  Ser  Leu  Leu  Leu
1              5                   10                       15

Ala  Ser  Ser  Val  Phe  Ala  Gln  Gln  Glu  Ala  Val  Ala  Pro  Glu  Asp  Ser
               20                  25                       30

Ala  Val  Val  Lys  Leu  Ala  Thr  Asp  Ser  Phe  Asn  Glu  Tyr  Ile  Gln  Ser
          35                       40                       45

His  Asp  Leu  Val  Lys  Ala  Ala  Glu  Thr  Leu  Val  Glu  Lys  Asn  Ile  Thr
50                            55                       60

Leu  Ala  Gln  Ile  Asp  Cys  Thr  Glu  Asn  Gln  Asp  Leu  Cys  Met  Glu  His
65                       70                  75                            80

Asn  Ile  Pro  Gly  Phe  Pro  Ser  Leu  Lys  Ile  Phe  Lys  Asn  Ser  Asp  Val
                    85                  90                            95

Asn  Asn  Ser  Ile  Asp  Tyr  Glu  Gly  Pro  Arg  Thr  Ala  Glu  Ala  Ile  Val
               100                 105                      110

Gln  Pro  Met  Ile  Lys  Gln  Ser  Gln  Pro  Ala  Val  Ala  Val  Val  Ala  Val
          115                      120                 125

Val  Ala  Asp  Leu  Pro  Ala  Tyr  Leu  Ala  Asn  Glu  Thr  Phe  Val  Thr  Pro
     130                      135                 140

Val  Ile  Val  Gln  Ser  Gly  Lys  Ile  Asp  Ala  Asp  Phe  Asn  Ala  Thr  Phe
145                      150                      155                      160

Tyr  Ser  Met  Ala  Asn  Lys  His  Phe  Asn  Asp  Tyr  Asp  Phe  Val  Ser  Ala
                    165                 170                      175

Glu  Asn  Ala  Asp  Asp  Asp  Phe  Lys  Leu  Ser  Ile  Tyr  Leu  Pro  Ser  Ala
               180                 185                      190

Met  Asp  Glu  Pro  Val  Val  Tyr  Asn  Gly  Lys  Lys  Ala  Asp  Ile  Ala  Asp
          195                 200                      205

Ala  Asp  Val  Phe  Glu  Lys  Trp  Leu  Gln  Val  Glu  Ala  Leu  Pro  Tyr  Phe
     210                      215                 220

Gly  Glu  Ile  Asp  Gly  Ser  Val  Phe  Ala  Gln  Tyr  Val  Glu  Ser  Gly  Leu
225                      230                 235                           240

Pro  Leu  Gly  Tyr  Leu  Phe  Tyr  Asn  Asp  Glu  Glu  Leu  Glu  Glu  Tyr
                    245                 250                      255

Lys  Pro  Leu  Phe  Thr  Glu  Leu  Ala  Lys  Lys  Asn  Arg  Gly  Leu  Met  Asn
               260                      265                      270

Phe  Val  Ser  Ile  Asp  Ala  Arg  Lys  Phe  Gly  Arg  His  Ala  Gly  Asn  Leu
               275                      280                 285

Asn  Met  Lys  Glu  Gln  Phe  Pro  Leu  Phe  Ala  Ile  His  Asp  Met  Thr  Glu
     290                      295                 300

Asp  Leu  Lys  Tyr  Gly  Leu  Pro  Gln  Leu  Ser  Glu  Glu  Ala  Phe  Asp  Glu
305                      310                 315                           320

Leu  Ser  Asp  Lys  Ile  Val  Leu  Glu  Ser  Lys  Ala  Ile  Glu  Ser  Leu  Val
               325                      330                      335

Lys  Asp  Phe  Leu  Lys  Gly  Asp  Ala  Ser  Pro  Ile  Val  Lys  Ser  Gln  Glu
               340                      345                      350

Ile  Phe  Glu  Asn  Gln  Asp  Ser  Ser  Val  Phe  Gln  Leu  Val  Gly  Lys  Asn
               355                      360                 365

His  Asp  Glu  Ile  Val  Asn  Asp  Pro  Lys  Lys  Asp  Val  Leu  Val  Leu  Tyr
     370                      375                 380

Ala  Pro  Trp  Cys  Gly  His  Cys  Lys  Arg  Leu  Ala  Pro  Thr  Tyr  Gln  Glu
385                      390                 395                           400

Leu  Ala  Asp  Thr  Tyr  Ala  Asn  Ala  Thr  Ser  Asp  Val  Leu  Ile  Ala  Lys
               405                      410                      415

Leu  Asp  His  Thr  Glu  Asn  Asp  Val  Arg  Gly  Val  Val  Ile  Glu  Gly  Tyr
```

|  |  |  |  | 420 |  |  |  |  | 425 |  |  |  |  | 430 |  |  |
|---|---|---|---|---|---|---|---|---|---|---|---|---|---|---|---|---|
| Pro | Thr | Ile<br>435 | Val | Leu | Tyr | Pro | Gly | Gly<br>440 | Lys | Lys | Ser | Glu<br>445 | Ser | Val | Val |  |
| Tyr | Gln<br>450 | Gly | Ser | Arg | Ser | Leu<br>455 | Asp | Ser | Leu | Phe | Asp<br>460 | Pro | Ile | Lys | Glu |  |
| Asn<br>465 | Gly | His | Phe | Asp | Val<br>470 | Asp | Gly | Lys | Ala | Leu<br>475 | Tyr | Glu | Glu | Ala | Gln<br>480 |  |
| Glu | Lys | Ala | Ala | Glu<br>485 | Glu | Ala | Asp | Ala | Asp<br>490 | Ala | Glu | Leu | Ala | Asp<br>495 | Glu |  |
| Glu | Asp | Ala | Ile<br>500 | His | Asp | Glu | Leu |  |  |  |  |  |  |  |  |  |

( 2 ) INFORMATION FOR SEQ ID NO:19:

( i ) SEQUENCE CHARACTERISTICS:
        ( A ) LENGTH: 2473 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

```
CCCCGGCGCC AACCTAGCTG CCCCGCCCGC TGCCGACGTC CGACATGCTG AGCCGTGCTT      60
TGCTGTGCCT GGCCCTGGCC TGGGCGGCTA GGGTGGGCGC CGACGCTCTG GAGGAGGAGG     120
ACAACGTCTC GGTGCTGAAG AAGAGCAACT TCGCAGAGCC GGCGGCGCAC AACTACCTGC     180
TGGTGGAGTT CTATGCCCCA TGGTGTGGCC ACTGCAAAGC ATCGGCCCCA GAGTATGCCA     240
AAGCTGCTGC AAAACTGAAG GCAGAAGGAC TCGAGATCCG ACTAGCAAAG GTGGACGCCA     300
CAGAAGAGTC TGACCTGGCC CAGCAGTATG GTGTCCGTGG CTACCCCACA ATCAAGTTCT     360
TCAAGAATGG AGACACAGCC TCCCCAAAGG AATATACAGC TGGCACGGAA GCTGACGACA     420
TTGTGAACTG GCTGAAGAAA CGCACAGGCC CAGCAGCCAC AACCCTGTCT GACACTGCAG     480
CTGCAGAGTC CTTGCTGGAC TCAAGCGAAG TGACGGCTAT CGGCTTCTTC AAGGACGCAG     540
GGTCAGACTC CGCCAAGCAG TTCTTGCTGG CAGCAGAGGC TGCTGATGAC ATACCTTTTG     600
GAATCACTTC CAATTGCGTG TTTTCCAAGT ACCAGCTGGA CAACGATGGG GTGGTCCTCT     660
TTAAGAAGTT TGATGAAGGC CGCAACAATT TTGAATGGTG AGATCACCAA GGAGAAGCTA     720
TTAGACTTCA TCAAGCACAA CCAGCTGCCT TTGGTCATCG AGTTCACTGA ACAGACAGCT     780
CCAAAGATTT TCGGAGGTGA AATCAAGACA CATATTCTGC TGTTCCTGCC CAAGAGTGTG     840
TCTGACTACG ATGGCAAATT GAGCAACTTT AAGAAAGCGG CCGAGGGCTT TAAGGGCAAG     900
ATCCTGTTCA TCTTCATCGA TAGTGACCAC ACTGACAACC AGCGCATACT TGAGTTCTTT     960
GGCCTGAAGA AGGAGGAATG TCCAGCTGTG CGGCTTATTA CCCTGGAGGA AGAGATGACC    1020
AAGTACAAAC CGGAGTCAGA CGAGCTGACA GCTGAGAAGA TCACACAATT TTGCCACCAC    1080
TTCCTGGAGG GCAAGATCAA GCCCCACCTG ATGAGCCAGG AACTGCCTGA AGACTGGGAC    1140
AAGCAGCCAG TGAAAGTGCT AGTTGGGAAA AACTTTGAGG AGGTTGCTTT TGATGAGAAA    1200
AAGAACGTGT TTGTTGAATT CTATGCTCCC TGGTGTGGTC ACTGCAAGCA GCTAGCCCCG    1260
ATTTGGGATA AACTGGGAGA GACATACAAA GACCATGAGA ATATCGTCAT CGCTAAGATG    1320
GACTCAACAG CCAATGAGGT GGAAGCTGTG AAGCTGCACA CCTTTCCCAC ACTCAAGTTC    1380
TTCCCAGCAA GTGCAGACAG AACGGTCATT GATTACAACG GTCAGCGGAC ACTAGATGGT    1440
TTTAAGAAAT TCTTGGAGAG CGGTGGCCAG GATGGAGCGG GGGACAATGA CGACCTCGAC    1500
```

-continued

| | | | | | |
|---|---|---|---|---|---|
| CTAGAAGAAG | CTTTAGAGCC | AGATATGGAA | GAAGACGACG | ATCAGAAAGC | CGTGAAGGAT | 1560 |
| GAACTGTAGT | CGAGAAGCCA | GATCTGGCGC | CCTGAACCCA | AAACCTCGGT | GGGCCATGTC | 1620 |
| CCAGCAGCCC | ACATCTCCGG | AGCCTGAGCC | TCACCCCAGG | AGGGAGCGCC | ATCAGAACCC | 1680 |
| AGGGAATCTT | TCTGAAGCCA | CACTCATCTG | ACACACGTAC | ACTTAAACCT | GTCTCTTCTT | 1740 |
| TTTTTGCTTT | TCAATTTTGG | AAAGGGATCT | CTGTCCAGGC | CAGCCCATCT | TGAAGGGCTA | 1800 |
| CGTTTTGTTT | TAATTGGTGG | TGTACTTTTT | TGTACGTGGA | TTTTGTCCCA | AGTGCTTGCT | 1860 |
| ACCATATTTG | GGGATTTCAC | ACTGGTAATG | TCTTTCCTGT | TAGAGAGGTT | TATGCTATCA | 1920 |
| CTTCAGATTT | CGTCTGTGAG | ATCTTTCATC | TTCCTGACAT | GTTCTCATGT | CGAGGTACTT | 1980 |
| GTTCCACCAC | GCAGATTCCC | CTGAGACCCC | TTCCTGCCCT | GCGCAGGAGG | CGATCGTTCT | 2040 |
| GGGTCGTATG | CTCTCTCTCT | CTCCACCTTG | TACTAGTGTT | GCCATGACAG | CTAGGCTTTT | 2100 |
| GTAGTTTGCA | TTTAACCTGG | GGATTTCTGC | ATCCTGTCAG | AGGCTGGGTC | CCCACGTGTG | 2160 |
| GAAAGAGAC | AGTGGTGGCT | TGCTGCCAGG | CACAGGCCAG | GCCTGGACAG | CTCTCACTCT | 2220 |
| TCTTAAGCCA | GAACTACCGA | CCAGCCGGCC | GGCTGTCCGC | ACATTACTCT | GGCTCCTGGA | 2280 |
| TCCTCTTCCA | GCATGGCATG | TGGCCTGTGT | GAGGCAGAAC | CGGGACCCTT | GATTCCCAGA | 2340 |
| CTGGGAGTCA | GCTAAGGACA | CTGGCGCTGA | ATGAAATGCC | CATTCTCAAG | GTCTATTTCT | 2400 |
| AAACCATAAT | GTTGGAATTG | AACACATTGG | CTAAATAAAG | TTGAAATTTT | ACTACCATAA | 2460 |
| AAAAAAAAAA | AAA | | | | | 2473 |

( 2 ) INFORMATION FOR SEQ ID NO:20:

( i ) SEQUENCE CHARACTERISTICS:
( A ) LENGTH: 510 amino acids
( B ) TYPE: amino acid
( D ) TOPOLOGY: linear ( i i ) MOLECULE TYPE: DNA (genomic)

( x i ) SEQUENCE DESCRIPTION: SEQ ID NO:20:

| Met | Leu | Ser | Arg | Ala | Leu | Leu | Cys | Leu | Ala | Leu | Ala | Trp | Ala | Ala | Arg |
|---|---|---|---|---|---|---|---|---|---|---|---|---|---|---|---|
| 1 | | | | 5 | | | | 10 | | | | | | 15 | |
| Val | Gly | Ala | Asp | Ala | Leu | Glu | Glu | Glu | Asp | Asn | Val | Leu | Val | Leu | Lys |
| | | | 20 | | | | | 25 | | | | | 30 | | |
| Lys | Ser | Asn | Phe | Ala | Glu | Pro | Ala | Ala | His | Asn | Tyr | Leu | Leu | Val | Glu |
| | | | 35 | | | | 40 | | | | | 45 | | | |
| Phe | Tyr | Ala | Pro | Trp | Cys | Gly | His | Cys | Lys | Ala | Leu | Ala | Pro | Glu | Tyr |
| | | | 50 | | | | 55 | | | | | 60 | | | |
| Ala | Lys | Ala | Ala | Ala | Lys | Leu | Lys | Ala | Glu | Gly | Ser | Glu | Ile | Arg | Leu |
| 65 | | | | | 70 | | | | | 75 | | | | | 80 |
| Ala | Lys | Val | Asp | Ala | Thr | Glu | Glu | Ser | Asp | Leu | Ala | Gln | Gln | Tyr | Gly |
| | | | | 85 | | | | | 90 | | | | | 95 | |
| Val | Arg | Gly | Tyr | Pro | Thr | Ile | Lys | Phe | Phe | Lys | Asn | Gly | Asp | Thr | Ala |
| | | | | 100 | | | | | 105 | | | | | 110 | |
| Ser | Pro | Lys | Glu | Tyr | Thr | Ala | Gly | Arg | Glu | Ala | Asp | Asp | Ile | Val | Asn |
| | | | 115 | | | | | 120 | | | | | 125 | | |
| Trp | Leu | Lys | Lys | Arg | Thr | Gly | Pro | Ala | Ala | Thr | Thr | Leu | Ser | Asp | Thr |
| | | | 130 | | | | | 135 | | | | | 140 | | |
| Ala | Ala | Ala | Glu | Ser | Leu | Val | Asp | Ser | Ser | Glu | Val | Thr | Val | Ile | Gly |
| | 145 | | | | | 150 | | | | | 155 | | | | 160 |
| Phe | Phe | Lys | Asp | Ala | Gly | Ser | Asp | Ser | Ala | Lys | Gln | Phe | Leu | Leu | Ala |
| | | | | 165 | | | | | 170 | | | | | 175 | |
| Ala | Glu | Ala | Val | Asp | Asp | Ile | Pro | Phe | Gly | Ile | Thr | Ser | Asn | Ser | Asp |

|   | 180 |   |   |   |   |   | 185 |   |   |   | 190 |   |   |   |
|---|---|---|---|---|---|---|---|---|---|---|---|---|---|---|
| Val | Phe | Ser<br>195 | Lys | Tyr | Gln | Leu | Asp<br>200 | Lys | Asp | Gly | Val | Val<br>205 | Leu | Phe | Lys |
| Lys | Phe<br>210 | Asp | Glu | Gly | Arg | Asn<br>215 | Asn | Phe | Glu | Gly | Glu<br>220 | Ile | Thr | Lys | Glu |
| Lys<br>225 | Leu | Leu | Asp | Phe | Ile<br>230 | Lys | His | Asn | Gln | Leu<br>235 | Pro | Leu | Val | Ile | Glu<br>240 |
| Phe | Thr | Glu | Gln | Thr<br>245 | Ala | Pro | Lys | Ile | Phe<br>250 | Gly | Gly | Glu | Ile | Lys<br>255 | Thr |
| His | Ile | Leu | Leu<br>260 | Phe | Leu | Pro | Lys | Ser<br>265 | Val | Ser | Asp | Tyr | Asp<br>270 | Gly | Lys |
| Leu | Ser | Asn<br>275 | Phe | Lys | Lys | Ala | Ala<br>280 | Glu | Gly | Phe | Lys | Gly<br>285 | Lys | Ile | Leu |
| Phe | Ile<br>290 | Phe | Ile | Asp | Ser | Asp<br>295 | His | Thr | Asp | Asn | Gln<br>300 | Arg | Ile | Leu | Glu |
| Phe<br>305 | Phe | Gly | Leu | Lys | Lys<br>310 | Glu | Glu | Cys | Pro | Ala<br>315 | Val | Arg | Leu | Ile | Thr<br>320 |
| Leu | Glu | Glu | Glu | Met<br>325 | Thr | Lys | Tyr | Lys | Pro<br>330 | Glu | Ser | Asp | Glu | Leu<br>335 | Thr |
| Ala | Glu | Lys | Ile<br>340 | Thr | Gln | Phe | Cys | His<br>345 | His | Phe | Leu | Glu | Gly<br>350 | Lys | Ile |
| Lys | Pro | His<br>355 | Leu | Met | Ser | Gln | Ile<br>360 | Glu | Leu | Pro | Glu | Asp<br>365 | Trp | Asp | Lys |
| Gln | Pro<br>370 | Val | Lys | Val | Leu | Val<br>375 | Gly | Lys | Asn | Phe | Glu<br>380 | Glu | Val | Ala | Pro |
| Asp<br>385 | Glu | Lys | Lys | Asn | Val<br>390 | Phe | Val | Glu | Phe | Tyr<br>395 | Ala | Pro | Trp | Cys | Gly<br>400 |
| His | Cys | Lys | Gln | Leu<br>405 | Ala | Pro | Ile | Trp | Asp<br>410 | Lys | Leu | Gly | Glu | Thr<br>415 | Tyr |
| Lys | Asp | His | Asp<br>420 | Glu | Asn | Ile | Val | Ile<br>425 | Ala | Lys | Met | Asp | Ser<br>430 | Thr | Ala |
| Asn | Glu | Val<br>435 | Glu | Ala | Val | Lys | Val<br>440 | His | Ser | Phe | Pro | Thr<br>445 | Leu | Lys | Phe |
| Phe | Pro<br>450 | Ala | Ser | Ala | Asp | Arg<br>455 | Thr | Val | Ile | Asp | Tyr<br>460 | Asn | Gly | Glu | Arg |
| Thr<br>465 | Leu | Asp | Gly | Phe | Lys<br>470 | Lys | Phe | Leu | Glu | Ser<br>475 | Gly | Gly | Gln | Asp | Gly<br>480 |
| Ala | Gly | Asp | Asn | Asp<br>485 | Asp | Leu | Asp | Leu | Glu<br>490 | Glu | Ala | Leu | Glu | Pro<br>495 | Asp |
| Met | Glu | Glu | Asp<br>500 | Asp | Asp | Gln | Lys | Ala<br>505 | Val | Lys | Asp | Glu | Leu<br>510 |   |   |

What is claimed:

1. A method for increasing secretion of an overexpressed secretable gene product from a yeast host cell which comprises effecting the increased expression of a KAR2 chaperone protein in said yeast host cell.

2. The method of claim 1 wherein said expression of said chaperone protein is effected by inducing expression of a nucleic acid encoding said chaperone protein.

3. The method of claim 2 wherein said nucleic acid is present in an expression vector.

4. The method of claim 1 wherein said gene product is selected from the group consisting of erythropoietin, insulin, somatotropin, growth hormone releasing factor, transforming growth factor α, transforming growth factor β, epidermal growth factor, fibroblast growth factor, nerve growth factor, insulin-like growth factor I, insulin-like growth factor II, clotting Factor VIII, superoxide dismutase, α-interferon, γ-interferon, interleukin-1, interleukin-2, interleukin-3, interleukin-4, interleukin-5, interleukin-6, granulocyte colony stimulating factor, multi-lineage colony stimulating activity, granulocyte-macrophage colony stimulating factor, macrophage colony stimulating factor, T cell growth factor and lymphotoxin.

5. The method of claim 1 wherein said gene product is erythropoietin.

6. A method for increasing secretion of an overexpressed secretable gene product from a yeast host cell which comprises:

a) effecting the increased expression of a KAR2 chaperone protein and the overexpression of said gene product in said yeast host cell; and b) cultivating said yeast host cell under conditions suitable for secretion of said overexpressed gene product.

7. The method of claim 6 wherein said increased expression of said chaperone protein is effected by transforming said yeast host cell with an expression vector comprising a nucleic acid encoding said KAR2 chaperone protein.

8. The method of claim 7 wherein said overexpression of said gene product is effected by transforming said yeast host cell with an expression vector comprising a nucleic acid encoding said gene product.

9. The method of claim 6 wherein said gene product is selected from the group consisting of erythropoietin, insulin, somatotropin, growth hormone releasing factor, transforming growth factor α, transforming growth factor β, epidermal growth factor, fibroblast growth factor, nerve growth factor, insulin-like growth factor I, insulin-like growth factor II, clotting Factor VIIII, superoxide dismutase, α-interferon, γ-interferon, interleukin-1, interleukin-2, interleukin-3, interleukin-4, interleukin-5, interleukin-6, granulocyte colony stimulating factor, multi-lineage colony stimulating activity, granulocyte-macrophage colony stimulating factor, macrophage colony stimulating factor, T cell growth factor and lymphotoxin.

10. The method of claim 6 wherein said gene product is erythropoietin.

11. A method for increasing secretion of an overexpressed gene product from a yeast host cell which comprises effecting the expression of a KAR2 chaperone protein and a yeast protein disulfide isomerase in said host cell.

12. The method of claim 11 wherein said gene product is selected from the group consisting of erythropoietin, insulin, somatotropin, growth hormone releasing factor, transforming growth factor α, transforming growth factor β, epidermal growth factor, fibroblast growth factor, nerve growth factor, insulin-like growth factor I, insulin-like growth factor II, clotting Factor VIIII, superoxide dismutase, α-interferon, γ-interferon, interleukin-1, interleukin-2, interleukin-3, interleukin-4, interleukin-5, interleukin-6, granulocyte colony stimulating factor, multi-lineage colony stimulating activity, granulocyte-macrophage colony stimulating factor, macrophage colony stimulating factor, T cell growth factor and lymphotoxin.

13. The method in claim 11 wherein said gene product is erythropoietin.

\* \* \* \* \*